(12) United States Patent
Kurosawa et al.

(10) Patent No.: US 8,101,553 B1
(45) Date of Patent: Jan. 24, 2012

(54) ANTIBODY LIBRARY

(75) Inventors: Yoshikazu Kurosawa, Nagoya (JP);
Yasushi Akahori, Nagoya (JP);
Yoshitaka Iba, Nagoya (JP); Kazuhiko Morino, Toyoake (JP); Midori Shinohara, Toyoake (JP); Motohide Takahashi, Tokorozawa (JP); Yoshinobu Okuno, Toyonaka (JP); Kimiyasu Shiraki, Toyama (JP)

(73) Assignee: Medical & Biological Laboratories Co., Ltd., Aichi (JP)

( * ) Notice: Subject to any disclaimer, the term of this patent is extended or adjusted under 35 U.S.C. 154(b) by 765 days.

(21) Appl. No.: 10/204,773

(22) PCT Filed: Feb. 22, 2001

(86) PCT No.: PCT/JP01/01298
§ 371 (c)(1),
(2), (4) Date: Feb. 24, 2003

(87) PCT Pub. No.: WO01/62907
PCT Pub. Date: Aug. 30, 2001

(30) Foreign Application Priority Data

Feb. 22, 2000 (JP) ................................ 2000-050543

(51) Int. Cl.
*C40B 50/06* (2006.01)
(52) U.S. Cl. ..................... 506/26; 424/130.1; 424/141.1; 506/9
(58) Field of Classification Search .................. None
See application file for complete search history.

(56) References Cited

U.S. PATENT DOCUMENTS

| | | | |
|---|---|---|---|
| 6,291,158 B1 | 9/2001 | Winter et al. ...................... | 435/6 |
| 6,291,159 B1 | 9/2001 | Winter et al. ...................... | 435/6 |
| 6,291,160 B1 | 9/2001 | Lerner et al. ...................... | 435/6 |
| 6,476,198 B1 * | 11/2002 | Kang ......................... | 530/387.3 |

FOREIGN PATENT DOCUMENTS

| | | |
|---|---|---|
| WO | WO 90/05144 A1 | 5/1990 |
| WO | WO 90/14430 A1 | 11/1990 |
| WO | WO 90/14443 A1 | 11/1990 |
| WO | WO 91/10737 A1 | 7/1991 |
| WO | WO-92/01047 | 1/1992 |
| WO | WO-99/20749 | 4/1999 |

OTHER PUBLICATIONS

Portolano et al. 1993 Lack of Promiscuity in autoantigen-sepcific H and L chain combinations as revealed by human H and L chain "roulette." J. Immunology 150:880-887.*
Pereira et al. 1998 Cardiolipin binding a light chain from lupus-prone mice. Biochemistry 37:1430-1437.*
Rosok et al. 1998 J. Immunol. 160:2353-2359.*
Sassano et al (1993 J. Immunology 151:5822-5839).*
de Kruif et al 1995 J. Mol. Biol. 248: 97-105.*
Hoogenboom et al 1991 Nucleic Acids Research 19:4133-4137.*
Nissim et al 1994 The EMBO Journal 13:692-698.*
A.M. Cuisinier, et al., *Mol. Immunol*, 29(11), pp. 1363-1373 (1992).
A. Knappik, et al., *J Mol Biol*, 296(1), pp. 57-86 (2000).
M. Little, et al., *J Immunol Methods*, 231(1-2), pp. 3-9 (1999).
M. Czerwinski, et al., *J Immunol*, 160(9), pp. 4406-4417 (1998).
J.D. Marks, et al., *J Mol Biol*, 222(3), pp. 581-597 (1991).
T.J. Vaughan, et al., *Nat Biotechnol*, 14(3), pp. 309-314 (1996).
A.D. Griffiths, et al., *EMBO J*, 13(14), pp. 3245-3260 (1994).
J. McCafferty, et al., *Nature*, 348(6301), pp. 552-554 (1990).
W.D. Huse, et al., *Science*, 246(4935), pp. 1275-1281 (1989).
K. Suzuki, et al., "The 23rd Annual Meeting of MBSJ", 3PB-175 (2000).
Y. Kurosawa, "Rinshou Men eki", 28 (8), pp. 1077-1085 (1996).
L. Aujame et al., "High Affinity Human Antibodies by Phage Display", Human Antibodies, vol. 8, No. 4, pp. 155-168 (1997).
CF Barbas et al., "Semisynthetic Combinatorial Antibody Libraries: A Chemical Solution to the Diversity Problem", Proc. Nat. Acad. of Sci., vol. 89. pp. 4457-4461 (1992).
K. Higo-Moriguchi et al., "Isolation of Human Monoclonal Antibodies That Neutralize Human Rotavirus", Journ. of Virol., vol. 78, No. 7, pp. 3325-3332 (2004).
H. Hoogenboom et al., "Antibody Phage Display Technology and its Applications", Immunotechnology, vol. 4, pp. 1-20 (1998).
Y. Iba et al., "Comparison of Strategies for thr Construction of Libraries of Artificial Antibodies", Immunol. Cell Biol., vol. 75, No. 2, pp. 217-221 (1997).
Y. Iba et al., "Expression Vectors for the Introduction of Highly Diverged Sequences into the Six Complementarity-Determining Regions of an Antibody", Gene, vol. No. 1, 194, pp. 35-46 (1997).
M. Persson et al., "Generation of Diverse High-Affinity Human Monoclonal Antibodies by Repertoire Cloning", Proc. Natl. Acad. Sci., vol. 88, pp. 2432-2436 (1991).
R. Powell et al., "Construction, Assembly and Selection of Combinatorial Antibody Libraries", Gen Eng. with PCR, vol. 5, pp. 155-172 (1998).
J.L. Hillson et al., "The Structural Basis of Germline-encoded VH3 Immunoglobulin Binding to *Staphylococcal* Protein A", J. Exp. Med., vol. 178, pp. 331-336 (1993).
B.H.K. Nilson et al., "Protein L from *Peptostreptococcus magnus* Binds to the k Light Chain Variable Domain", The Journal of Biological Chemistry, 267(4), pp. 2234-2239 (1992).

* cited by examiner

*Primary Examiner* — Christopher M. Gross
(74) *Attorney, Agent, or Firm* — Peter F. Corless; Christine C. O'Day; Edwards Wildman Palmer LLP

(57) ABSTRACT

An antibody library is prepared by selecting a light chain variable region capable of binding to the variable region of heavy chain to reproduce an active conformation and using the same. Because of being capable of maintaining the diversity of the heavy chain variable region at a high ratio in vitro, the antibody library of the present invention is expected as enabling the acquisition of antibodies with various binding activities.

10 Claims, 11 Drawing Sheets

Fig. 3

```
AAGCTTGCATGCAAATTCTATTTCAAGGAGACAGTCATAATGAAATACCTATTGCCTACGGCAGCCGCTGGA
TTGTTATTACTCGCTGCCCAACCAGCGATGGCCCAGGTGCAGCTGCAGCAGTCTGGGGCAGAGCTTGTGAAG
CCAGGGGCCTCAGTCAAGTTGTCCTGCACAGCTTCTGGCTTCAACATTAAAGACACCTATATGCACTGGGTG
AAGCAGAGGCCTGAAAAGGGTCTAGAATTCCCTGACATCTGAGGACACTGCCGTCTATTACTGTGCTGGTTA
TGATTACGGCAACTTTGACTACTGGGGCCAAGGCACCACGGTCACCGTCTCGAGCGCCTCCACCAAGGGCCC
ATCGGTCTTCCCCCTGGCACCCTCCTCCAAGAGCACCTCTGGGGGCACAGCGGCCCTGGGCTGCCTGGTCAA
GGACTACTTCCCCGAACCGGTGACGGTGTCGTGGAACTCAGGCGCCCTGACCAGCGGCGTGCACACCTTCCC
GGCTGTCCTACAGTCCTCAGGACTCTACTCCCTCAGCAGCGTCGTGACCGTGCCCTCCAGCAGCTTGGGCAC
CCAGACCTACATCTGCAACGTGAATCACAAGCCCAGCAACACCAAGGTGGACAAGAAAGTTGAGCCCAAATC
TTGTCATCACCATCATCACCATTAATAAGAGCTATCCCGGGAGCTTGCATGCAAATTCTATTTCAAGGAGAC
AGTCATAATGAAATACCTATTGCCTACGGCAGCCGCTGGATTGTTATTACTCGCGGCCCAGCCGGCCATGGC
CACTAGTGACATCGAGCTCACCCAGTCTCCAGCCTCCCTTTCTGCGTCTGTGGGAGAAACTGTCACCATCAC
ATGTCGAGCAAGTGGGAATATTCACAATTATTTAGCATGGTACCAAGCTCGAGATCAAACGGGCTGATGCTG
CACCAACTGTATCCATCTTCCCACCATCCAGTGAGCAGTTAACATCTGGAGGTGCCTCAGTCGTGTGCTTCT
TGAACAGCTTCTACCCCAAAGACATCAATGTCAAGTGGAAGATTGATGGCAGTGAACGACAAAATGGCGTCC
TGAACAGTTGGACTGATCAGGACAGCAAAGACAGCACCTACAGCATGAGCAGCACCCTCACGTTGACCAAGG
ACGAGTATGAACGACATAACAGCTATACCTGTGAGGCCACTCACAAGACATCAACTTCACCCATTGTCAAGA
GCTTCAACAGGAATGAGTGTTCGGCGCGCCAGTCGACTCCATTCGTTTGTGAATATCAAGGCCAATCGTCTG
ACCTGCCTCAACCTCCTGTCAATGCTGGCGGCGGCTCTGGTGGTGGTTCTGGTGGCGGCTCTGAGGGTGGTG
GCTCTGAGGGTGGCGGTTCTGAGGGTGGCGGCTCTGAGGGAGGCGGTTCCGGTGGTGGCTCTGGTTCCGGTG
ATTTTGATTATGAAAAGATGGCAAACGCTAATAAGGGGGCTATGACCGAAAATGCCGATGAAAACGCGCTAC
AGTCAGACGCTAAAGGCAAACTTGATTCTGTCGCTACTGATTACGGTGCTGCTATCGATGGTTTCATTGGTG
ACGTTTCCGGCCTTGCTAATGGTAATGGTGCTACTGGTGATTTTGCTGGCTCTAATTCCCAAATGGCTCAAG
TCGGTGACGGTGATAATTCACCTTTAATGAATAATTTCCGTCAATATTTACCTTCCCTCCCTCAATCGGTTG
AATGTCGCCCTTTTGTCTTTGGCGCTGGTAAACCATATGAATTTTCTATTGATTGTGACAAAATAAACTTAT
TCCGTGGTGTCTTTGCGTTTCTTTTATATGTTGCCACCTTTATGTATGTATTTTCTACGTTTGCTAACATAC
TGCGTAATAAGGAGTCTTAATCATGCCAGTTCTTTTGGGTGCTAGCTGTCGACTGCGCAACACGATGAAGCC
GTAGACAACAAATTCAACAAAGAACAACAAAACGCGTTCTATGAGATCTTACATTTACCTAACTTAAACGAA
GAACAACGAAACGCCTTCATCCAAAGTTTAAAAGATGACCCAAGCCAAAGCGCTAACCTTTTAGCAGAAGCT
AAAAAGCTAAATGATGCTCAGGCGCCGAAAGTAGACAACAAATTCAACAAAGAACAACAAAACGCGTTCTAT
GAGATCTTACATTTACCTAACTTAAACGAAGAACAACGAAACGCCTTCATCCAAAGTTTAAAAGATGACCCA
AGCCAAAGCGCTAACCTTTTAGCAGAAGCTAAAAAGCTAAATGATGCTCAGGCGCCGAAAGTAGACGCGAAT
TAGCTGGGAATTAATTC
```

Fig. 4

```
                                        M  K  Y  L  L  P  T  A  A  A  G
AAGCTTGCATGCAAATTCTATTTCAAGGAGACAGTCATAATGAAATACCTATTGCCTACGGCAGCCGCTGGA
HindIII L  L  L  L  A  A  Q  P  A  M  A  Q  V  Q  L  Q  Q  S  G  A  E  L  V  K
TTGTTATTACTCGCTGCCCAACCAGCGATGGCCCAGGTGCAGCTGCAGCAGTCTGGGGCAGAGCTTGTGAAG
                                              PstI P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGTG K  Q  R  P  E  K  G ---------- L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTTA
                     XbaI EcoRI D  Y  G  N  F  D  Y  W  G  Q  G  T  T  V  T  V  S  S  A  S  T  K  G  P
TGATTACGGCAACTTTGACTACTGGGGCCAAGGCACCACGGTCACCGTCTCGAGCGCCTCCACCAAGGGCCC
                                      BstPI   XhoI S  V  F  P  L  A  P  S  S  K  S  T  S  G  G  T  A  A  L  G  C  L  V  K
ATCGGTCTTCCCCCTGGCACCCTCCTCCAAGAGCACCTCTGGGGGCACAGCGGCCCTGGGCTGCCTGGTCAA D  Y  F  P  E  P  V  T  V  S  W  N  S  G  A  L  T  S  G  V  H  T  F  P
GGACTACTTCCCCGAACCGGTGACGGTGTCGTGGAACTCAGGCGCCCTGACCAGCGGCGTGCACACCTTCCC A  V  L  Q  S  S  G  L  Y  S  L  S  S  V  V  T  V  P  S  S  S  L  G  T
GGCTGTCCTACAGTCCTCAGGACTCTACTCCCTCAGCAGCGTCGTGACCGTGCCCTCCAGCAGCTTGGGCAC Q  T  Y  I  C  N  V  N  H  K  P  S  N  T  K  V  D  K  K  V  E  P  K  S
CCAGACCTACATCTGCAACGTGAATCACAAGCCCAGCAACACCAAGGTGGACAAGAAAGTTGAGCCCAAATC C  H  H  H  H  H  H  *  *
TTGTCATCACCATCATCACCATTAATAAGAGCTATCCCGGGAGCTTGCATGCAAATTCTATTTCAAGGAGAC
                                SmaI M  K  Y  L  L  P  T  A  A  A  G  L  L  L  L  A  A  Q  P  A  M  A
AGTCATAATGAAATACCTATTGCCTACGGCAGCCGCTGGATTGTTATTACTCGCGGCCCAGCCGGCCATGGC
                                                       SfiI      NcoI T  S  D  I  E  L  T  Q  S  P  A  S  L  S  A  S  V  G  E  T  V  T  I  T
CACTAGTGACATCGAGCTCACCCAGTCTCCAGCCTCCCTTTCTGCGTCTGTGGGAGAAACTGTCACCATCAC
  SpeI      SacI C  R  A  S  G  N  I  H  N  Y  L  A ------- K  L  E  I  K  R  A  D  A  A
ATGTCGAGCAAGTGGGAATATTCACAATTATTTAGCATGGTACCAAGCTCGAGATCAAACGGGCTGATGCTG
                                         KpnI     XhoI
```

Fig. 5

```
  P  T  V  S  I  F  P  P  S  S  E  Q  L  T  S  G  G  A  S  V  V  C  F  L
CACCAACTGTATCCATCTTCCCACCATCCAGTGAGCAGTTAACATCTGGAGGTGCCTCAGTCGTGTGCTTCT

N  S  F  Y  P  K  D  I  N  V  K  W  K  I  D  G  S  E  R  Q  N  G  V  L
TGAACAGCTTCTACCCCAAAGACATCAATGTCAAGTGGAAGATTGATGGCAGTGAACGACAAAATGGCGTCC

N  S  W  T  D  Q  D  S  K  D  S  T  Y  S  M  S  S  T  L  T  L  T  K  D
TGAACAGTTGGACTGATCAGGACAGCAAAGACAGCACCTACAGCATGAGCAGCACCCTCACGTTGACCAAGG

E  Y  E  R  H  N  S  Y  T  C  E  A  T  H  K  T  S  T  S  P  I  V  K  S
ACGAGTATGAACGACATAACAGCTATACCTGTGAGGCCACTCACAAGACATCAACTTCACCCATTGTCAAGA

F  N  R  N  E  C  S  A  R  Q  S  T  P  F  V  C  E  Y  Q  G  Q  S  S  D
GCTTCAACAGGAATGAGTGTTCGGCGCGCCAGTCGACTCCATTCGTTTGTGAATATCAAGGCCAATCGTCTG
                          AscI    SalI
  L  P  Q  P  P  V  N  A  G  G  G  S  G  G  G  S  G  G  G  S  E  G  G  G
ACCTGCCTCAACCTCCTGTCAATGCTGGCGGCGGCTCTGGTGGTGGTTCTGGTGGCGGCTCTGAGGGTGGTG

S  E  G  G  G  S  E  G  G  G  S  E  G  G  G  S  G  G  G  S  G  S  G  D
GCTCTGAGGGTGGCGGTTCTGAGGGTGGCGGCTCTGAGGGAGGCGGTTCCGGTGGTGGCTCTGGTTCCGGTG

F  D  Y  E  K  M  A  N  A  N  K  G  A  M  T  E  N  A  D  E  N  A  L  Q
ATTTTGATTATGAAAAGATGGCAAACGCTAATAAGGGGGCTATGACCGAAAATGCCGATGAAAACGCGCTAC

S  D  A  K  G  K  L  D  S  V  A  T  D  Y  G  A  A  I  D  G  F  I  G  D
AGTCAGACGCTAAAGGCAAACTTGATTCTGTCGCTACTGATTACGGTGCTGCTATCGATGGTTTCATTGGTG

V  S  G  L  A  N  G  N  G  A  T  G  D  F  A  G  S  N  S  Q  M  A  Q  V
ACGTTTCCGGCCTTGCTAATGGTAATGGTGCTACTGGTGATTTTGCTGGCTCTAATTCCCAAATGGCTCAAG

G  D  G  D  N  S  P  L  M  N  N  F  R  Q  Y  L  P  S  L  P  Q  S  V  E
TCGGTGACGGTGATAATTCACCTTTAATGAATAATTTCCGTCAATATTTACCTTCCCTCCCTCAATCGGTTG

C  R  P  F  V  F  G  A  G  K  P  Y  E  F  S  I  D  C  D  K  I  N  L  F
AATGTCGCCCTTTTGTCTTTGGCGCTGGTAAACCATATGAATTTTCTATTGATTGTGACAAAATAAACTTAT

R  G  V  F  A  F  L  L  Y  V  A  T  F  M  Y  V  F  S  T  F  A  N  I  L
TCCGTGGTGTCTTTGCGTTTCTTTTATATGTTGCCACCTTTATGTATGTATTTCTACGTTTGCTAACATAC

R  N  K  E  S  *                                S  T  A  Q  H  D  E  A
TGCGTAATAAGGAGTCTTAATCATGCCAGTTCTTTTGGGTGCTAGCTGTCGACTGCGCAACACGATGAAGCC
                                              NheI    SalI
  V  D  N  K  F  N  K  E  Q  Q  N  A  F  Y  E  I  L  H  L  P  N  L  N  E
GTAGACAACAAATTCAACAAAGAACAACAAAACGCGTTCTATGAGATCTTACATTTACCTAACTTAAACGAA

E  Q  R  N  A  F  I  Q  S  L  K  D  D  P  S  Q  S  A  N  L  L  A  E  A
GAACAACGAAACGCCTTCATCCAAAGTTTAAAAGATGACCCAAGCCAAAGCGCTAACCTTTTAGCAGAAGCT

K  K  L  N  D  A  Q  A  P  K  V  D  N  K  F  N  K  E  Q  Q  N  A  F  Y
AAAAAGCTAAATGATGCTCAGGCGCCGAAAGTAGACAACAAATTCAACAAAGAACAACAAAACGCGTTCTAT
```

Fig. 6

```
E   I   L   H   L   P   N   L   N   E   E   Q   R   N   A   F   I   Q   S   L   K   D   D   P
GAGATCTTACATTTACCTAACTTAAACGAAGAACAACGAAACGCCTTCATCCAAAGTTTAAAAGATGACCCA

S   Q   S   A   N   L   L   A   E   A   K   K   L   N   D   A   Q   A   P   K   V   D   A   N
AGCCAAAGCGCTAACCTTTTAGCAGAAGCTAAAAAGCTAAATGATGCTCAGGCGCCGAAAGTAGACGCGAAT

*
TAGCTGGGAATTAATTC
```

FIG. 7

AAGCTTGCATGCAAATTCTATTTCAAGGAGACAGTCATAATGAAATACCTATTGCCTACGGCAGCCGCTGGA
TTGTTATTACTCGCGGCCCAGCCGGCCATGGCCCAGGTGCAGCTGCAGCAGTCTGGGGCAGAGCTTGTGAAG
CCAGGGGCCTCAGTCAAGTTGTCCTGCACAGCTTCTGGCTTCAACATTAAAGACACCTATATGCACTGGGTG
AAGCAGAGGCCTGAAAAGGGTCTAGAATTCCCTGACATCTGAGGACACTGCCGTCTATTACTGTGCTGGTTA
TGATTACGGCAACTTTGACTACTGGGGCCAAGGCACCACGGTCACCGTCTCCTCAGGCGGTGGCGGATCAGG
TGGCGGTGGAAGTGGCGGTGGTGGGTCTACTAGTGACATCGAGCTCACCCAGTCTCCAGCCTCCCTTTCTGC
GTCTGTGGGAGAAACTGTCACCATCACATGTCGAGCAAGTGGGAATATTCACAATTATTTAGCATGGTACCA
GCAGAAACCAGGGAAATCTCCTCAGCTCCTGGTCTATAATGCAAAAACCTTAGCAGATGGTGTGCCATCAAG
GTTCAGTGGCAGTGGATCCGGAACACAATATTCTCTCAAGATCAACAGCCTGCAGCCTGAAGATTTTGGGAG
TTATTACTGTCAACATTTTTGGAGTACTCCGTGGACGTTCGGTGGAGGTACCAAGCTCGAGTCGACTCCATT
CGTTTGTGAATATCAAGGCCAATCGTCTGACCTGCCTCAACCTCCTGTCAATGCTGGCGGCGGCTCTGGTGG
TGGTTCTGGTGGCGGCTCTGAGGGTGGTGGCTCTGAGGGTGGCGGTTCTGAGGGTGGCGGCTCTGAGGGAGG
CGGTTCCGGTGGTGGCTCTGGTTCCGGTGATTTTGATTATGAAAAGATGGCAAACGCTAATAAGGGGGCTAT
GACCGAAAATGCCGATGAAAACGCGCTACAGTCAGACGCTAAAGGCAAACTTGATTCTGTCGCTACTGATTA
CGGTGCTGCTATCGATGGTTTCATTGGTGACGTTTCCGGCCTTGCTAATGGTAATGGTGCTACTGGTGATTT
TGCTGGCTCTAATTCCCAAATGGCTCAAGTCGGTGACGGTGATAATTCACCTTTAATGAATAATTTCCGTCA
ATATTTACCTTCCCTCCCTCAATCGGTTGAATGTCGCCCTTTTGTCTTTGGCGCTGGTAAACCATATGAATT
TTCTATTGATTGTGACAAAATAAACTTATTCCGTGGTGTCTTTGCGTTTCTTTTATATGTTGCCACCTTTAT
GTATGTATTTTCTACGTTTGCTAACATACTGCGTAATAAGGAGTCTTAATCATGCCAGTTCTTTTGGGTGCT
AGCTGTCGACTGCGCAACACGATGAAGCCGTAGACAACAAATTCAACAAAGAACAACAAAACGCGTTCTATG
AGATCTTACATTTACCTAACTTAAACGAAGAACAACGAAACGCCTTCATCCAAAGTTTAAAAGATGACCCAA
GCCAAAGCGCTAACCTTTTAGCAGAAGCTAAAAAGCTAAATGATGCTCAGGCGCCGAAAGTAGACAACAAAT
TCAACAAAGAACAACAAAACGCGTTCTATGAGATCTTACATTTACCTAACTTAAACGAAGAACAACGAAACG
CCTTCATCCAAAGTTTAAAAGATGACCCAAGCCAAAGCGCTAACCTTTTAGCAGAAGCTAAAAAGCTAAATG
ATGCTCAGGCGCCGAAAGTAGACGCGAATTAGCTGGGAATTAATTC

Fig. 8

```
                                          M  K  Y  L  L  P  T  A  A  A  G
AAGCTTGCATGCAAATTCTATTTCAAGGAGACAGTCATAATGAAATACCTATTGCCTACGGCAGCCGCTGGA
HindIII L  L  L  L  A  A  Q  P  A  M  A  Q  V  Q  L  Q  Q  S  G  A  E  L  V  K
TTGTTATTACTCGCGGCCCAGCCGGCCATGGCCCAGGTGCAGCTGCAGCAGTCTGGGGCAGAGCTTGTGAAG
         SfiI        NcoI          PstI P  G  A  S  V  K  L  S  C  T  A  S  G  F  N  I  K  D  T  Y  M  H  W  V
CCAGGGGCCTCAGTCAAGTTGTCCTGCACAGCTTCTGGCTTCAACATTAAAGACACCTATATGCACTGGGTG K  Q  R  P  E  K  G ---------- L  T  S  E  D  T  A  V  Y  Y  C  A  G  Y
AAGCAGAGGCCTGAAAAGGGTCTAGAATTCCCTGACATCTGAGGACACTGCCGTCTATTACTGTGCTGGTTA
                    XbaI EcoRI D  Y  G  N  F  D  Y  W  G  Q  G  T  T  V  T  V  S  S  G  G  G  G  S  G
TGATTACGGCAACTTTGACTACTGGGGCCAAGGCACCACGGTCACCGTCTCCTCAGGCGGTGGCGGATCAGG
                                    BstPI G  G  S  G  G  G  G  S  T  S  D  I  E  L  T  Q  S  P  A  S  L  S  A
TGGCGGTGGAAGTGGCGGTGGTGGGTCTACTAGTGACATCGAGCTCACCCAGTCTCCAGCCTCCCTTTCTGC
                            SpeI       SacI S  V  G  E  T  V  T  I  T  C  R  A  S  G  N  I  H  N  Y  L  A  W  Y  Q
GTCTGTGGGAGAAACTGTCACCATCACATGTCGAGCAAGTGGGAATATTCACAATTATTTAGCATGGTACCA
                                                                    KpnI Q  K  P  G  K  S  P  Q  L  L  V  Y  N  A  K  T  L  A  D  G  V  P  S  R
GCAGAAACCAGGGAAATCTCCTCAGCTCCTGGTCTATAATGCAAAAACCTTAGCAGATGGTGTGCCATCAAG F  S  G  S  G  S  G  T  Q  Y  S  L  K  I  N  S  L  Q  P  E  D  F  G  S
GTTCAGTGGCAGTGGATCCGGAACACAATATTCTCTCAAGATCAACAGCCTGCAGCCTGAAGATTTTGGGAG
                BamHI Y  Y  C  Q  H  F  W  S  T  P  W  T  F  G  G  G  T  K  I  E  S  T  P  F
TTATTACTGTCAACATTTTTGGAGTACTCCGTGGACGTTCGGTGGAGGTACCAAGCTCGAGTCGACTCCATT
                                                KpnI       XhoI SalI V  C  E  Y  Q  G  Q  S  S  D  L  P  Q  P  P  V  N  A  G  G  G  S  G  G
CGTTTGTGAATATCAAGGCCAATCGTCTGACCTGCCTCAACCTCCTGTCAATGCTGGCGGCGGCTCTGGTGG G  S  G  G  G  S  E  G  G  G  S  E  G  G  G  S  E  G  G  G  S  E  G  G
TGGTTCTGGTGGCGGCTCTGAGGGTGGTGGCTCTGAGGGTGGCGGTTCTGAGGGTGGCGGCTCTGAGGGAGG G  S  G  G  G  S  G  S  G  D  F  D  Y  E  K  M  A  N  A  N  K  G  A  M
CGGTTCCGGTGGTGGCTCTGGTTCCGGTGATTTTGATTATGAAAAGATGGCAAACGCTAATAAGGGGGCTAT T  E  N  A  D  E  N  A  L  Q  S  D  A  K  G  K  L  D  S  V  A  T  D  Y
GACCGAAAATGCCGATGAAAACGCGCTACAGTCAGACGCTAAAGGCAAACTTGATTCTGTCGCTACTGATTA
```

FIG. 9

```
 G   A   A   I   D   G   D   I   G   S   V   S   G   L   A   N   G   N   G   A   T   G   D   F
CGGTGCTGCTATCGATGGTTTCATTGGTGACGTTTCCGGCCTTGCTAATGGTAATGGTGCTACTGGTGATTT

A   G   S   N   S   Q   M   A   Q   V   G   D   G   D   N   S   P   L   M   N   N   F   R   Q
TGCTGGCTCTAATTCCCAAATGGCTCAAGTCGGTGACGGTGATAATTCACCTTTAATGAATAATTTCCGTCA

Y   L   P   S   L   P   Q   S   V   E   C   R   P   F   V   F   G   A   G   K   P   Y   E   F
ATATTTACCTTCCCTCCCTCAATCGGTTGAATGTCGCCCTTTTGTCTTTGGCGCTGGTAAACCATATGAATT

S   I   D   C   D   K   I   N   L   F   R   G   V   F   A   F   L   L   Y   V   A   T   F   M
TTCTATTGATTGTGACAAAATAAACTTATTCCGTGGTGTCTTTGCGTTTCTTTTATATGTTGCCACCTTTAT

Y   V   F   S   T   F   A   N   I   L   R   N   K   E   S   *
GTATGTATTTTCTACGTTTGCTAACATACTGCGTAATAAGGAGTCTTAATCATGCCAGTTCTTTTGGGTGCT
                                                                      Nhe1
       S   T   A   Q   H   D   E   A   V   D   N   K   F   N   K   E   Q   Q   N   A   F   Y   E
AGCTGTCGACTGCGCAACACGATGAAGCCGTAGACAACAAATTCAACAAAGAACAACAAAACGCGTTCTATG
    Sal1
       I   L   H   L   P   N   L   N   E   E   Q   R   N   A   F   I   Q   S   L   K   D   D   P   S

AGATCTTACATTTACCTAACTTAAACGAAGAACAACGAAACGCCTTCATCCAAAGTTTAAAAGATGACCCAA

Q   S   A   N   L   L   A   E   A   K   K   L   N   D   A   Q   A   P   K   V   D   N   K   F
GCCAAAGCGCTAACCTTTTAGCAGAAGCTAAAAAGCTAAATGATGCTCAGGCGCCGAAAGTAGACAACAAAT

N   K   E   Q   Q   N   A   F   Y   E   I   L   H   L   P   N   L   N   E   E   Q   R   N   A
TCAACAAAGAACAACAAAACGCGTTCTATGAGATCTTACATTTACCTAACTTAAACGAAGAACAACGAAACG

F   I   Q   S   L   K   D   D   P   S   Q   S   A   N   L   L   A   E   A   K   K   L   N   D
CCTTCATCCAAAGTTTAAAAGATGACCCAAGCCAAAGCGCTAACCTTTTAGCAGAAGCTAAAAAGCTAAATG

A   Q   A   P   K   V   D   A   N   *
ATGCTCAGGCGCCGAAAGTAGACGCGAATTAGCTGGGAATTAATTC
```

ANTIBODY LIBRARY

TECHNICAL FIELD

The present invention relates to an antibody library comprising DNAs encoding antibody variable domains.

BACKGROUND ART

The animal body has the ability of producing antibodies specifically recognizing and binding to various structures (epitopes) on the surfaces of various foreign agents invading into body fluids. The size of antibody repertoire (the total number of antibody types having distinct amino acid sequences binding to different types of antigens) of an animal individual has been estimated to be approximately 1 to 100 millions. The enormously large antibody repertoire is owing to DNA rearrangements of heavy chain VH-D-JH and light chain VL-JL on the antibody locus during differentiation of bone marrow stem cells into antibody-producing B lymphocytes. This event of DNA rearrangement occurs independently in each B cell. Thus, a single B cell that has a pair of VH-D-JH and VL-JL genes produces only a single type of antibody. However, a collection of entire B cells in an individual can produce various types of antibodies.

The techniques of antiserum preparation and monoclonal antibody preparation by using cell fusion, both of which have been utilized in the prior art, are based on the antibody-producing mechanism of animal body. Specifically, an antigen substance is injected in combination with an adjuvant into an animal (rabbit, goat, mouse, etc.) several times at a certain intervals of time. When the animal immune system recognizes the substance as a foreign one, a B cell that expresses an antibody binding to the antigen substance is stimulated for growth and differentiation, and thus a large quantity of the antibody is initiated to be secreted into the body fluid. Since there may be various structures on the surface of an antigen substance, even if it is a purified antigen, actually, the secreted antibody binding to the antigen is not a single type but a mixture of various types of antibodies. A serum containing such an antibody mixture (antiserum) is called "polyclonal antibody". Polyclonal antibodies have been used as useful reagents for research. However, polyclonal antibodies which are reactive to their target antigen substances are often cross-reactive to some molecules having partly similar structures to the target antigen molecules. Such cross reactivity has been problematic, when a polyclonal antibody is used as a reagent for detecting an antigen.

The cell fusion technology was established and changed the situation completely. There are many B lymphocytes producing antibodies binding to an antigen substance in the spleen in an animal immunized with the antigen. However, it is difficult to culture and keep such cells alive permanently in vitro. Then, an idea was conceived that antibody-producing cells, which proliferate permanently, could be established by preparing hybrid cells obtained by fusing cells of a tumor cell line and antibody-producing cells; such a method was established eventually. Since a fusion cell line (hybridoma) thus established is derived from a single antibody-producing cell and a single tumor cell, the antibody produced by the cell consist of a single type antibody; thus, the antibody is called "monoclonal antibody". This technology was established by Köhler and Milstein in 1975. A monoclonal antibody is a collection of homologous antibody molecules. Thus, monoclonal antibodies have been used as highly specific antibodies with less cross-reactivity. However, it has been pointed out that this method has the following problems that:

(1) it is required to prepare a large amount of purified sample of antigen substance;
(2) the substance must be antigenic in an animal to be immunized with it; and
(3) a great expenditure of time and effort is required to establish a monoclonal antibody.

An enormous number of useful antibodies have been provided by using the technologies for producing polyclonal and monoclonal antibodies, giving proof of the usefulness of the technologies. However, it is also true that there remain many difficult problems to be solved with respect to these methods. For example, these methods cannot meet the demand of preparation of antibodies against various antigens in a short time or of selectively preparing antibodies binding specifically to epitopes having special structures. It has been awaited to establish a method for preparing an antibody library comprising various antibody molecules, which ensures to isolate desired antibodies in a short time. Theoretically, the number of antibody types in such an antibody library must be comparable to the size of antibody repertoire in the animal body. Actually, however, it is impossible to prepare such an enormous library from animal cells. Monoclonal antibody preparation is nothing but screening of a library of antibody-producing cells derived from the animal body to obtain antibodies having desired reactivity. However, the repertoire in the library is greatly reduced during cell fusion or other processes.

Then, a method has been proposed, which comprises an *E. coli* expression system for antibody genes. Better et al., and Skerra and Plukthun have succeeded for the first time in expressing antibodies having antigen-binding activity in *E. coli* (Better, M., Chang, C. P., Robinson, R. R., Horwitz, A. H., Science 1988, 240:4855 1041-3; Skerra, A., Plukthun, A., Science 1988, 240:4855 1038-41). They attached a sequence serving as a secretory signal in *E. coli* to the N-terminus of antibody; thus, Fab-type and Fv-type antibodies were successfully produced and secreted by *E. coli*.

Further, immediately after being established in 1988, the PCR technology was utilized to amplify genes encoding antibody variable domains. Primers sequences to amplify all types of VHDJH and VLJL genes expressed in the animal body (particularly, human) were proposed (Orlandi, R. et al., Proc. Natl. Acad. Sci. USA. 1989, 86:10 3833-7; Sastry, L. et al., Proc. Natl. Acad. Sci. USA. 1989, 86:15 5728-32). Then, vectors for producing antibodies in *E. coli* were constructed by using antibody genes amplified with theses primers (Huse, W. D. et al., Science 1989, 246:4935 1275-81; Ward, G. E. et al., J. Clin. Microbiol. 1989, 27:12 2717-23). At this stage, the repertoire size of antibody library was greatly increased. However, it was difficult to screen trace amounts of antibodies produced in *E. coli* using their antigen-binding activities as indices. Efficient screening awaited the application of the phage-display method to antibody library preparation.

The phage-display method was devised by Smith in 1985 (Smith, G. P., Science 1985, 228:4075 1315-7); the method comprises using filamentous bacteriophage, such as M13 phage, containing single-stranded circular DNA. The phage particle comprises cp8 protein that is a major protein of the phage particle, enveloping its DNA, and five molecules of cp3 protein functioning at the time of phage infection to *E. coli*. In the phage-display system, a fusion gene is constructed to encode a polypeptide linked to the protein cp3 or cp8, and the fusion protein is expressed on the surface of phage particle. Such a phage particle carrying the protein with binding activity on the surface can be enriched based on the binding activity to its ligand. This method for enriching DNA of interest is called "panning". Enriched phages contain DNA encoding the protein having desired binding activity in their particles. The use of such filamentous phages as described above allowed the establishment of a system where screening based on the binding activity and DNA cloning can be carried out with high efficiency (Published Japanese Translation of International Publication No. Hei 5-508076). A method using a filamentous phage library has been reported, where antibodies can be expressed as Fab-type molecules (Published Japanese Translation of International Publication No. Hei 6-506836). In this report, the method comprises fusing the variable region with cp3 or the like whose N-terminal portion has been deleted.

The phage-display system was used for producing antibodies; antibody consisting of the VH domain alone, or scFv-, Fv-, or Fab-type antibody was expressed as a fusion with cp3 or cp8. The phage antibody binding to an antigen also comprises the antibody-encoding gene. However, antibodies, which were isolated from the antibody library at the very beginning using the phage-display system, often had only lower antigen-binding affinity. A method comprising artificially introducing mutations into genes was proposed to enhance the binding activity. Winter et al. provided an antibody library, from which high-affinity antibodies can be obtained, which contained antibodies having the semi-artificial sequences which were prepared by inserting random sequences between all pairs of VH or VL gene and JH or JL gene isolated (Nissim, A., Winter, G. et al., EMBO J. 1994, 13:3 692-8). De Kruif et al. also prepared an antibody library based on essentially the same principle (de Kruif, J., Boel, E., Logtenberg, T., J. Mol. Biol. 1995, 248:1 97-105). Vaughan et al. produced a sufficiently large antibody repertoire by expanding the library size (Vaughan, T. J. et al., Nat. Biotechnol. 1996, 14:3 309-14). Such strategies were indeed successful with respect to some limited types of antigens. However, even with such strategies, the probability of isolating desired antibodies still remains unsatisfactorily low. For example, even with currently available techniques, it is impossible to construct a human antibody library from which desired antibodies can be isolated with a probability comparable to that in the isolation of desired monoclonal antibodies using mice. Thus, a library consisting of more variations of antibodies is demanded.

An in vitro system faithfully mimicking the human's antibody-producing process is ideal to isolate antibodies binding specifically to various antigens from an in vitro constructed library perfectly containing all, types of human antibodies. The antigen-binding moiety of an antibody is located within the complementarity determining regions (hereinafter abbreviated as "CDR"), I, II, and III (six regions in total) of the variable (V) domains at the N-terminal ends of both chains H and L. The total number of amino acid sequence variations of the CDRs (including length variations), can be assumed to reflect the antibody repertoire size.

With respect to the antibody repertoire, it is necessary to consider both "naïve repertoire" before antigen invasion into the body and "antibody maturation" after antigen invasion. The active antibody gene encoding an antibody is created via DNA rearrangement. There are two classes of light chains: λ chain and κ chain; the gene encoding its V domain consists of VL gene and JL gene. There are 36 types of Vλ genes and 7 types of Jλ genes for the λ chain. During differentiation into B cell, the VL-JL gene is created via DNA cleavage and rejoining in the vicinity of VL gene and JL gene of κ chain or λ chain for the light chain. In most cases (two third), the segment of amino acids at 1st to 96th is derived from the VL gene and another segment of amino acids at 97th to 110th from the JL gene. However, after DNA cleavage, an exonuclease digests short portions of the DNA ends to be ligated, and then V (D) J DNA recombinase (recombinases) rejoins the DNAs. This may result in differences of approximately ±3 amino acids in the size of the VL domain encoded by the VL-JL gene. In the light chain, CDR1 corresponds to amino acids at 24th to 34th; CDR2, amino acids at 50th to 56th; CDR3, amino acids at 89th to 97th. Thus, for the λ chain, the total number of variations due to their combinations can be calculated by; (the number of Vλ genes)×(the number of Jλ genes)×(the total number of gaps). However, the actual size of Vλ-Jλ gene repertoire is smaller than 200 at the highest estimate. Because the Jλ genes carry similar sequences to one another, and 67% of gaps at the junctions are constant and the remaining 27% or more fall within ±1. The situation with regard to the κ gene is similar to that with λ gene. The total number of V κ genes is 37; the total number of Jκ genes is 4. Thus, the size of Vκ-Jκ gene repertoire is also smaller than 200.

The diversity in the light chain variable region is relatively low, but the diversity in the heavy chain variable region considerably larger. CDR1 (amino acids at 31st to 35th) and CDR2 (amino acids at 50th to 65th) are encoded by any one of 36 types of VH genes, and consequently the variety in this region is not so large. However, CDR3 produces enormous variations. CDR3 is positioned between CDR1 and CDR 2 of the two chains H and L in the antigen-binding moiety of an antibody. Heavy chain CDR1, CDR 2, and CDR 3 comprise about 60% and the light chain comprises about 40% of the whole surface area of the antigen-binding moiety. With respect to the portion excluding heavy chain CDR3, the repertoire size is estimated by: the number of light chain variations (several hundreds at the maximal estimate)×the number of heavy chain CDR1 and 2 variations (36)=approx. 10,000. Heavy chain CDR3 is encoded by a separate gene, which is called "D gene"; there are 26 types of D gene variations. Two types of DNA rearranging events, namely D-JH recombination and VH-D recombination, produce VH-D-JH and thus the CDR3-encoding region is completed.

It should be noted that the DNA rearrangement comprises the following processes:
(1) DNA cleavage at positions immediately adjacent to the signal sequences in the vicinity of VH, D, and JH genes;
(2) Digestion of DNA at its terminal portions by exonuclease;
(3) Insertion of a random sequence (referred to as N) by terminal transferase; and
(4) DNA repair and ligation.

In the above-mentioned process (2), larger variations are produced for the heavy chain than for the light chain. Further, the presence of process (3) is a more notable difference; light chain rearrangement has no such process. Heavy chain CDR3 (corresponding to amino acids at 95th to 102nd) is a region located between cysteine at residue 92nd and tryptophan at residue 103rd. The length of the region is altered ranging from 5 to 20 amino acids or more, and the sequence is also highly diverse in the region. These specific features produce an enormous number of variations of CDR3, the sequence of which, in effect, is different in every B cell differentiated independently.

The DNA rearrangements of heavy chain VH-D-JH and light chain VL-JL in the antibody locus during B cell differentiation is independent of the presence of antigen. An entire population of antibodies produced by total B cells, each of which expresses a pair of VH-D-JH and VL-JL genes, is referred to as "naïve repertoire of antibody". After antigen invasion, cells expressing antibodies capable of binding to antigens are stimulated for growth and differentiation. While secreting antibodies, B cells are subjected to mutations frequently in the variable region gene (VH-D-JH, VL-JL) encoding the antibody. B cells producing antibodies whose binding affinity for antigens is increased by the introduced mutations survive as memory cells while secreting the antibodies of high performance. This process is referred to as "antibody maturation". The mutational event plays the most important role in this process. Any antigen specificity that is not originally present in the naïve antibody repertoire is never newly generated through the introduction of mutations. Accordingly, a mechanism, by which clones having antigen specificities that are absent in the naive repertoire should be eliminated, is required to construct an antibody library in vitro which mimics the in vivo process of antibody production.

Problems on preparing antibody libraries in vitro are listed below.

(1) After each antibody gene is expressed, for example, in *E. coli* on a large scale, the heavy chain and light chain variable domains of the gene products hold together to an antibody molecule though protein folding. Clones, whose gene products fail any of these processes and thus are incapable of forming the exact immunoglobulin conformation, are of no use.

(2) In vivo, a complex formed from a pair of heavy chain variable domain and light chain variable domain exhibits unique antigen specificity in each cell; in vitro, it is necessary to construct a library by combining separately prepared libraries for the populations of heavy chain variable domains and light chain variable domain. For example, when a B cell population contains 10,000 types of cells, theoretically, the entire variations can be covered by a library at least consisting of: (10,000 types of the heavy chain variable domains)×(10,000 types of the light chain variable domains)=100 millions in total. As the number of combinations is increased, the library size indeed becomes larger, but the percentage of clones of inactive antibodies is also increased in the library.

(3) When human blood is used as an antibody gene source, the expression profile of antibody genes of each person may have a significant bias depending on his/her immunological history.

All of the above-listed three problems are involved in the causes of biased library repertoire. Namely, these result in unfavorable gaps between the theoretical and actual numbers of cloned in a library: the number of types of functional phage antibodies in a library prepared actually is markedly reduced as compared with the number of theoretically estimated clones in such a library.

More specifically, a library may comprise clones whose distribution is highly biased when the immune response against a specific antigen is enhanced. Alternatively, an antibody library prepared may contain many clones encoding antibodies having only insufficient antigen-binding activity. For example, when 50% each of light chain variable region genes and heavy chain variable region genes encode active antibody molecules, the probability that a combination of the two domains produces an active antibody is only 25%.

Such libraries have many problems in addition to one that the actual repertoire size is far smaller than the theoretical size. For example, antibody molecules having only weak antigen-binding activity interfere with immunological reaction on screening. Specifically, antibody-antigen complex formation is an equilibrium reaction; when clones of minority population coexist with those of majority population, the majority may overwhelm the minority in spite of the difference in the antigen-binding affinity.

In addition, the presence of clones encoding inactive antibodies can be an obstacle in cloning. Namely, as the number of clones encoding inactive antibodies is larger, the probability that the population include clones proliferating very rapidly becomes greater. Such clones growing rapidly are preferentially selected during screening, and thus may cause a considerably high background.

A problem of previously reported libraries is that it is hard to estimate how many effective clones are actually present in the libraries. It is thus impossible to evaluate the efficiencies of library and screening.

DISCLOSURE OF THE INVENTION

An objective of the present invention is to provide an antibody library containing antibody molecules having functionally active conformation at a high rate. Another objective of the present invention is to provide such an antibody library, a method for producing the antibody library, and screening method using the antibody library. Still another objective of the present invention is to provide a method for isolating genes encoding immunoglobulin light chains ensuring antibody molecules having the functional active conformations.

The present inventors strenuously studied on factors obstructive to screening a known antibody repertoire for desired antibodies. Then, they conceived that the abundance ratio of antibody molecules having functionally active conformation in the repertoire is too small to isolate useful antibodies from antibody libraries known to those skilled in the art. Various ideas have been proposed to establish previous methods for producing antibody libraries known to those skilled in the art; the goal is to construct antibody libraries in vitro faithfully mimicking the in vivo antibody repertoire.

In some instances, methods even comprise introducing artificial mutations at random to increase the number of antibody variations. However, in most of such attempts, antibody molecules having functionally active conformation were indeed produced, but antibody molecules having only insufficient activity were also produced. Thus, an antibody library constructed according to any one of previous method has an antibody repertoire containing antibodies of no use in vivo and many inactive antibody molecules, which can result in unsuccessful screening for functionally active antibodies. For example, it is assumed that a library is prepared by combining independent $10^5$ clones for the light chain variable region gene with $10^9$ clones for the heavy chain variable region gene. The number of variations of heavy chain variable region gene is sufficiently large. However, when there are many inactive genes in the variations given for the light chain variable region gene, a part of variations for the heavy chain variable region gene are eliminated during screening because their products cannot acquire the activity as the immunoglobulin.

The living body has the mechanism of selective growth of clones producing antibodies having high reactivity as well as the mechanism of producing various types of antibody molecules at random. Not only the step of eliminating inactive antibodies but also the step of increasing antibody variations is required to precisely mimic the in vivo antibody repertoire in vitro.

In this background, the present inventors predicted that antibody isolation could be achieved more efficiently by increasing the abundance ratio of functional antibody molecules in the antibody library. To meet this goal, it is necessary to identify the cause of the generation of inactive antibody molecules in antibody libraries known to those skilled in the art. The present inventors focused on the role of the light chain in the maintenance of antibody activity. First, they established a method for screening for the light chain allowing the formation of functionally active conformation in an antibody molecule.

Further, the present inventors carefully analyzed the structures of the selected light chain variable region genes by the above-mentioned method, and then found that the use of only light chain variable region genes having limited structures enabled to construct an antibody library containing antibody molecules having functionally active conformation at a high rate; thus the present invention was completed. There may be the possibility that the size of antibody repertoire is reduced during the step of selecting light, chain variable region genes. However, the present inventors carefully analyzed the structures of the light chain variable region genes selected according to the selection method of the present invention, and then found that the number of structures of the light chains capable of forming functionally active conformation when combined with the heavy chains fell within a limited range. In the present invention, it was clarified that such structures of the light chains constituting functional antibody molecules could be included within a particular range of repertoire; the most striking feature of the present invention is thus the use of these light chain genes in library preparation. Namely, the present invention relates to a method, which comprises the steps described below, for preparing an immunoglobulin gene library, rgdp library based on this library, and a method for screening these libraries for genes encoding antibodies recognizing specific antigens. The present invention also provides a method, which comprises the steps described below, for selecting genes encoding light chains capable of re-holding functionally active conformation with the heavy chains.

[1] A method for preparing a gene library comprising combinations of light chain variable region genes and heavy chain variable region genes of immunoglobulin, the method comprising:

(a) selecting light chain variable region genes encoding light chain molecules capable of re-holding functionally active conformation with an expression product of the heavy chain variable region genes;

(b) constructing a gene library which is a collection of the light chain variable region genes obtainable in step (a); and (c) combining the library obtainable in step (b) with a library of genes encoding the heavy chain variable regions.

[2] The method according to [1], wherein libraries of heavy chain variable region genes which have been prepared separately for each VH family in step (c) are combined together in accordance with the in vivo ratio of the respective VH families.

[3] The method according to [1], wherein the gene libraries in step (c) are combined in a single vector.

[4] The method according to [1], wherein the method further comprises the following step:

(d) selecting clones expressing the heavy chains using, as an index, a labeled peptide fused with the heavy chain variable regions.

[5] A gene library that is obtainable by the method according to [1].

[6] A gene library comprising at least genes encoding light chain variable regions of immunoglobulin, wherein genes encoding light chain variable regions incapable of re-holding functionally active conformations with immunoglobulin heavy chain variable regions have been substantially eliminated from the gene library.

[7] The library according to [6], wherein the library has been combined with a library of genes encoding the heavy chain variable region.

[8] The library according to [7], wherein each VH-family gene library for heavy chain variable region contains clones enough to cover in vivo diversity.

[9] The library according to [6], wherein the genes constituting the library have been introduced into a host cell selected from the group consisting of bacterium, yeast, and plant cell.

[10] The library according to [6], wherein the genes constituting the library have been introduced into mammalian cells.

[11] The library according to [6], wherein at least a part of the genes constituting the library has been introduced into filamentous phages.

[12] The library according to [11], wherein fragments of the heavy chain variable region and light chain variable region encoded by the genes constituting the library are displayed on the surface of filamentous phages and re-hold a functionally active conformation.

[13] The library according to [12], wherein a gene encoding a labeled peptide has been fused with the heavy chain variable region.

[14] The library according to [6], wherein the immunoglobulin light chain variable region gene is derived from human.

[15] The library according to [14], wherein an immunoglobulin light chain hypervariable region comprises an amino acid sequence without cysteine residue.

[16] A rgdp library, wherein each clone constituting the gene library according to [5] includes an antibody protein encoded by the gene in the clone.

[17] An antibody library that comprises antibody proteins encoded by the genes in the respective clones constituting the gene library according to [5].

[18] A method for selecting genes encoding light chain variable region capable of re-holding functionally active conformation with the heavy chain variable region, the method comprising:

(a) obtaining one or more genes encoding the light chain variable region;

(b) obtaining a gene encoding the immunoglobulin heavy chain variable region, wherein it is confirmed that the heavy chain variable region re-holds functionally active conformation with the light chain variable region;

(c) selecting arbitrary one of the genes encoding light chain variable regions obtained in step (a), and translating the selected gene into a protein under a condition ensuring the re-holding of functionally active conformation of immunoglobulin with the heavy chain variable region encoded by the gene which has been obtained in step (b);

(d) detecting the formation of an antigen-binding moiety in the protein translated in step (c); and (e) selecting a gene encoding the light chain variable region constituting the protein in which the formation of an antigen-binding moiety has been detected.

[19] The method according to [18], wherein the method further comprises the following step:

(f) determining the nucleotide sequences of the light chain variable region genes, comparing the amino acid sequences encoded by the nucleotide sequences with each other, and eliminating genes encoding identical amino acid sequences and genes encoding deleted amino acid sequences.

[20] The method according to [18], which comprises expressing the light chain variable region of immunoglobulin on the surface of filamentous phage.

[21] The method according to [18], which comprises using, as a sample containing the light chain to be used in step (c), the culture supernatant of a host microorganism infected with phagemid into which a gene encoding the light chain variable region of immunoglobulin and a gene encoding the heavy chain variable region have been inserted.

[22] A method for detecting an immunoglobulin variable region that binds to a particular antigen, the method comprising:
(a) contacting the antigen with the library according to [5] or [7] or with an expression product of the library under a suitable condition for antigen-antibody reaction; and
(b) detecting the binding between the antigen and the immunoglobulin variable region.

[23] The method according to [22], wherein the library is the library according to [12].

[24] A method for isolating a immunoglobulin variable region that binds to a particular antigen, the method further comprising carrying out the following step after practicing the method according to [22]:
(c) selecting a clone expressing the immunoglobulin variable region which binds to the above-mentioned antigen.

[25] The method according to [24], wherein the method further comprises the following steps:
(d) preparing a secondary library by amplifying phage clones selected in step (c); and
(e) repeating steps (a) to (d) for the secondary library until the recovery rate of clones selected in step (c) is elevated.

[26] A clone or immunoglobulin fragment isolated by the method according to [24], or a gene encoding the same.

[27] A polynucleotide comprising any one of the nucleotide sequences of SEQ ID NOs: 61 to 78.

[28] A protein comprising any one of the amino acid sequences of SEQ ID NOs: 79 to 96.

[29] A kit for preparing an antibody library, the kit comprising the following:
(a) a light chain variable region gene library from which genes encoding light chain variable regions incapable of re-holding functionally active conformation with heavy chain variable regions have been substantially eliminated; and
(b) a set of primers with which the genes encoding the heavy chain variable region can be amplified.

[30] A method for preparing an antibody library, the method comprising:
(a) introducing a gene encoding a region containing at least a variable region of immunoglobulin into phagemid;
(b) infecting a host microorganism with the phagemid obtained in step (a); and
(c) recovering, as an antibody library, the culture supernatant of the host microorganism of step (b) without infecting helper phage.

In addition, the present invention relates to a method for preparing antibodies recognizing the pathogens described below.

[31] The method according to [24], wherein the antigen is an antigen derived from a pathogen.

[32] A method for preparing an antibody having activity of neutralizing a pathogen, the method further comprising carrying out the following step (f) after practicing the method according to [24]:
(f) evaluating an antibody variable region selected in step (c) for the activity of neutralizing the pathogen and selecting an antibody variable region having neutralizing activity.

[33] The method according to [31], wherein the antigen derived from a pathogen is an antigen selected from the group consisting of influenza virus HA antigen, diphtheria toxin, tetanus toxin, and varicella virus-derived glycoprotein.

[34] The method according to [31], wherein the following step (a') is practiced before step (a):

(a') contacting the library with an antigen for absorption and removing antibodies bound to the antigen for absorption from the library;
wherein the antigen for absorption refers to an antigen which derived from the same pathogen from which the above-mentioned antigen is derived and antibodies reactive to which is undesired to be isolated.

[35] Use of the library according to [12] for preparing a neutralizing antibody against a pathogen.

As used herein, "immunoglobulin" refers to every type of immunoglobulin molecule consisting of heavy chain and light chain regardless of types of antibody class and animal species. The "immunoglobulin" also includes a fragment consisting of a domain capable of binding to an antigen and a chimeric antibody which is composed of multiple immunoglobulin domains derived from two or more animal species. In general, mammalian genes encoding the heavy chain variable region have been categorized into several VH families based on the structural features of the gene. For example, the human genes have been categorized into 7 families of VH1 to VH7. Members of the respective families contain nucleotide sequences highly conserved between the families. Based on the highly conserved sequences, PCR primers have been designed to amplify the members of each family. Like the heavy chains, the light chain variable domains can be categorized into several families based on the structural features.

A gene encoding the heavy chain variable region is consists of three classes of genes, namely V (variable), D (diversity), and J (junction). Each gene class V, D, or J comprises multiple genes; random combinations of these genes and introduction of mutations result in the antibody diversity. On the other hand, the light chain variable region consists of two classes of genes V and J. Combinations of multiple gene classes and introduction of mutations results in the diversity of the light chain variable region as well as the heavy chain variable region.

The term "library" is used herein, which refers to a collection comprising a repertoire of various components. Gene library, antibody library, and phage library are composed of genes, antibody molecules, and phages or phagemids, respectively. When an antibody gene in a phage genome is expressed on the surface of phage particle, such a gene library is an antibody library. However, as used herein, the term "phage library" also refers to a library of phage on which antibody molecules are not expressed. Specifically, cells of host microorganism infected with phagemid and lysogenized phages containing a genome carrying genes encoding the antibody variable region are also referred to as "phage library".

Further, the term "rgdp library" (replicable genetic display package library) is used herein. The rgdp library refers to a library comprising genes and the expression products of the genes displayed on the surface. When members of the above-mentioned phage library express antibody proteins on the surface of phage particles, the library is an rgdp library. Such rgdp libraries include a library comprising transformed cells expressing foreign proteins on their surface or ribosomes in addition to the phage library.

Further, the term "conformation" is used herein. As described above, immunoglobulin is a complex formed by holding of heavy chain and light chain. The conformation refers to the resulting structure of the complex through the heavy chain-light chain association. Basically, the conformation is established by disulfide bonding in the constant region. However, such an immunoglobulin does not always acquire antigen-binding activity. In the present invention, when a certain immunoglobulin has antigen-binding activity, one can state that the conformation of the immunoglobulin is functionally active. When a heavy chain which forms a functionally active conformation in combination with a certain light chain forms a functionally active conformation in combination with another light chain, then the association of the two is particularly referred to as "re-holding". Another light chain which constitutes re-holding includes a light chain isolated as a separate clone from an identical cell. Further, as used herein, "re-holding of conformation" basically refers to the re-holding of a region required for the binding of immunoglobulin to an antigen. Thus, it is assumed that the functionally active conformation is re-holded when the molecular structure in the variable region is re-holded as an immunoglobulin molecule regardless of the presence of constant region. Further, it is assumed herein that the functionally active conformation is formed when the re-holding is achieved in the variable region, even if artificial nucleotide sequences have been inserted in the genes encoding the light chain and heavy chain or even when genes encoding phage proteins have been fused with the immunoglobulin genes. More specifically, as used herein, the term "re-holding of molecular structure" equivalently means that the heavy chain variable domain and light chain variable domain constitute the immunoglobulin variable domain via disulfide bonding in the constant region, for example, when the genes encoding the heavy chain variable region and light chain variable region are translated to separate proteins.

On the other hand, there are antibody molecules in each of which the heavy chain and light chain have originally been linked together via an artificial linker, such as single chain Fv antibody (scFv). In such special types of antibodies, their conformations are established via not disulfide bonds but peptide bonds in some cases. Thus, the conformation of scFv antibody can be re-holded not through the constant region.

Firstly, the present invention relates to a method for preparing a gene library, which comprises selecting genes encoding light chains capable of re-holding functionally active immunoglobulin molecules and combining such a light chain variable region gene with a library of genes encoding heavy chains. The selection of light chain variable region genes of the present invention can be achieved by the steps described below. Specifically, the present invention relates to a method for selecting genes encoding light chains that allows re-holding functionally active conformation when combined with a heavy chain, which comprises the following steps:

(a) obtaining one or more genes encoding the light chain variable region;

(b) obtaining a gene encoding the immunoglobulin heavy chain variable region that has been confirmed to re-hold a functionally active conformation when combined with the light chain variable domain;

(c) selecting arbitrary one of the genes encoding the light chain variable region obtained in step (a), and translating the same into the protein under a condition ensuring the re-holding of functionally active conformation of immunoglobulin, when combined with the gene encoding the heavy chain variable region which has been obtained in step (b);

(d) detecting the formation of antigen-binding moiety in the protein translated in step (c); and (e) selecting a gene encoding the light chain variable domain constituting the protein whose antigen-binding moiety has been detected to be formed.

In the present invention, the light chain variable region or heavy chain variable region may be an arbitrary region comprising at least a portion required for antigen binding. In other words, an arbitrary region containing a region comprising three CDRs and the frame (FR) containing the same can be used as a variable region of the present invention. Accordingly, for example, a fragment containing the constant region can also be used as a variable region of the present invention, as far as it contains the region required for antigen-binding. Fab and Fab', which are often used as antibody variable domains, are names originally provided for fragments obtained by enzymatic digestion of immunoglobulin. As used herein, "Fab" is construed not to be a term to limitedly specify the variable region.

A light chain variable region gene, which is a target in the method of the present invention for selecting light chain variable region genes, can be obtained from an arbitrary antibody-producing cell. Such antibody-producing cells include, for example, peripheral blood lymphocyte and splenocyte. RT-PCR can be used advantageously to isolate light chain variable region genes. For example, primers that can be used for amplifying the human VLJL gene, have been disclosed (Published Japanese Translation of International Publication No. Hei 3-502801; or Published Japanese Translation of International Publication No. Hei 4-500607). In addition, such primers are also publicized on the homepage of MRC Corporation ("V-base"). Genes encoding the light chain variable region to be used in step (a) can thus be obtained by PCR using these primers. The genes obtained are used in step (c).

Then, genes encoding immunoglobulin heavy chain variable domains that have been confirmed to allow the re-holding of, functionally active conformation when combined with a light chain variable domain are isolated in step (b). The heavy chain variable region to be isolated in this step may have arbitrary antigen-binding specificity or the like, as far as it is derived from the same animal species from which the light chain variable region is obtained in step (a) and allows the re-holding of functionally active conformation in combination with the light chain variable region. A gene encoding such a heavy chain variable domain can be obtained, for example, from a gene encoding an immunoglobulin molecule that has been demonstrated to exhibit the activity as an antibody. It is preferable that a heavy chain variable domain to be used in step (b) should be prepared as one that can re-hold with κ chain or λ chain. It is preferred to select a heavy chain variable region with the highest efficiency by practically testing the efficiency of holding with the light chain. For example, in Example described below, when various clones for the heavy chain were evaluated for the efficiency of holding with the light chain, then VH3-4 having the following primary structure showed the highest efficiency of holding; VH3-4 (SEQ ID NO: 1) was thus selected, and has the following primary structure.

FR1: EVQLVESGGGLVQPGRSLRLSCAASGFTFD
CDR1: DYAMH
FR2: WVRQAPGKGLEWVS
CDR2: GISWNSGSIGYADSVKG
FR3: RFTISRDNAKNSLYLQMNSLRAEDTALYYCAK
CDR3: GPSGSFDAFDI
FR4: WGQGTTVTVSS

Then, arbitrary one of the genes encoding the light chain variable region obtained in step (a) and the gene encoding the heavy chain variable region obtained in step (b) are both translated into proteins under a condition ensuring the re-holding of functionally active immunoglobulin conformation in step (c). Since genes encoding the heavy chain variable domains capable of re-holding a functionally active conformation have been selected in step (b), all the molecules allowing the re-holding of the conformation for the variable region of immunoglobulin molecule in step of (c) can be assumed to have functionally active conformations. As far as the above-motioned immunoglobulin molecule contains the essential portion for the antigen binding of immunoglobulin, any type of molecular organization is allowable for the above-motioned immunoglobulin molecule. Thus, regardless of the presence of constant domain, the molecule can be assumed to be a re-holded immunoglobulin molecule when having the re-holded antigen-binding moiety.

The "condition ensuring the re-holding of immunoglobulin" in step (c) refers to a condition under which disulfide bonds enable holding between the heavy chain variable domain and light chain variable domain. More specifically, for example, the in vivo reducing environment (e.g., in E. coli periplasm) as described above with respect to the expression of Fab protein is a condition ensuring the re-holding of immunoglobulin. A reducing microenvironment required for the acquisition of the antibody conformation can also be provided by organelle such as endoplasmic reticulum in cells derived from mammals including human. Further, in some cases, such reducing environments are not required for re-holding immunoglobulin, when an antibody consists of the heavy chain and light chain variable domains linked together via an artificial amino acid sequence (linker), e.g., an scFv-type antibody.

Phages that express foreign genes on the surface can be used advantageously to express the light chain variable domain and heavy chain variable domain in step (c). For example, filamentous phages can express a fusion protein on the surface, which comprises a protein encoded by a foreign gene and a phage protein such as cp3 or cp8.

Typical phage library screening comprises the step of recovering phage particles. Thus, for example, when phagemid into which a foreign gene has been inserted, is infected, phage particles can be recovered by infecting helper phage. On the other hand, the present inventors have found that when E. coli infected with a phagemid containing, as an insert, the Fab gene, which is fused with the cp3 gene, is cultured without adding helper phage, the fusion protein of Fab and cp3 is secreted into the culture supernatant. Only a trace amount of the fusion protein of Fab and cp3 secreted from the E. coli infected with the phagemid was detected even after 20-hour culture, but it was enough for practicing the selection method for the light chain according to the present invention. Thus, samples to be used in the method for selecting for the light chain variable region gene according to the present invention may include culture supernatants of host microorganisms infected with such a phagemid. This method which does not require the step of recovering phage particles by infecting helper phage comprises only a very simple experimental procedure. A vector containing an operative promoter in a host microorganism and a signal sequence is used to prepare, as screening samples, culture supernatants of a host microorganism infected with the phagemid according to the method of the present invention. For example, a phagemid vector of filamentous phage, into which the pelB sequence or the like has been inserted as a signal sequence, can be used, when E. coli is used as the host.

The immunoglobulin variable region is structurally formed, when a light chain variable domain allows the re-holding of the functionally active conformation in combination with a heavy chain variable domain. The type of light chain variable region to be selected can be identified through detecting such structural formation of the variable domain. The formation of variable domain can be detected, for example, by using the principle of immunoassay. Specifically, the light chain variable domain is trapped on a plate, on which an antibody against the κ chain (or λ chain) has been immobilized, by adding a sample containing expression products of the heavy chain variable region gene and light chain variable region gene to the plate coated with the antibody. When the heavy chain variable domain is associated with the light chain variable domain, the heavy chain variable domain, along with the light chain variable domain, must be trapped on a plate. A labeled antibody against the heavy chain or Fab is then added to the plate. Only when the two types of molecules are associated together, the labeled antibody is trapped on the plate. After incubation for a convenient period, the plate is washed; a light chain variable domain re-holding the functionally active conformation can be identified by detecting the labeled antibody. The labeled antibody and the immobilized antibody can also be used in the inverse combination. Alternatively, it is possible that the heavy chain variable domain is pre-biotinylated, and then the detection is carried out using labeled avidin. As described above, the inventors have revealed that culture supernatants of E. coli cells infected with phagemid can be used as samples in this detection method.

Such a light chain variable domain that has been confirmed to be associated with the heavy chain variable domain by the method as described above can be selected as a light chain variable domain that allows the re-holding of the functionally active conformation in combination with the heavy chain variable domain. When a phage library contains genes encoding the light chain variable region, genes of the light chain variable region can be selected by recovering the phage particles.

Such light chain variable region genes obtained by the steps as described above not only allow the re-holding with the heavy chain variable domain but also are demonstrated to be expressed in the expression system used in the screening. For example, when a phage expression system is used, light chain variable region genes whose expression levels in E. coli cells are high enough are selected. Thus, genes whose expression levels in E. coli cells are too low can be eliminated, even if they are expressed in mammalian cells. Thus, the method of the present invention for selecting light chain variable region genes has such a new merit. On the contrary, with the conventional techniques for preparing antibody libraries, the light chains are selected without such a selection step, and therefore it is impossible to avoid the contamination of light chain genes whose expression levels are insufficiently lower.

Selected genes encoding the light chain variable region can be used without any modification for preparing gene libraries of the present invention. However, at this stage, the selected genes encoding the light chain variable region may have redundancy. Thus, it is preferred to remove redundant genes through analyzing the structures of the light chain variable region genes before preparing the gene library using them. Such redundant genes can be removed, for example, by the following method.

First, before or after the above-mentioned step (d), the nucleotide sequences of the light chain variable region genes are determined and the amino acid sequences encoded by the nucleotide sequences are deduced. The deduced amino acid sequences are compared with one another, and then genes encoding identical amino acid sequences are removed. It is preferred to additionally carry out deletion check at this stage. For this purpose, genes having reading frame shifts are removed after the nucleotide sequences are determined.

In practice, the selection and isolation of genes can be carried out by grouping genes showing similarity into a single category, and selecting a representative sequence from each group. The selection should be carried out so as to cover all the selected genes without bias and not to alter the distribution of gaps at the VL-JL junction in the population of naturally occurring antibodies. In practice, light chain variable region genes for known antibody molecules were selected from a gene database, and then the distribution was determined based on the result obtained by analyzing gaps at the junction. Table 1 shows a result of analysis for the number of amino acids at the V-J junction (the amino acid sequence 91-96).

TABLE 1

| Size | Group | | | | | Total | Reported |
| --- | --- | --- | --- | --- | --- | --- | --- |
| | 1 | 2 | 3 | 4 | 5 | | |
| 1 | 0 | 0 | 0 | 0 | 0 | 0 | 1 (0.2%) |
| 2 | 0 | 0 | 1 | 0 | 0 | 1 (1.0%) | 2 (0.3%) |
| 3 | 0 | 0 | 0 | 0 | 0 | 0 | 2 (0.3%) |
| 4 | 0 | 0 | 0 | 0 | 0 | 0 | 1 (0.2%) |
| 5 | 2 | 1 | 3 | 1 | 1 | 8 (7.9%) | 54 (8.5%) |
| 6 | 24 | 17 | 15 | 9 | 4 | 69 (68.3%) | 427 (67.5%) |
| 7 | 3 | 1 | 13 | 1 | 1 | 18 (17.8%) | 119 (18.8%) |
| 8 | 2 | 1 | 1 | 0 | 0 | 0 | 1 (0.2%) |
| 11 | 0 | 0 | 1 | 0 | 0 | 1 (1.0%) | 0 |
| Total | 31 | 20 | 33 | 11 | 5 | 101 | 633 |

Group: Vκ family No. Size: the number of amino acids in the region of amino acid sequence 91-96

After general consideration of the results obtained as described above, according to the analysis result by the present inventors, the repertoire size of representative light chain variable region sequences, which were selected by the selection method, is 101 for the κ chain, or similarly 99 for the λ chain in the case of human immunoglobulin.

Thus, the repertoire size of the representative light chain variable region sequences of functional human immunoglobulin was revealed to be 200 at most. However, the repertoire size is not limited to the estimate of about 100 by the present inventors. Specifically, for example, when one intends to select human light chain variable region genes according to the selection method of the present invention, the number of light chain variable region genes to be selected is not always 100. The most important thing is that light chain genes selected by practicing the selection method described herein based on the obtained amino acid sequences are used in the subsequent steps.

The VL genes of phage antibodies obtained by screening were categorized herein into several groups. The result is shown in FIG. 1. The distribution of VL gene has been found to have a bias toward some particular genes. This result demonstrates that a high-quality library containing functional active immunoglobulins can be prepared by selecting a set containing, in a high percentage, many light chains allowing the re-holding of the immunoglobulin conformation.

In this step, it is preferred that as many amino acid sequences as possible are analyzed to mimic the in vivo antibody diversity.

In the human genome, genes constituting the light chain include 36 types of Vλ, 7 types of Jλ, 37 types of Vκ, and 4 types of Jκ. Since a combination of V gene and J gene produces a light chain gene, a simple estimate is as follows: summation of (36×7=252) and (37×4=148), namely 400 types of vitiations. In addition, mutational events occur during joining genes, and thus further increase the number of amino acid variations at the junction. Specifically, the event specific to antibody gene rearrangement as described above produces variations of about ±1 amino acid in average (about ±5 amino acid at most). After some dispensable genes are further eliminated from the combinations, the repertoire is completed in an individual. In addition, there are minor variations in the genes in each individual (which is referred to as "polymorphism"). It is practically impossible to study the whole types of antibody genes of the entire human beings, but the total number has been estimated to be 1,000. These findings shows that, when a human individual can produce a set of antibodies corresponding to all types of antigens, the repertoire for the light chain variable region gene can be reproduced successfully by analyzing theoretically preferably about 400 to 1,000 types of amino acid sequences by the method of the present invention.

The repertoire size for the human light chain (200 types) was estimated by the present inventors based on the result obtained by analyzing approximately 1,000 types of amino acid sequences. Thus, theoretically, it can be assumed that the light chain variable region genes are selected so as to allow the re-holding of functionally active conformation in every antibody set. The present invention has experimentally proven that the repertoire size of light chain variable region genes determined to be 200 types according to the present invention is large enough to mimic in vitro the in vivo antibody diversity. However, there is a possibility that the repertoire size is determined to be larger by analyzing amino acid sequences deduced from much more nucleotide sequences.

Then, the repertoire size of the library of light chain variable region genes selected according to the present invention can be increased by combining the library with another light chain gene library. Namely, a library of light chain variable region genes (referred to as VL library) is prepared by using a non-biased collection of the entire light chain genes without selection by the same method used for the heavy chain. A library whose shortage has been supplied by combining the VL library prepared as describe above with the library (referred to as KL200 library) comprising only 200 types of light chain variable region genes. The respective libraries have the characteristics described below.

KL200 library has been confirmed to comprise the light chains allowing the re-holding of the functionally active conformation when combined with the heavy chain. However, there is a possibility that light chains required for clones having particular specificities have been excluded from the library because of the limited number.

VL library covers all of the clones required, because the number of independent clones in it is $10^9$. However, the level of expression and the rate of conformation formation with the heavy chain are lower than those of KL200 library.

Basically, genes can be selected arbitrarily from each group classified based on the analysis result of amino acid sequences according to the present invention. Thus, it is not quite significant to identify the structures of genes encoding light chains allowing the re-holding of functionally active conformation in combination with the heavy chain. The most important is to practice the selection step for the light chains that allows the re-holding of functionally active conformation in combination with the heavy chain according to the selection method. By the procedure, a human light chain variable region gene library can be prepared from a library comprising 101 types of κ chain genes and another library comprising 99 types of λ chain genes.

As described below, when combined with genes encoding the heavy chain variable region, the library of the light chain variable region genes selected according to the present invention provides an immunoglobulin gene library. Thus, the library of light chain variable region genes selected according to the present invention can be used to prepare an immunoglobulin gene library. Specifically, the present invention relates to a gene library consisting of at least genes encoding the light chain variable region of immunoglobulin, in which genes encoding the light chain variable domains incapable of re-holding functionally active conformation when combined with the immunoglobulin heavy chain have been substantially eliminated.

In the present invention, the genes encoding the light chain variable region incapable of re-holding functionally active conformation when combined with the immunoglobulin heavy chain can be eliminated by the selection method for the light chain variable region as described above. A gene encoding the light chain variable region incapable of re-holding-functionally active conformation when combined with the immunoglobulin heavy chain is herein referred to as "defective gene". In the present invention, a library where defective genes have been substantially excluded does not refer to a library from which defective genes have been eliminated completely. For example, a library where defective genes have been contaminated can be assumed to be a library where defective genes have been substantially excluded, when the population of contaminated genes falls within a range where the antibody screening based on immunological reaction is not prevented.

The "range where the antibody screening based on immunological reaction is not prevented" means that the percent population of defective genes in an antibody library ranges, for example, of 0 to 50%, preferably 0 to 25%. As a matter of course, the smaller the population of defective genes, the higher the screening efficiency and the lower the risk for the loss of useful clones during the screening step. However, the inventors prepared trial libraries and tested the screening efficiency; a VL library in which 50% of the genes are assumed to be defective genes was combined at various ratios with a KL200 library, from which defective genes had been eliminated completely; then, it was confirmed that effective screening was secured up to 1:1 ratio. This fact shows that defective genes can be assumed to be substantially excluded when the percent rate of defective genes is more preferably 25% or less.

A library consisting of only the light chains of the present invention is useful as material to be combined with a library of genes encoding the heavy chain variable region. Such a library includes, for example, a phage library in which a light chain library from which defective genes have been substantially excluded have been inserted into the gene encoding cp3 protein of phage, and the vector of which has a cloning site to insert the heavy chain variable region gene. Typically, methods for preparing phage libraries comprise inserting a foreign gene in the phagemid so that the phage could retain the infectivity to the host microorganism and packaging the phagemid into a phage particle by using helper phage. The phage library of the present invention can also be constructed by using a phagemid. Specifically, a cloning site, at which is to be used for inserting a gene encoding the above-mentioned light chain variable domain connected with a signal sequence and a gene encoding the heavy chain variable domain, is placed downstream of a promoter which is operative in the host. The cloning site for the heavy chain variable region gene advantageously contains a site recognizable by a restriction enzyme which digests genes of interest in a minimal frequency. The phage library of the present invention can be prepared not only using the phagemid but also using phage genome. The heavy chain variable region gene is synthesized by PCR using primers additionally containing cloning site, and then inserted into the phage library; thus a phage library for the expression of immunoglobulin variable region can be completed.

Alternatively, an *E. coli* strain that can express and secrete a light chain variable domain can be prepared by inserting a light chain library from which defective genes have been substantially eliminated into an *E. coli* expression vector and transforming *E. coli* cells with the light chain variable region library. Phage particles on which Fab has been re-folded on the surface can be prepared by infecting to *E. coli* the phages in which the heavy chain variable region genes obtained by PCR have been inserted. An antibody library containing desired antibodies can be prepared by selecting heavy chain variable region genes from a variety of individuals having different immunological histories.

A kit for preparing a phage library can be provided based on such a method. Such kits comprise a light chain gene library from which defective genes have been substantially excluded and primers for amplifying the heavy chain variable region genes. Users can prepare PCR products from a gene source having an immunological history, which can provide genes encoding desired antibodies, using primers ensuring the amplification of heavy chain variable region genes. For example, a library in which a population of antibodies recognizing tumor-associated antigens has been enriched can be obtained from a host affected with cancer.

A library of the present invention is prepared by using the light chain variable region genes selected as described above. Specifically, the present invention relates to a method for preparing a gene library comprising combinations of light chain variable region genes and heavy chain variable region genes of immunoglobulin, which comprises the following steps:

(a) selecting a light chain variable region genes encoding light chain molecules capable of re-holding functionally active conformation, in conjunction with expressed product of heavy chain variable region genes;

(b) constructing a gene library which is a collection of light chain variable region genes obtained in step (a); and (c) combining the library obtained in step (b) with a library of genes encoding the heavy chain variable region.

The selection for the light chain in step (a) is as described above. The library of step (b) can be prepared by collecting previously obtained genes encoding the light chain. When the light chain variable region genes are introduced in filamentous phage particles, a library can be obtained by recovering the phage particles amplified. Then, in step (c), the above-mentioned light chain gene library is combined with a heavy chain gene library. The heavy chain variable region genes can be obtained from antibody-producing cells such as peripheral blood lymphocytes and splenocytes by a method known to those skilled in the art. For example, there are seven VH families of VH1 to VH7 for human immunoglobulin.

Primers ensuring the amplification of respective genes belonging to each family are known to those skilled in the art (Campbell, M. J., Zelenetz, A. D., Levy, S. & Levy, R. (1992). Use of family-specific primers for PCR amplification of the human heavy chain variable gene repertoire. Mol. Immunol., 29, 193-203; in addition, such primers are publicized on the homepage of MRC Co. "V-base"). Thus, the heavy chain variable region genes can be amplified for each family by RT-PCR using such primers.

The heavy chain variable region genes obtained as amplification products can be converted to a gene library by inserting each gene into an appropriate vector. In this step, the library of the heavy chain variable region genes is prepared separately for each VH family; the respective libraries are combined together in accordance with the in vivo ratio of the respective families; thus, the gene library of the present invention can mimic the in vivo antibody repertoire. Specifically, for example, in human, the respective populations are roughly estimated to be at the following ratio. Mimicking the in vivo antibody repertoire can reduce the chance of losing desired clones during screening.

VH1: 25%
VH2: 6.6%
VH3: 40%
VH4: 19%
VH5: 5%
VH6: 3.8%
VH7: 1.2%

The preparation of heavy chain variable region genes is described below in more detail. Primers are designed for the respective seven VH families, and then RT-PCR is carried out using the primers in combination with a primer common to six types of JH genes. Primers that enable to amplify a wide range of genes of each human VH family are known to those skilled in the art (Marks J. D. et al., J. Mol. Biol. (1991) 222, 581-597; Campbell, M. J., Zelenetz, A. D., Levy, S. & Levy, R. (1992); Use of family-specific primers for PCR amplification of the human heavy chain variable gene repertoire. Mol. Immunol., 29, 193-203; in addition, such primers are publicized on the homepage of MRC Corporation, "V-base"). It should be confirmed that exact genes of each family are amplified corresponding to the primers used. Specifically, dozens of clones corresponding to bands of amplified products having the VHDJH structure are isolated from each family, and then their nucleotide sequences are determined to analyze which heavy chain variable region gene was amplified. When some genes are hardly amplified, extra primers are newly designed and added. For example, it has been reported that some new primers allow the amplification of genes that cannot be amplified by conventional primers.

When having the VHDJH structure in frame, each of such clones are inserted into an appropriate vector to analyze the expression level in $E. coli$, holding with a protein encoded by the light chain variable region gene, and folding. When any step is poorly achieved with some clones, then one should deduce the reason and estimate the percent population of such clones in the library.

The population of each immunoglobulin molecule in an individual depends on the immunological history. Thus, it is important to prepare heavy chain variable region genes from a wide variety of B cells so as to reflect as many immunological histories of individuals as possible. In practice, the number of types of gene source available for the heavy chain variable region genes should be increased, e.g., umbilical blood, tonsil, peripheral blood, bone marrow, etc.

Further, it is also important to prepare B cells from a naive B cell population which has no experience of contacting with immunogens (including autoantigens). Because clones recognizing self antigens are eliminated during the maturation period of immune system. Naive B cells are important to construct a gene library further containing a repertoire of antibodies against autoantigens. Such libraries are carefully combined so that the number of clones is proportional to the number lymphocytes. The VHDJH library eventually prepared should contain independent clones on the order of $10^9$ ($10^9$ to $10^{10}$).

The treatment has the significance as described below. The amino acid sequence constituting antigen-binding surface of an antibody is determined by the genes on the genome for light chain CDR1, CDR2, and CDR3, and heavy chain CDR1 and CDR2 (including evolutionary selection); the entire variations cover about 10,000 types. An enormous number of heavy chain CDR3 variations further increase the level of diversity. It is necessary that the antibody library contains the 10,000 variations as equally as possible and variations of heavy chain CDR3 (which is produced in a random process in each B cell of each individual) maximally. The above-mentioned method can meet this demand.

By the above-mentioned analyses, the present inventors found that the VH gene was not exactly expressed when a CDR contained cysteine residues. They also confirmed that 70% or more clones in the prepared heavy chain variable region library were successfully expressed, holded with the heavy chain variable region domain, and folded in $E. coli$.

Alternatively, the library can be characterized roughly by selecting a source for heavy chain variable region genes based on the immunological history. For example, the probability that immunoglobulin exhibiting high affinity for the pathogen is obtained is higher, when the person has a previous history of an infectious disease. When antibody-producing cells from a cancer patient are used as a source for the heavy chain variable region genes, immunoglobulins recognizing a tumor-associated antigen may be obtained.

Further, artificial mutations introduced into the VH genes can increase the number of variations in a library. A method, known to those skilled in the art, for introducing artificial mutations is error-prone PCR (Winter, G. et. al., Annu. Rev. Immunol., 12, 433-455, 1994). Since defective genes for light chain variable domain have been substantially excluded from the library of the present invention, the diversity of the heavy chain variable region gene directly contributes to the diversity of the library. Thus, such a library can attain a diversity of extremely high level simply by carrying out error-prone PCR which is known to those skilled in the art. The error-prone PCR can be practiced as follows.

The error-prone PCR is a method for introducing random point mutations. Specifically, one can utilize the following biochemical properties of DNA polymerase to be used in PCR.

(1) While typically Taq DNA polymerase is used in the presence of $Mg^{2+}$ ion, the fidelity of the enzyme for nucleotide incorporation is impaired in the presence of $Mn^{2+}$ ion.

(2) While typically the nucleotide monomers, dATP, dCTP, dTTP, and dGTP, are used at an equal concentration in PCR, their concentrations can be altered so as to ensure the introduction of mutations at a higher rate.

(3) dITP is also used in addition to the four types of nucleotide monomers. By Taq DNA polymerase, dITP is incorporated as inosine nucleotide into a DNA chain. No base pair is formed between an inosine residue and any of the four nucleotides; as PCR proceeds, at the position complementary to an inosine, any one of the five types of nucleotides can be incorporated at random.

Mutations can be introduced at random based on the synergistic effect of the above-mentioned three factors. Specifically, the reaction can be carried out under a condition, for example, of 7.5 mM $MgCl_2$, 0.5 mM $MnCl_2$, 0.2 mM dATP/dGTP, 1.0 mM dCTP/dTTP, 0.1 to 1.0 mM dITP. In practice, conditions, such as a concentration, are further adjusted to meet the experimental purpose. Reaction conditions such as temperature may be the same as used in typical PCR experiments.

Vectors known to those skilled in the art can be used for preparing a gene library of the present invention. Vectors that can be used in the present invention include, for example, a phage library containing the light chain variable region gene library prepared as described above. Specifically, a heavy chain variable region gene is inserted upstream of the light chain variable region gene in a phagemid (Iba, Y. et al., Gene 194 (1997) 35-46). A phage library in which the phages express the heavy chain variable region and light chain variable region at the same time on their surface can be used advantageously to practice the panning method (see below) using the antigen binding as an index.

Specifically, an rgdp library can be provided by preparing the gene library of the present invention as a phage library. The gene library of the present invention can be prepared as an rgdp library using a system where a foreign gene is expressed as a fusion protein with a ribosome protein or a protein constituting *E. coli* flagella as well as a phage protein.

A representative rgdp library is the phage library. A phage library based on the antibody library of the present invention can be prepared as described below. Phagemid or helper phage is generally used to express a foreign protein on phage surface. For example, phagemid vectors such as pTZ19R (Pharmacia) are commercially available. When a phagemid is used, the gene encoding a foreign protein to be expressed is ligated with a gene encoding phage protein cp3, cp8, or the like.

A phagemid can be amplified by infecting a host such as *E. coli* with it. However, phage particles cannot be recovered by only this treatment. In a word, the state after the treatment as described above is the same as that of a typical gene library. Superinfection of helper phage to the microorganism already infected with phagemid allows the display of the foreign protein, whose gene has been inserted in the phagemid, on the surface of phage particles. For example, phage particles for the phagemid vector pTZ19R can be recovered upon superinfection of helper phage M13K07. When the foreign protein is fused with cp3 protein derived from the phagemid used, the foreign protein is displayed on the surface of the resultant phage particles.

When a restriction enzyme site suitable for the cloning of an antibody gene has been introduced into a commercially available phagemid, the light chain variable region gene library of the present invention in combination with a heavy chain variable region gene library can be inserted into it. A method, which comprises introducing an appropriate restriction enzyme site into the phagemid vector pTZ19R and inserting an antibody gene library amplified by PCR into it, is known to those skilled in the art (Gene 194, 35-46, 1997). In Example described below, SfiI site and AscI site were introduced downstream of the signal sequence PelB into a phagemid vector. On the other hand, a primer having the same restriction enzyme site is used to amplify the light chain variable region gene. The amplification products obtained by PCR are inserted at the restriction enzyme site which has been pre-cleaved with the enzyme; the antibody variable region gene is thus placed downstream of PelB. The constructed phagemid vector encodes a antibody variable region protein fused with cp3 located further downstream (pFCAH9-E8d in FIG. 2).

The heavy chain variable region gene can also be inserted into an expression vector for a bacterial host. In this case, the heavy chain variable region gene can be expressed by transforming bacterial cells with the vector. A gene library of the present invention is finally completed by further infecting a phage library containing the light chain variable region gene to the transformed cells obtained. The vectors for *E. coli* transformation include pFK, etc. In cases where bacterial cells are transformed with the phages, when the heavy chain variable region gene has been inserted downstream of an appropriate secretory signal, the heavy chain variable region protein can be secreted into periplasm. pFK is a vector containing the secretory signal pelB.

Further, the library of the present invention can also be prepared by inserting the light chain variable region gene library prepared as described above and a library of heavy chain variable region genes into an expression vector for animal cells. Such vectors include pcDNAI, etc.

The nucleotide sequence encoding a label peptide can previously be fused to the 3' end of heavy chain variable region genes constituting the gene library of the present invention. Such label peptides include, for example, histidine tag (His× 6), myc-tag, HA-tag, etc. The histidine tag has metal ion-binding activity. When a heavy chain constituting the library of the present invention has been fused with the histidine tag, for example, phage particles expressing the heavy chain can be trapped in a nickel column. Clones expressing the heavy chain can be enriched and purified by washing off the particles of the phage and helper phage unbound to the nickel column.

The gene library of the present invention may be any type of antibody library. Specifically, such libraries include phage library, *E. coli* library, ribosome library, etc. The antibody library according to the present invention can be prepared by expressing the immunoglobulin genes in the clones constituting the antibody library according to the present invention and recovering the expression products. The present inventors have found that when *E. coli* infected with a phagemid containing, as an insert, the light chain variable region gene and heavy chain variable region gene fused with the cp3 gene, is cultured without adding helper phage for a long period, the fusion protein of Fab and cp3 is secreted into the culture supernatant from *E. coli*. The characteristics of antibody gene in a phagemid can readily be tested by utilizing this phenomenon. Further, each clone is analyzed to confirm whether the re-holding has been achieved between the light chain variable domain and heavy chain variable domain, and such analysis allows excluding clones failing the re-holding. The antibody library of the present invention can mimic the in vivo antibody population by this treatment.

The antibody library of the present invention can be used to screen for desired variable region genes through screening the antibody. With the antibody library of the present invention, without distributing the variable region gene library itself, one can provide only the antibody library to a third party who practices the screening for desired antibody. The present invention relates to a method for detecting antibodies having desired reactivity in the library of the present invention. The antibody reactivity can be evaluated by the antigen-binding activity. Specifically, desired antibodies can be detected using as an index the activity of binding to an antigen of interest by the following steps:

(a) contacting the antigen with the antibody library according to the present invention under a suitable condition for antigen-antibody reaction; and (b) detecting the binding between the antigen and the immunoglobulin variable domain.

Further, the present invention relates to a method for obtaining immunoglobulin variable domain binding to a specific antigen by using the library of the present invention. Firstly, the method of the present invention for detecting antibody variable domain comprises the step described below.

Further, the method of the present invention for obtaining immunoglobulin variable domain which binds to a particular antigen further comprises the following step (c) in addition to the above-mentioned steps (a) and (b):

(c) selecting a clone expressing the immunoglobulin variable domain which binds to the above-mentioned antigen.

The library to be used in step (a) can be a library that ensures the expression of both light chain variable domain and heavy chain variable domain, or an antibody library comprising the expression products from the former library. In a particularly useful library, fragments of the heavy chain and light chain encoded by the genes constituting the library are expressed on the surface of filamentous phage, and they are re-holding the functionally active conformation on the surface of phage particles. This type phage library serves as an rgdp library, and with this library, clones having desired reactivity can readily be enriched by the panning method. The panning method according to the present invention can be practiced as follows.

First, an antigen of interest is contacted with an rgdp library, and then clones bound to the antigen are recovered. After being amplified, the recovered clones are again contacted with the antigen of interest. Then, clones bound to the antigen are recovered. This cycle is further repeated. The amplification of clones is achieved by infecting E. coli cells with phage and recovering the phage particles. The variable domain having desired reactivity is enriched by repeating this step. In general, such screening based on the antigen-binding activity is repeated until the recovery rate of clone is markedly increased. The "recovery rate" used herein refers to a ratio of: (the number of recovered clones having the antigen-binding activity) to (the number of clones charged with an antigen-coated plate). When the recovery rate is markedly increased as compared with that of the previous round of screening, phage particles displaying the antibodies having desired reactivity are assumed to be enriched.

In addition, screening can be carried out by using an antibody library that comprises a collection of separately recovered expression products of the respective clones constituting a library. It is also possible to directly select immunoglobulin having desired reactivity by contacting the expression product of each clone with an antigen of interest. A desired clone for the variable region can be obtained by selecting a clone encoding immunoglobulin that has been detected to bind to an antigen.

In the present invention, any compound having epitopes can be used as an antigen to detect and obtain an antibody variable domain. It has been known that a wide variety of proteins, sugars, nucleic acids, organic compounds, and inorganic compounds have epitopes. These compounds may be derived from biological samples or synthesized artificially. Specifically, such compounds that can be used as antigens include those of animals and plants; microorganisms such as bacteria and fungi; cells and particles such as viral particles; proteins constituting them; sugar chains; lipids, etc. Further, various nonproteinous agents, hormones, vitamins, cytokines, chemokines, chemical substances causing environmental pollution, and others can be used as antigens in the present invention, when having epitopes.

Further, the whole antigen molecule that is a target of a desired antibody or a part of the antigen molecule may be used as an antigen. Unless otherwise specified, the antigen of the present invention also includes compounds comprising a partial structure of the antigen. For example, a high-specificity antibody can be obtained by using a partial antigen molecule containing an epitope comprising a specific structure of the antigen molecule.

Further, a complex of multiple molecules can be used as an antigen. Unless otherwise specified, the antigen of the present invention also includes a complex of multiple molecules. Using such a complex as an antigen, it is possible to obtain an antibody that can discriminate the complex from each monomeric molecule.

For example, an antibody molecule that can be used as a neutralizing antibody against a pathogen can be detected in the library of the present invention, which can be followed by isolation of the gene encoding the same from the library. In the present invention, the pathogen includes every pathogenic organism, and every substance derived form such an organism. More specifically, such organisms include virus, bacterium, fungus, mycoplasma, multi-cellular parasitic organism, etc. The pathogen of the present invention also includes toxins derived from microorganisms, animals, and plants. Thus, the pathogen of the present invention also includes toxins produced by *cholera vibrio* and enterohaemorrhagic *Escherichia coli*, etc. The pathogen of the present invention also includes biotoxin such as snake venom, bee toxin, etc. On the other hand, the neutralizing antibody of the present invention refers to an antibody having the activities of suppressing pathogenicity and infectivity of the pathogen.

The method of the present invention for detecting such a neutralizing antibody comprises detecting a clone expressing the immunoglobulin variable domain binding to the antigen by contacting the antigen derived from the pathogen with the library of the present invention. Further, the present invention provides a method for screening for a neutralizing antibody by selecting a clone expressing the variable domain binding to the antigen.

In the method of the present invention for screening for a neutralizing antibody, antibodies comprising the variable region having undesired reactivity can be removed from the antibody library by absorption. For example, it has been believed that antibodies against the HA antigen of influenza virus are effective to suppress the infectivity. On the other hand, among antibodies against the same influenza virus particles, antibodies against the nuclear protein (NP) have no virus-neutralizing activity. However, when the influenza virus particle is used as an antigen, anti-NP antibodies are often detected. As a result, screening efficiency for neutralizing antibodies may be impaired. In such cases, when anti-NP antibodies have been pre-absorbing, efficient detection of anti-HA antibodies can be achieved. Such anti-NP antibodies can be absorbed by contacting the library of the present invention with the NP antigen of influenza virus particles under a condition allowing the antigen-antibody reaction, and removing antibody variable region bound to NP antigen. Such antibodies against HA antigen can be prepared efficiently, for example, by using, as an index, the binding activity to purified HA antigen sample containing no NP antigen. However, the method comprising the step of pre-absorbing anti-NP antibodies can be used advantageously to confirm the reactivity of an antibody against virus particles having the original surface structure.

The genes obtained as described above, which encode immunoglobulin variable domains, and the immunoglobulin variable domains that are the expression products are within the scope of the present invention. The isolated immunoglobulin variable domains can be used for diagnosing and treating diseases. In particular, when the antibody is a human immunoglobulin, it can be administered into the human body. Specifically, such an antibody can be used for diagnosing and treating various infectious diseases, tumor, arteriosclerosis, etc. Various diagnostic and therapeutic methods using immunoglobulin are known to those skilled in the art.

When a perfect human immunoglobulin molecule is prepared from the immunoglobulin variable domain obtained according to the present invention, it can be used not only as a simple affinity ligand but also as an antibody molecule. Specifically, the heavy chain variable region gene and light chain variable region gene obtained according to the present invention are ligated with CH gene and CL gene encoding the constant regions, respectively. When genes encoding the constant regions derived from IgG are used, the resultant immunoglobulin molecule can have an excellent opsonin activity.

All publications describing prior art cited herein are incorporated herein by reference.

Abscissa: 63 types of light chain variable region genes from germline (chromosome).

Ordinate: Types of antigens used in the screening for phage antibodies
From the deepest:
1. Tetanus toxin (TET)
2. Influenza virus antigen (IFL)
3. varicella-zoster virus antigen (VZGH)
4. Diphtheria toxin (DTD)
5. Summation for the items 6 and 7 (total)
6. Summation for sensitizing antigens (1+2+3+4) (immunized)
7. Summation for non-sensitizing antigens (antigens which ordinary persons never encounter in their lifetime, such as *C. elegans*) (no immunized)
  Height: the number of phage antibodies.

Figure 1:
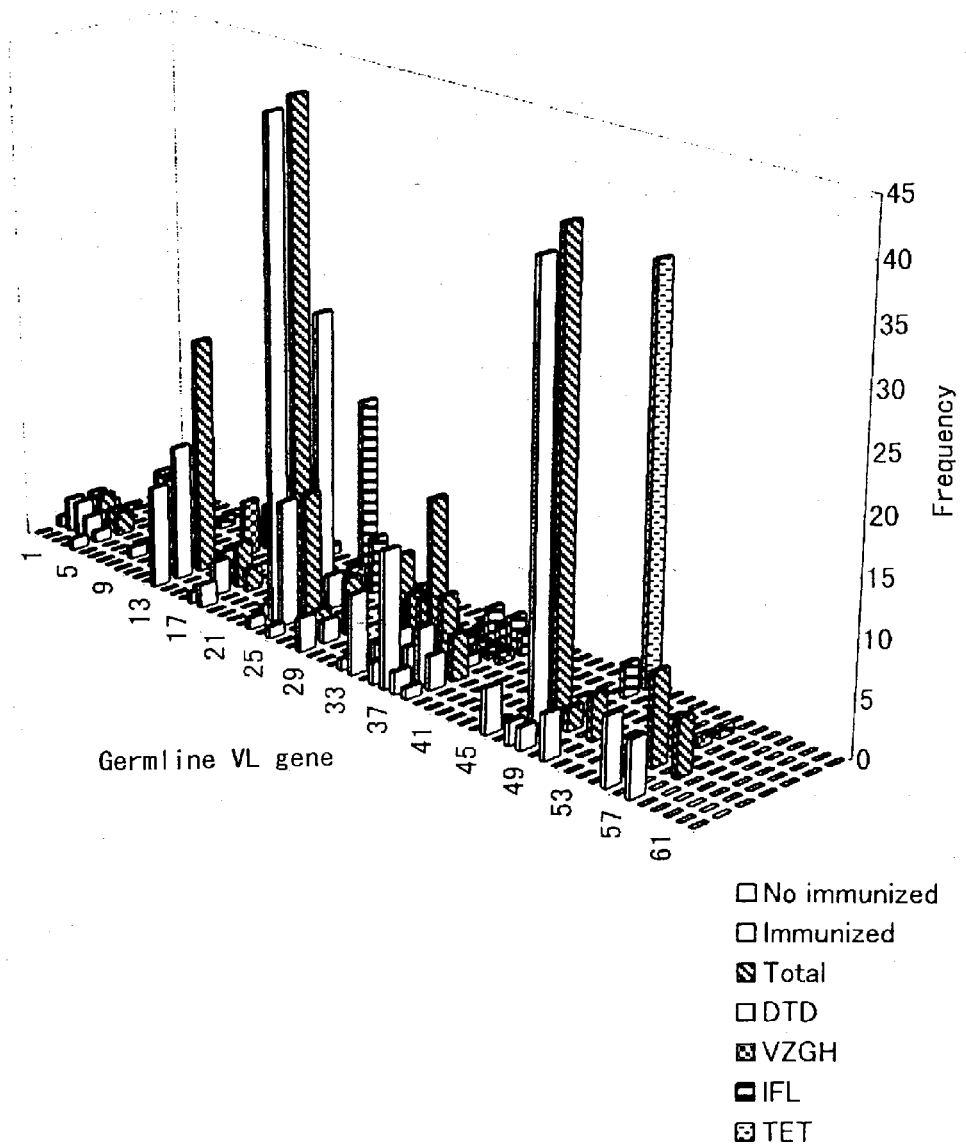
FIG. 1 shows a diagram summarizing the classification of VL genes of phage antibodies obtained according to the present invention.
Figure 2:
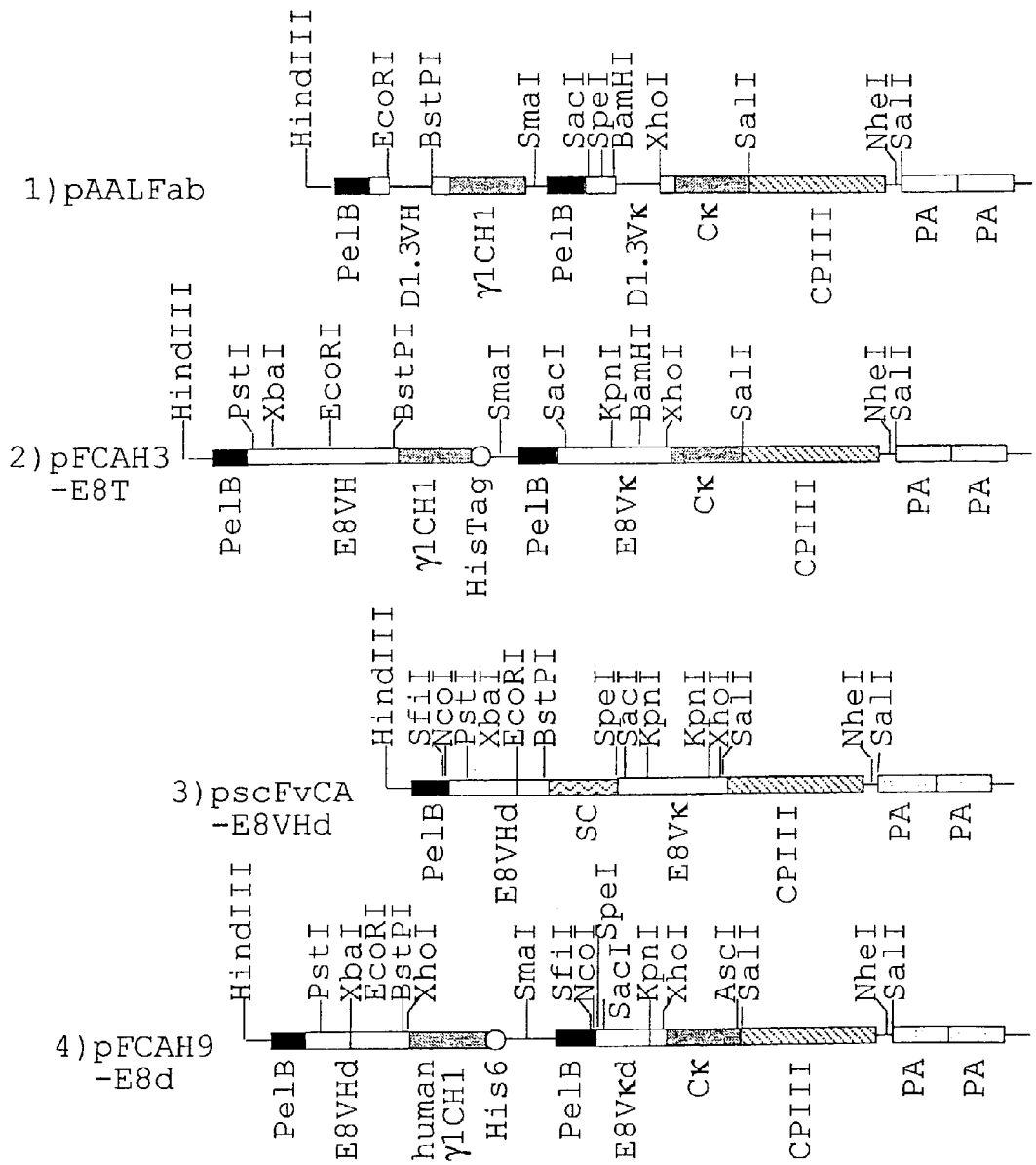

FIG. 2 shows a schematic illustration of structures of various vectors used for constructing the variable region library of the present invention.
(1) pAALFab: vector for D1.3 mutation.
(2) pFCAH3-E8T: expression vector for E8. This vector was constructed by modifying the restriction enzyme sites based on pAALFab. PstI, XbaI, and KpnI sites have been newly added; positions of the EcoRI and XhoI sites have been changed.
(3) pFvCA-E8VHd: cloning vector for the heavy chain variable region gene. This vector was constructed by modifying the restriction enzyme sites based on pFCAH3-E8T. The XbaI-EcoRI portion has been deleted; KpnI, SfiI, NcoI, and SpeI sites have been newly added. A heavy chain variable region gene can be cloned between SfiI and XhoI sites.
(4) pFCAH9-E8d: cloning vector for the heavy chain variable region gene. This vector was constructed by modifying the DNA sequence based on pFCAH3-E8T and pFvCA-E8VHd. Human γCH1 has been substituted for mouse γCH1. SfiI, NcoI, and AscI sites have newly been added. A light chain variable region can be cloned between the SfiI and AscI sites.

FIG. 3 shows the nucleotide sequence of insert in pFCAH9-E8d (SEQ ID NO: 99).

FIG. 4 shows positions of restriction enzyme sites in the nucleotide sequence (SEQ ID NO: 99) of the insert in pFCAH9-E8d and the amino acid sequence encoded by the nucleotide sequence (1) (SEQ ID NO: 100).

FIG. 5 shows positions of restriction enzyme sites in the nucleotide sequence (SEQ ID NO: 99) of the insert in pFCAH9-E8d and the amino acid sequence encoded by the nucleotide sequence (2) (SEQ ID NO: 101).

FIG. 6 shows positions of restriction enzyme sites in the nucleotide sequence (SEQ ID NO: 99) of the insert in pFCAH9-E8d and the amino acid sequence encoded by the nucleotide sequence (3) (SEQ ID NO: 102).

FIG. 7 shows the nucleotide sequence of the insert in pscFvCA-E8VHd (SEQ ID NO: 103).

FIG. 8 shows positions of restriction enzyme sites in the nucleotide sequence (SEQ ID NO: 103) of the insert in pscFvCA-E8VHd and the amino acid sequence encoded by the nucleotide sequence (1) (SEQ ID NO: 104).

FIG. 9 shows positions of restriction enzyme sites in the nucleotide sequence (SEQ ID NO: 103) of the insert in pscFvCA-E8VHd and the amino acid sequence encoded by the nucleotide sequence (2) (SEQ ID NO: 105).

Figure 10:
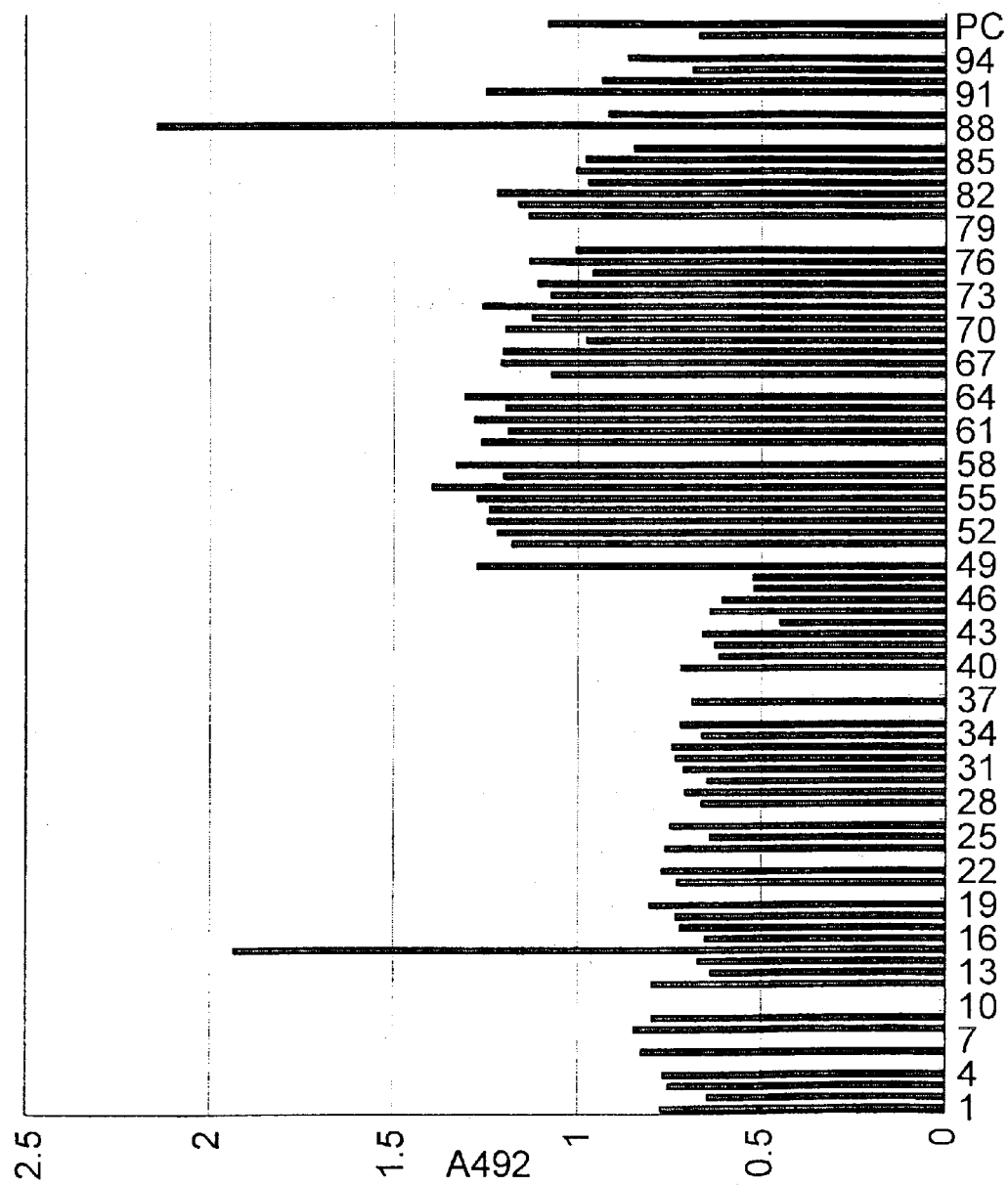

FIG. 10 shows a result obtained by assaying the affinity of the antibodies selected from the antibody library according to the present invention. The ordinate indicates absorbance at 492 nm; the abscissa indicates clone number. PC in the abscissa refers to a positive control.

Figure 11:
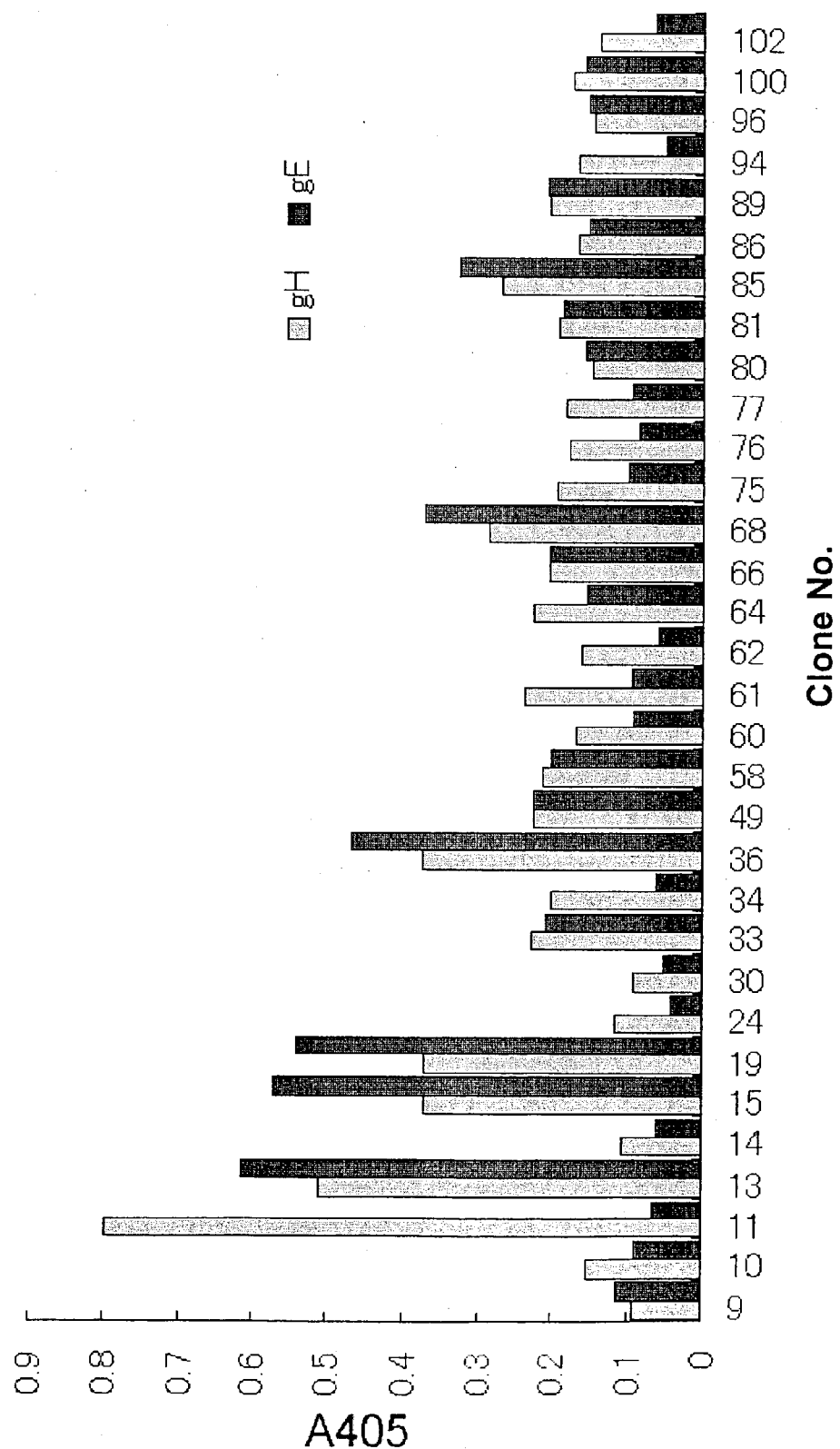

FIG. 11 shows the reactivity of each clone listed in Table 15 to gH or gE, which was measured by ELISA.

BEST MODE FOR CARRYING OUT THE INVENTION

The present invention is illustrated in detail below with reference to Examples.

Example 1

Preparation of Phagemid Vectors for Library Construction 1-1 Preparation of Vectors to Construct Combinatorial Libraries of the Heavy Chain and Light Chain As shown schematically in FIG. 2, the vector pFCAH9-E8d was prepared by inserting M13 phage-derived pelB (signal sequence), His6 tag sequence (SEQ ID NO: 106), M13 phage-derived sequence encoding cp3 protein (Acp3 (198aa to 406aa): the capsid protein 3 lacking the N terminus), and DNA encoding the amino acid sequence of protein A at appropriate restriction enzyme sites into pTZ19R phagemid vector (Pharmacia) (see Iba, Y. et al. GENE 194 (1997) 35-46). The genes encoding light chains λ5 and λ6 contained BstPI sites; to avoid such cleavage, pFCAH9-E8d has been designed to contain an XhoI site in addition to a BstPI site. The nucleotide sequence of the insert in pFCAH9-E8d is shown in FIG. 3; the restriction enzyme sites and the amino acid sequence encoded by the nucleotide sequence are shown in FIGS. 4 to 6.

A vector directing the expression of an antibody protein is completed by inserting the heavy chain and light chain genes at desired positions into the vector described above. With the vector constructed, the antibody is expressed as a Fab-type antibody; each of heavy chain and light chain contains the variable region at the N-terminus which is followed by the constant region CH1 or CL. The heavy chain is linked with the light chain via a disulfide bond between the constant regions. The gene CL encoding the light chain constant region is fused with the above-mentioned cp3 gene, and as a result the protein expressed is a Fab-cp3.

Specifically, the procedures used are as follows:
Primers used:

```
527 Reverse (SEQ ID NO: 2):
5'-CAGGAAACAGCTATGAC-3'

599 E8VHf-PstR (SEQ ID NO: 3):
3'-CGGCTCCAAGTCGACGTCGTCA-5'

544 E8VHf-PstF (SEQ ID NO: 4):
5'-CAGCTGCAGCAGTCTGGGGCAGAGCTTGTGAAGCCAGGGGCCT
CAGTCAAGTTGTCCTGCACAGCTTCTGGCTTCAACATTAAG-3'

545 E8VHf-XbaR (SEQ ID NO: 5):
3'-AGACCGAAGTTGTAATTTCTGTGGATATACGTGACCCACTTCG
TCTCCGGACTTTTCCCAGATCTCACCTAACCTTCCTAA-5'

546 E8VHf-XbaF (SEQ ID NO: 6):
5'-AAGGGTCTAGAGTGGATTGGAAGGATTGATCCTGCGAGTGGTA
```

```
-continued
ATACTAAATATGACCCGAAGGACAAGGCCACTATAACAGCA-3'

547 E8VHf-EcoR (SEQ ID NO: 7):
3'-TTCCTGTTCCGGTGATATTGTCGTCTGTGTAGGAGGTTGTGTC
GGATGGATGTCGACTTAAGGGAC-5'

548 E8VHf-EcoF (SEQ ID NO: 8):
5'-CAGCTGAATTCCCTGACATCTGAGGACACTGCCGTCTATTACT
GTGCTGGT-3'

549 E8VHf-BstR (SEQ ID NO: 9):
3'-CAGATAATGACACGACCAATACTAATGCCGTTGAAACTGATGA
CCCCGGTTCCGTGGTGCCAGTGGCACAAGG-5'

590 His6-SmaR (SEQ ID NO: 10):
3'-GGTTCTCTAACAGTAGTGGTAGTAGTGGTAATTATTCTCGATA
GGGCCCTCGAA-5'

542 E8VLf-SacF (SEQ ID NO: 11):
5'-GACATCGAGCTCACCCAGTCTCCAGCCTCCCTTTCTGCGTCTG
TGGGAGAAACTGTCACCATCACATGT-3'

539 E8VLf-KpnR (SEQ ID NO: 12):
3'-TGACAGTGGTAGTGTACAGCTCGTTCACCCTTATAAGTGTTAA
TAAATCGTACCATGGTCGTC-5'

542 E8VLf-KpnF (SEQ ID NO: 13):
5'-GCATGGTACCAGCAGAAACCAGGGAAATCTCCTCAGCTCCTGG
TCTAT-3'

543 E8VLf-BamR (SEQ ID NO: 14):
3'-GGAGTCGAGGACCAGATATTACGTTTTTGGAATCGTCTACCAC
ACGGTAGTTCCAAGTCACCGTCACCTAGGCCTTGTGTT-5'

562 E8VLf-XhoR (SEQ ID NO: 15):
3'-TCATGAGGCACCTGCAAGCCACCTCCGTGGTTCGAGCTCTAGT
TT-5'

563 E8VLf-XhoF (SEQ ID NO: 16):
5'-AGTACTCCGTGGACGTTCGGTGGAGGCACCAAGCTCGAGATCA
AA-3'

613 NheR (SEQ ID NO: 17):
3'-ATCGACAGCT-5'

600 E8VLKpnXhoR (SEQ ID NO: 18):
3'-AAGCCACCTCCATGGTTCGAGCTCTAGTTT-5'

LCP3ASC (SEQ ID NO: 19):
3'-TCGAAGTTGTCCTTACTCACAAGCCGCGCGGTCAGCTGAGGT
AA-5' hCH1Bst (SEQ ID NO: 20):
5'-ACCCTGGTCACCGTCTCCTCAGCCTCCACCAAGGGCCCATCG
GTCTTCCCCCTGG-3' hCH1midAS (SEQ ID NO: 21):
3'-GGGAGTCGTCGCAGCACTGGCACGGGAGGTCGTCGAA-5' hCH1midS (SEQ ID NO: 22):
5'-GGACTCTACTCCCTCAGCAGCGTCGTGACCGTGCCC-3' hCH1H6 (SEQ ID NO: 23):
3'-GGGTCGTTGTGGTTCCACCTGTTCTTTCAACTCGGGTTTAGA
ACAGTAGTGGTAGTAGTGGTA-5' hCH1H6Sma (SEQ ID NO: 24):
3'-GGGTTTAGAACAGTAGTGGTAGTAGTGGTAATTATTCTCGAT
AGGGCCCTCGAACG-5'

702 BstXhoF (SEQ ID NO: 25):
5'-GGCACCACGGTCACCGTCTCGAGCGCCTCCACC-3'
```

Preparation of the Heavy Chain Region in pFCAH3-E8T (1) DNA fragments were prepared by PCR using pAALFab as a template and primers 527-599 or primers 547-590.

(2) DNA fragments were prepared by PCR using primers 544-545, primers 546-547, or primers 548-549.

(3) The PCR products obtained in (1) and (2) were combined together. Then, PCR was carried out using primers 527 and 590, and the products were cloned into pAALFab at the HindIII-SinaI site.

pFCAH3-E8T Light Chain Region (4) DNA fragments were prepared by PCR using primers 542-562, or primers 561-613.

(5) DNA fragments were prepared by PCR primers 538-539, or primers 542-543.

(6) The PCR products obtained in (4) and (5) were combined together. Then, PCR was carried out using primers 538 and 562, and the products were cloned into pAALFab at the SacI-NheI site.

pfCAH9-E8d (6) Preparation of VH stuffer region pFCAH3-E8T was double-digested with XbaI and EcoRI, and both ends were blunted with klenow fragment. Then, the vector was self-ligated to prepare VH stuffer.

(7) Preparation of VH stuffer region

PCR was carried out using pFCAH3-E8T as a template and primers 527-600. The PCR products were cloned at HindIII-XhoI site into the construct obtained in (6).

(8) The constructed DNA was digested with KpnI, and then self-ligated to prepare VL stuffer.

(9) Introduction of SfiI, NcoI, and SpeI sites

PCR was carried out using pFCAH3-E8T as a template and primers 527-663. The PCR products were cloned at HindIII-SacI site into the construct obtained in (1).

(10) Introduction of AscI site

PCR was carried out using pFCAH3-E8T as a template and primers 527-LCP3ASC. The PCR products were cloned into the construct obtained in (2) that had been completely digested with SacI and partially digested with SalI.

(11) Replacement of the gamma CH1 region with the human gene

The human gamma CH1 region has BstPI sites; the gene was cloned with a strategy to abolish the BstPI sites. PCR was carried out using a cDNA derived from the tonsil as a template and primers hCH1Bst-hCH1midS or primers hCH1midAS-hCH1H6. The PCR products were combined together; PCR was carried out using the mixture as a template and primers hCH1Bst-hCH16Sma. The DNA fragment was cloned at BstPI-Sma site into the construct obtained in (3).

(12) Introduction of Xho site

PCR was carried out using the construct obtained in (11) as a template and primers 702-663, and the products were cloned at BstPI-SacI site into the construct obtained in (11).

1-2 Preparation of Vector to Transiently Clone the Heavy Chain Variable Region

First, the pAALFab vector (FIG. 2) was constructed according to a method known to those skilled in the art (see Iba, Y. et al., GENE 194 (1997) 35-46). The XbaI-EcoRI fragment was deleted from the pAALFab vector, and restriction enzyme digestion sites KpnI, SfiI, NcoI, and SpeI were newly added to the vector. The vector pscFvCA-E8VHd (FIG. 2) allowing the cloning of VH (heavy chain variable region) was finally constructed via pFCAH3-E8T. The vector constructed was used as a vector to transiently clone the heavy chain variable region. The nucleotide sequences of the inserts in pscFvCA-E8VHd are shown in FIG. 7, and restriction enzyme sites and the amino acid sequences encoded by the nucleotide sequences are shown in FIGS. 8 and 9.

Specifically, the procedures are as follows:
Primers used:
610 scBstSpeSacF (SEQ ID NO: 26):

```
610 scBstSpeSacF (SEQ ID NO: 26):
5'-CACCACGGTCACCGTCTCCTCAGGCGGTGGCGGATCAGGTGG
CGGTGGAAGTGGCGGTGGTGGGTCTACTAGTGACATCGAGCTCAC
CCAG-3'

611 scBstSpeSacR (SEQ ID NO: 27):
3'-GTGGTGCCAGTGGCAGAGGAGTCCGCCACCGCCTAGTCCACC
GCCACCTTCACCGCCACCACCCAGATGATCACTGTAGCTCGAGTG
GGTC-5'

527 Reverse (SEQ ID NO: 28):
5'-CAGGAAACAGCTATGAC-3'

619 E8VHf-SfiNcoPstR (SEQ ID NO: 29):
3'-GACGCCGGGTCGGCCGGTACCGGCTCCAAGTCGACGTCGTCA-5'
```

Primers 610 and 611 were annealed together, and then cloned into pFCAH3-E8T at the BstPI-SacI site. Single chain preparation was carried out based on this construct. Further, PCR was carried out using primers 527 and 619, and the resulting products were inserted into the construct at the HindIII-PstI site to introduce SfiI and NcoI sites.

Example 2

Preparation of an Immunoglobulin Light Chain Library 2-1 Isolation of Immunoglobulin Light Chain Genes Using PCR 2.6 µg mRNA was extracted from bone marrow cells (specimen No. 59) $4 \times 10^7$ cells, umbilical blood lymphocytes or peripheral blood lymphocytes using a commercially available kit (QuickPrep Micro mRNA Purification Kit; Pharmacia Biotech). cDNA was prepared from the mRNA. cDNA preparation was carried out with the SuperScript Preamplification System from GibcoBRL. The primer used was oligo dT. PCR was carried out using the obtained cDNA as a template and 5' primer (κ1 to κ6, κ1 to κ6) and 3' primer (hCK-ASC primer or hCLASC primer) for the light chain gene. After being treated with phenol, the PCR products were ethanol-precipitated. The DNA was suspended in 10 µl of TE buffer. The nucleotide sequences of the primers and PCR condition used are as follows. The underlines in the nucleotide sequence of the primers for the light chain gene indicate SfiI or AscI site.

```
5'-primer κ1 to κ6 hVK1a (SEQ ID NO: 30):
GTCCTCGCAACTGCGGCCCAGCCGGCCATGGCC GACATCCAGA
TGACCCAGTCTCC hVK2a (SEQ ID NO: 31):
GTCCTCGCAACTGCGGCCCAGCCGGCCATGGCC GATGTTGTGA
TGACTCAGTCTCC hVK3a (SEQ ID NO: 32):
GTCCTCGCAACTGCGGCCCAGCCGGCCATGGCC GAAATTGTGT
TGACGCAGTCTCC hVK4a (SEQ ID NO: 33):
GTCCTCGCAACTGCGGCCCAGCCGGCCATGGCC GACATCGTGA
TGACCCAGTCTCC hVK5a (SEQ ID NO: 34):
GTCCTCGCAACTGCGGCCCAGCCGGCCATGGCC GAAACGACAC
TCACGCAGTCTCC hVK6a (SEQ ID NO: 35):
GTCCTCGCAACTGCGGCCCAGCCGGCCATGGCC GAAATTGTGC
TGACTCAGTCTCC

5'-primer λ1 to λ6 hVL1 (SEQ ID NO: 36):
GTCCTCGCAACTGCGGCCCAGCCGGCCATGGCC CAGTCTGTGT
TGACGCAGCCGCC hVL2 (SEQ ID NO: 37):
GTCCTCGCAACTGCGGCCCAGCCGGCCATGGCC CAGTCTGCCC
TGACTCAGCCTGC hVL3a (SEQ ID NO: 38):
GTCCTCGCAACTGCGGCCCAGCCGGCCATGGCC TCCTATGTGC
TGACTCAGCCACC hVL3b (SEQ ID NO: 39):
GTCCTCGCAACTGCGGCCCAGCCGGCCATGGCC TCTTCTGAGC
TGACTCAGGACCC hVL4 (SEQ ID NO: 40):
GTCCTCGCAACTGCGGCCCAGCCGGCCATGGCC CACGTTATAC
TGACTCAACCGCC hVL5 (SEQ ID NO: 41):
GTCCTCGCAACTGCGGCCCAGCCGGCCATGGCC CAGGCTGTGC
TCACTCAGCCGCC hVL6 (SEQ ID NO: 42):
GTCCTCGCAACTGCGGCCCAGCCGGCCATGGCC AATTTTATGC
TGACTCAGCCCCA

3' primer hCKASC (SEQ ID NO: 43):
TCGACTGGCGCGCCGAACACTCTCCCCTGTTGAAGCTCTTTGTG

3' primer HCLASC (SEQ ID NO: 44):
TCGACTGGCGCGCCGAACATTCTGTAGGGGCCACTGTCTTCTC
```

PCR Condition

| | |
|---|---|
| cDNA | 2 µl |
| 10x buffer #1 (attached to KOD) | 10 µl |
| dNTP mix (2.0 mM) | 10 µl |
| 25 mM MgCl$_2$ | 4 µl |
| 5' primer (100 pmol/µl) | 1 µl |
| 3' primer (100 pmol/µl) | 1 µl |
| sterilized MilliQ | 71 µl |
| KOD DNA polymerase (Toyobo 2.5 U/µl) | 1 µl |

35 cycles of: 94° C., 1 minute; 55° C., 2 minutes; 74° C., 1 minute.

2-2 A Method for Preparing a Light Chain Gene Library by Selecting Light Chains Suitable for Preparing the Library 2-2-1 Insertion of the Light Chain Gene into a Phagemid The PCR product obtained in Example 1 was treated with restriction enzymes under the following condition:

| | |
|---|---|
| PCR product | 10 µl |
| 10x NEB4 (attached to AscI) | 5 µl |
| 10x BSA (attached to SfiI) | 5 µl |
| sterilized MilliQ | 28 µl |
| AscI (10 U/µl; NEW ENGLAND Biolabs Inc.) | 1 µl |
| SfiI (20 U/µl; NEW ENGLAND Biolabs Inc.) | 1 µl |

The reaction mixture was incubated at 37° C. for one hour and then at 50° C. for one hour. After reaction, a 10-µl aliquot of the mixture was electrophoresed in an agarose gel. A band of approximately 600 bp was cut off and the DNA was purified using a Gene Clean II Kit (Funakoshi). pFCAH9-E8d (FIG. 2) was treated with the same restriction enzymes as used to digest the PCR products, and then purified using a Gene Clean II Kit. The vector was ligated with the restriction enzyme-treated PCR products by incubating at 16° C. for a period from 4 hours to overnight under the following condition.

| | |
|---|---|
| pFCAH9-E8d treated with restriction enzyme | 2 µl |
| PCR product treated with restriction enzyme | 1 µl |
| 10x ligation buffer | 1.5 µl |
| (attached to T4 DNA ligase) | |
| 10 mM ATP | 1.5 µl |
| sterilized MilliQ | 8 µl |
| T4 DNA ligase (10 U/µl; Takara Shuzo) | 1 µl |

2-2-2 Introduction of Phagemid into *E. coli*

*E. coli* DH12S was transformed with the obtained DNA ligate as follows. Specifically, the DNA ligate was ethanol-precipitated once, and then dissolved in 3 µl of ⅕TE (which is TE diluted 5 times with sterilized MilliQ). A 1.5-µl aliquot of the solution was combined with 20 µl of a liquid of competent cell DH12S (GIBCO BRL) and then the DNA was electroporated into the *E. coli* cells under the following condition:

| Electroporator | | |
|---|---|---|
| Cell-Porator (BRL; Cat. series 1600) | | |
| Settings; | voltage booster | 4 kΩ |
| | capacitance | 330 µF |
| | DC volts | LowΩ |
| | charge rate | Fast |

2-2-3 Secretion of an Fab-cp3-Type Antibody from *E. coli* Cells Transformed with Phagemid into Medium The above-mentioned transformed *E. coli* cells were inoculated to 2 ml of transformation medium (SOB). After the cells were cultured while being shaken at 37° C. for one hour, an aliquot of the culture was plated on an agar medium (ampicillin plate). The remaining was cultured in 2×YT medium containing 0.1% glucose and 100 µg/ml ampicillin, and then stored as a glycerin stock. The agar plate was incubated at 30° C., and then colonies grown were picked up with toothpicks for isolation. Plasmids were prepared from the colonies. The nucleotide sequences of the light chain genes were determined using the plasmids.

SOB medium: the following components were added to 950 ml of purified water; the mixture was shaken to dissolve them completely. Then, 10 ml of 250 mM KCl solution was added to the solution, and the pH of the mixture was adjusted to 7.0 using 5N NaOH. The volume of the mixture was adjusted to 1,000 ml by adding purified water thereto, and sterilized by autoclaving for 20 minutes. Immediately before use, 5 ml of sterilized 2M $MgCl_2$ was added to the medium.

| | |
|---|---|
| bacto-tryptone | 20 g |
| bacto-yeast extract | 5 g |
| NaCl | 0.5 g |

2×YT medium: the following components were added to 900 ml of purified water, and the mixture was shaken to dissolve them completely. The pH of the mixture was adjusted to 7.0 using 5N NaOH. The volume of the mixture was adjusted to 1,000 ml by adding purified water thereto. The medium was sterilized by autoclaving for 20 minutes.

| | |
|---|---|
| bacto-tryptone | 16 g |
| bacto-yeast extract | 10 g |
| NaCl | 5 g |

Other reagents were purchased from the following suppliers.

| Supplier | Name of item |
|---|---|
| Sigma | Ampicillin sodium salt |
| Wako Pure Chemical Industries | Phenol |
| Sigma | BSA |
| DIFCO | 2× YT medium |
| Wako Pure Chemical Industries | Kanamycin sulfate |
| Nacalai Tesque | Polyethylene glycol 6000 |
| Nacalai Tesque | Tween20 |
| Katayama Chemical | NaCl |
| Wako Pure Chemical Industries | IPTG |
| Wako Pure Chemical Industries | Skimmed milk |
| Wako Pure Chemical Industries | Sodium azide |
| Wako Pure Chemical Industries | Triethylamine |
| Wako Pure Chemical Industries | Hydrogen peroxide |
| Wako Pure Chemical Industries | OPD tablet |
| Wako Pure Chemical Industries | ethanol |

The above-mentioned treatment was practiced for all of κ1, κ2, κ3, κ4, κ5, and κ6, and λ1, λ2, λ3a, λ3b, λ4, λ5, λ6, λ7, λ8, λ9, and λ10 to confirm whether clones of interest were isolated. Then, clones from each group such as κ1 and κ2 were combined together so that the combining ratio could mimic the in vivo distribution. It has been known how the expression levels are actually distributed in vivo with respect to genes of the respective light chain groups. To prepare a VL library, these gene clones amplified by PCR and inserted into the vector were combined together so that the combining ratio could mimic the in vivo distribution. The component ratio of the respective families in the VL library is shown below.

TABLE 2

| Family | In vivo distribution (%)* | Component ratio in the VL library (%) | Component ratio in KL200 (%) |
|---|---|---|---|
| Vκ1 | 39 | 37 | 30.7 |
| Vκ2 | 12 | 12 | 19.8 |
| Vκ3 | 36 | 35 | 33.7 |
| Vκ4 | 12 | 12 | 10.9 |
| Vκ5 | 1 | 2 | 5.0 |
| Vκ6 | —** | 2*** | 0.0 |

*Griffith A D et al. EMBO J. (1994) 13, 3245-60.
**No description in the report
***Mixture containing equal amounts of cDNA prepared with primer VK6-2 and cDNA prepared with primer VK6-3

TABLE 3

| Family | In vivo distribution (%)* | Component ratio in the VL library (%) | Component ratio in KL200 (%) |
|---|---|---|---|
| Vλ1 | 43 | 41 | 34.1 |
| Vλ2 | 15 | 15*3 | 15.2 |

TABLE 3-continued

| Family | In vivo distribution (%)* | Component ratio in the VL library (%) | Component ratio in KL200 (%) |
|---|---|---|---|
| Vλ3 | 34 | 32*[4] | 25.3 |
| Vλ4 | 0 | 1.5*[5] | 0.0 |
| Vλ5 | 0 | 1.0*[6] | 11.1 |
| Vλ6 | 0 | 1.0 | 14.1 |
| Vλ7 | 6 | 6 | 0.0 |
| Vλ8 | 1 | 1 | 0.0 |
| Vλ9 | 1 | 1 | 0.0 |
| Vλ10 | —*[2] | 1 | 0.0 |

*Griffith A D et al. EMBO J. (1994) 13, 3245-60.
*[2]No description in the report
*[3]Mixture containing 5% of cDNA prepared with primer VL2 and 10% of cDNA prepared with primer VL2-2
*[4]Mixture containing 17% of cDNA prepared with primer VL3a-2 and 15% of cDNA prepared with primer VL3b
*[5]Mixture containing 0.5% of cDNA prepared with primer VL4a, 0.5% of cDNA prepared with primer VL4b, and 0.5% of cDNA prepared with primer VL4c
*[6]Mixture containing 0.5% of cDNA prepared with primer VL5abde and 0.5% of cDNA prepared with primer VL5c Then, sequencing was carried out to confirm the nucleotide sequences of approximately 1,000 types of light chain genes selected at random from the VL library. Specifically, the nucleotide sequences were determined by the dideoxy method using a fluorescent primer huCH1J (5'-ATTAATAA-GAGCTATCCCGG-3'/SEQ ID NO: 45) and a thermo sequence kit (Amersham Pharmacia) in the automatic sequencer L1-COR4200L(S)-2 (Aloka). Redundant clones were removed after the determined nucleotide sequences were compared. Further, clones which had been confirmed to have no deletion as compared with the data in DNA databases were combined with a clone for the heavy chain gene, VH3-4, whose expression had previously been confirmed. With such combinations, the expression was studied experimentally. The procedure used is described below. The amino acid sequence of VH3-4 is shown in SEQ ID NO: 1.

First, VH3-4 was double-digested with HindIII and XhoI to obtain the heavy chain gene, and then purified with a Gene Clean II Kit. On the other hand, clones of light chain genes, which had been confirmed to have no deletion, were also double-digested with HindIII and XhoI to obtain the light chain genes, and then purified using a Gene Clean II Kit. The fragments were ligated with the VH3-4 heavy chain gene to prepare a series of combinations of the genes. E. coli DH12S was transformed with the obtained DNA ligate. The colonies grown were inoculated to media in test tubes, and the expression was induced by adding IPTG thereto. Thus, the Fab-cp3-type antibodies were expressed and secreted into culture supernatants. Even without infecting helper phage, the Fab-cp3-type antibodies were expressed and secreted into culture supernatants, when the culture was continued for about 20 hours. ELISA was carried out using these culture supernatants by the following procedure.

2-2-4 ELISA Test for the Exact Expression and Association of the Heavy Chain and Light Chain
(1) Preparation of 96-Well Microtiter Plates on which an Antibody has been Immobilized A solution of anti-κ antibody (MBL; Code No. 159) was diluted to 1.25 µg/ml with 0.01 M sodium phosphate buffer (pH8.0) containing 0.1% NaN$_3$, and 100-µl aliquots of the solution were added to a microtiter plate. The anti-κ antibody was immobilized (adsorbed) on each well by allowing the plate to stand still at 4° C. overnight. The reaction solution was discarded, and 200 µl of 0.01 M sodium phosphate buffer (pH8.0) containing 5% BSA and 0.1% NaN$_3$ was added to each well of the microtiter plate. To prevent non-specific adsorption, the plate was subjected to blocking treatment, which was carried out by allowing the plate to stand still at 37° C. for two hours.

Then, an anti-λ antibody (MBL code No. 159), whose non-specific reactivities had been blocked by absorption, was diluted to 2.5 µg/ml with 0.0.1 M sodium phosphate buffer (pH8.0) containing 0.1% NaN$_3$, and 100-µl aliquots were added to the microtiter plate. The plate was allowed to stand still in a cold room overnight. The reaction solution was discarded, and 200 µl of 0.01 M sodium phosphate buffer (pH8.0) containing 5% BSA and 0.1% NaN$_3$ was added to each well of the microtiter plate. To prevent non-specific adsorption, the plate was subjected to blocking treatment, which was carried out by allowing the plate to stand still at 37° C. for two hours.

(2) Primary Reaction

100 µl each of a human Fab solution (10 µg/ml) as a positive control and PBS/0.1% NaN$_3$ as, a negative control was added to a microtiter plate. The expression of Fab-cp3-type antibody was induced by adding IPTG. 100-µl aliquots of the original culture supernatants were added to the microtiter plate, and the plate was incubated at 37° C. for one hour.

(3) Secondary Reaction

The microtiter plate after the primary reaction was washed five times with 0.05% Tween20-PBS. Then, 100-µl aliquots of an anti-Fd antibody solution diluted to 1 µg/ml with PBS/0.1% NaN$_3$ were added to the microtiter plate. The plate was incubated at 37° C. for one hour.

(4) Tertiary Reaction

The microtiter plate after the secondary reaction was washed five times with 0.05% Tween20-PBS. Then, 100-µl aliquots of alkaline phosphatase-conjugated anti-sheep IgG antibody diluted with PBS/0.1% NaN$_3$ (4000-fold dilution) were added to the microtiter plate. The plate was incubated at 37° C. for one hour.

(5) Color Development and Spectrometry

The microtiter plate after the tertiary reaction was washed five times with 0.05% Tween20-PBS. Then, 100-µl aliquots of a coloring substrate solution (SIGMA 1040; a phosphatase substrate tablet of SIGMA 10401 was dissolved in 5 ml of 50 mM diethanol amine (PH9.8)) were added to the microtiter plate. The plate was incubated at room temperature. When the absorbance at 405 nm reached 0.5 or more, a stop solution was added to the plate. The absorbance was determined by spectrometry in a plate leader (Titertek Multiscan MCC).

Clones assessed as positive (the absorbance was 0.5 or more) by ELISA were assumed to successfully express the Fab-cp3-type antibody and hold. Then, from such clones, 100 clones having higher reactivity were selected for each of κ chain gene and λ chain gene. The two sets of clones were combined together to prepare the library KL200 which was a collection of clones successfully expressing the Fab-cp3-type antibody and holding.

Example 3

Preparation of a Combinatorial Library Comprising Light Chain Gene Library and Heavy Chain Gene Library 3-1-1 Isolation of Immunoglobulin Heavy Chain Genes by PCR cDNA was prepared from lymphocytes of umbilical blood, bone marrow fluid, and peripheral blood, and tonsil by the same procedure as used in Example 2-1 using human R primer (primer 634 indicated below) or random hexamer. PCR was carried out using the cDNA as a template and 5' primers (VH1 to VH7) and a 3' primer (a mixture containing equal amounts of four types of human JH primers; primers 697 to 700 indicated below), or human μ primer (primer 634 indicated below), which had been designed to clone human antibody heavy chain genes; the primers are listed below. In the Table, SfiI sites are underlined. Since hVH2a does not belong to the germ line VH2 family, VH2a-2 primer was newly designed. In addition, since hVH4a does not correspond to all the VH4 family, hVH4a-2 primer was newly designed. Further, since VH5a does not correspond to the germ line VH5 subfamily, VH5a-2 primer was newly designed. A new primer hVH7 was designed for VH7. These genes were also amplified, and inserted into pscFvCA-E8VHd(0-2). The nucleotide sequences were determined to confirm the structures of amplified genes. The sequence of hVH5a-2 was highly homologous to that of hVH1a, and thus the gene product was predicted to be similar to that from the PCR product amplified with hVH1a; therefore, hVH5a-2 was not used. After being phenol-treated, the PCR products were ethanol-precipitated and suspended in 10 μl of TE buffer.

```
    634 humμCH1R (SEQ ID NO: 46):
    ATGGAGTCGGGAAGGAAGTC
```

Primes Used for Amplifying Genes of Each VH Family
Human VH Primer (SfiI Sites are Underlined)

```
628 hVH1a (SEQ ID NO: 47):
GTCCTCGCAACTGCGGCCCAGCCGGCCATGGCC CAGGTGCAG
CTGGTGCAGTCTGG 629 hVH2a (SEQ ID NO: 48):
GTCCTCGCAACTGCGGCCCAGCCGGCCATGGCC CAGGTCAAC
TTAAGGGAGTCTGG 630 hVH3a (SEQ ID NO: 49):
GTCCTCGCAACTGCGGCCCAGCCGGCCATGGCC GAGGTGCAG
CTGGTGGAGTCTGG 631 hVH4a (SEQ ID NO: 50):
GTCCTCGCAACTGCGGCCCAGCCGGCCATGGCC CAGGTGCAG
CTGCAGGAGTCGGG 632 hVH5a (SEQ ID NO: 51):
GTCCTCGCAACTGCGGCCCAGCCGGCCATGGCC CAGGTGCAG
CTGTTGCAGTCTGC 633 hVH6a (SEQ ID NO: 52):
GTCCTCGCAACTGCGGCCCAGCCGGCCATGGCC CAGGTACAG
CTGCAGCAGTCAGG 629-2 hVH2a-2 (SEQ ID NO: 53):
GTCCTCGCAACTGCGGCCCAGCCGGCCATGGCC CAGRTCACC
TTGAAGGAGTCTGGTCC 631-2 hVH4a-2 (SEQ ID NO: 54):
GTCCTCGCAACTGCGGCCCAGCCGGCCATGGCC CAGGTGCAG
CTACAGCAGTGGGG 632-2 hVH5a-2 (SEQ ID NO: 55):
GTCCTCGCAACTGCGGCCCAGCCGGCCATGGCC GAGGTGCAG
CTGGTGCAGTCTGG 712 hVH7 (SEQ ID NO: 56):
GTCCTCGCAACTGCGGCCCAGCCGGCCATGGCC CAGGTGCAG
CTGGTGCAATCTGGGTCTGAGT 697 hJH1-2 (SEQ ID NO: 57):
GGTGGAGGCACTCGAGACGGTGACCAGGGTGC 698 hJH3 (SEQ ID NO: 58):
GGTGGAGGCACTCGAGACGGTGACCATTGTCC 699 hJH4-5 (SEQ ID NO: 59):
GGTGGAGGCACTCGAGACGGTGACCAGGGTTC 700 hJH6 (SEQ ID NO: 60):
GGTGGAGGCACTCGAGACGGTGACCGTGGTCC
Human JH primer (BstPI and XhoI sites are underlined)
```

| | |
|---|---|
| cDNA | 2 μl |
| 10× buffer #1 (attached to KOD) | 10 μl |
| dNTP mix (2.0 mM) | 10 μl |
| 25 mM MgCl$_2$ | 4 μl |
| 5' primer (100 pmol/μl) | 1 μl |
| 3' primer (100 pmol/μl) | 1 μl |
| sterilized MilliQ | 71 μl |
| KOD DNA polymerase (2.5 U/μl; Toyobo) | 1 μl |

PCR condition: 35 cycles of: 94° C., 1 minute; 55° C., 2 minutes; 74° C., 1 minute.

3-1-2 Preparation of Heavy Chain Gene Library

The PCR products obtained in 3-1-1 were treated with restriction enzymes under the following condition:

| | |
|---|---|
| PCR product | 10 μl |
| 10× K buffer (Takara Shuzo) | 5 μl |
| sterilized MilliQ | 33 μl |
| HindIII (15 U/μl; Takara Shuzo) | 1 μl |
| XhoI (12 U/μl; Takara Shuzo) | 1 μl |

The reaction mixture was incubated at 37° C. for two hours. After reaction, a 10-μl aliquot of the mixture was electrophoresed in an agarose gel. A band of approximately 400 bp was cut off and the DNA was purified using a Gene Clean II Kit (Funakoshi). pscFvCA-E8VHd (FIG. 2) were treated with the same, restriction enzymes as used to digest the PCR products, and then purified using a Gene Clean II Kit. The vector was ligated with the restriction enzyme-treated PCR products by incubating at 16° C. for a period from 4 hours to overnight under the following condition.

| | |
|---|---|
| Restriction enzyme-treated pscFvCA-E8VHd | 2 μl |
| Restriction enzyme-treated PCR product | 1 μl |
| 10× ligation buffer (attached to T4 DNA ligase) | 1.5 μl |
| 10 mM ATP | 1.5 μl |
| sterilized MilliQ | 8 μl |
| T4 DNA ligase (10 U/μl; Takara Shuzo) | 1 μl |

3-1-3 Introduction of Phagemid into *E. coli*

*E. coli* DH12S was transformed with the obtained DNA ligate. Specifically, the DNA was ethanol-precipitated once, and then dissolved in 3 μl of ⅕TE (which is TE diluted 5 times with sterilized MilliQ). A 1.5-μl aliquot of the solution was suspended in 20 μl of a solution of competent cell DH12S (GIBCO BRL), and then the DNA was transformed into the *E. coli* cells by electroporation.

| Electroporator Cell-Porator (BRL; Cat. series 1600) | | |
|---|---|---|
| Settings; | voltage booster | 4 kΩ |
| | capacitance | 330 μF |
| | DC volts | LowΩ |
| | charge rate | Fast |

The E. coli cells transformed by the above-mentioned procedure were inoculated to 2 ml of transformation medium (SOB). After the cells were cultured while being shaken at 37° C. for one hour, an aliquot of the culture was plated on an agar medium (ampicillin plate). The remaining was cultured in 2×YT medium containing 0.1% glucose and 100 μg/ml ampicillin, and then stored as a glycerin stock. The agar plate was incubated at 30° C., and then colonies grown were picked up with toothpicks for isolation. Plasmids were prepared from the colonies, and the nucleotide sequences of the heavy chain genes were determined using the plasmids. The above-mentioned treatment was practiced for all of VH1 to VH7 to confirm whether clones of interest were isolated. Then, to prepare a VH library, clones from each group (family) were combined together so that the combining ratio could mimic the in vivo distribution. The component ratio of the respective families in the VH library is shown below.

TABLE 4

| Family | In vivo distribution (%)* | Component ratio in the VH library (%) |
|---|---|---|
| VH1 | 25 | 29** |
| VH2 | 6.6 | 7 |
| VH3 | 40 | 40 |
| VH4 | 19 | 19*** |
| VH5 | 5 | —** |
| VH6 | 3.8 | 4 |
| VH7 | 1.2 | 2 |

*Griffith A D et al. EMBO J. (1994) 13, 3245-60.
**Actually, VH1 and VH5 are inseparable in tabulation, because both are amplified with identical primers.
***A mixture was prepared by combining cDNA synthesized with primer VH4 and cDNA synthesized with primer VH4-2 at this ratio.

3-2 Preparation of a Combinatorial Gene Library

200 μg of the VH library was double-digested with HindIII and XhoI under the condition as described below to obtain the heavy chain gene, and the digest was purified with a Gene Clean II Kit.

| VH library 200 μg | 100 μl |
|---|---|
| 10× K buffer (Takara Shuzo) | 40 μL |
| sterilized MilliQ | 205 μl |
| HindIII (40 U/μl; Takara Shuzo) | 30 μL |
| XhoI (50 U/μl; Takara Shuzo) | 25 μl |

The light chain gene clone KL200, which had been confirmed to have no deletion, and the vector pFCAH9-E8d in which the VL library had been inserted, were also double-digested with HindIII and XhoI under the following condition. Then, the fragments containing the light chain gene were purified using a Gene Clean II Kit.

| pFCAH9-E8d containing KL200 or VL library as an insert 100 μg | 100 μl |
|---|---|
| 10× K buffer (Takara Shuzo) | 40 μl |
| sterilized MilliQ | 230 μl |
| HindIII (40 U/μl; Takara Shuzo) | 15 μl |
| XhoI (50 U/μl; Takara Shuzo) | 15 μl |

Then, the fragments of the VH gene library and pFCAH9-E8d vector in which the light chain gene had been inserted were ligated together under the following condition at 16° C. overnight.

| Restriction enzyme-treated Fragments of the VH library 10 μg | 50 μl |
|---|---|
| pFCAH9-E8d containing Restriction enzyme-treated KL200 or Fragments of the VL library 40 μg | 50 μl |
| 10× ligation buffer (attached to the T4 DNA ligase) | 100 μl |
| 10 mM ATP | 100 μL |
| Sterilized MilliQ | 670 μl |
| T4 DNA ligase (10 U/μl; Takara Shuzo) | 30 μl |

E. coli DH12S was transformed with the DNA after the reaction. Specifically, the DNA was ethanol-precipitated once, and then dissolved in 30 μl of 1/5TE (which is TE diluted 5 times with sterilized MilliQ). The DNA solution was combined with 500 μl of competent cell DH12S (GIBCO BRL), and then electroporation was carried out.

| Electroporator Cell-Porator (BRL; Cat. series 1600) | | |
|---|---|---|
| Settings; | voltage booster | 4 kΩ |
| | capacitance | 330 μF |
| | DC volts | LowΩ |
| | charge rate | Fast |

The E. coli cells after the above-mentioned treatment were inoculated to 12 ml of transformation medium (SOB). After the cells were cultured while being shaken at 37° C. for one hour, an aliquot of the culture was plated on an agar medium (ampicillin plate). The remaining was cultured in 500 ml of 2×YT medium containing 0.1% glucose and 100 μg/ml ampicillin, and then stored as a glycerin stock. The agar plate was incubated at 30° C., and then the number of clones obtained was estimated based on the number of colonies grown. $5 \times 10^{10}$ clones were obtained for each library.

cDNAs of each VH family, which had been synthesized from tonsil mRNA using random hexamer as a primer, were cloned into pscFvCA-E8VHd vector. The cDNA constructs were combined with KL200 to prepare a combinatorial library AIMS1 (the number of independent clones was $1.28 \times 10^{10}$).

cDNAs of each VH family, which had been synthesized from mRNAs from umbilical blood, bone marrow fluid, peripheral blood, and tonsil using the human m primer, were cloned into pscFvCA-E8VHd vector. The cDNA constructs were combined with KL200 to prepare a combinatorial gene library AIMS2 (the number of independent clones was $3.20 \times 10^{10}$).

The library of VH family cDNAs, which had been synthesized from mRNAs prepared from umbilical blood, bone marrow fluid, peripheral blood, and tonsil using the human m primer, was combined with the VL library to prepare a combinatorial library AIMS3 (the number of independent clones was $4.50 \times 10^{10}$).

Another combinatorial library was prepared by combining the libraries at the following ratio:

(AIMS1+AIMS2):AIMS3=1:1. The resulting phage antibody library was named AIMS4 and contained $1 \times 10^{11}$ independent clones.

3-3 Preparation of Phage Libraries Using the Combinatorial Gene Libraries
3-3-1 Preparation of Phage Libraries 2.5 ml of an AIMS4 suspension was added to 300 ml of 2×YT medium containing 1% glucose and 100 μg/ml ampicillin in a 5-liter flask. Culture was continued at 37° C. while the flask was being shaken. The absorbance at wavelength 600 nm was measured at 1-hour intervals. The incubation was continued until the absorbance reached 1.0. 12 ml/flask of helper phage liquid (M13KO7) was added to the culture medium to infect the helper phage. Culture was continued at 37° C. for 2 hours. Thus, helper phage-infected DH12S cells were prepared.

600 ml of 2×YT medium, 1.2 ml of 100 µg/ml ampicillin, 0.8 ml of 50 µg/ml kanamycin, and 200 ml of the helper phage-infected DH12S suspension were added to twenty four 3-liter flasks. The flasks were incubated at 37° C. while being shaken. The absorbance at wavelength 600 nm was measured at 2-hour intervals. Ampicillin was freshly added at a final concentration of 200 µg/ml to each flask at every absorbance measurement. Incubation was continued until the absorbance at wavelength 600 nm reached 1.3.

The bacterial cultures were centrifuged at 8,000 rpm for ten minutes at 4° C., and the supernatants were collected. 4 liters of 20% polyethylene glycol/2.5M NaCl was added to each supernatant. The mixture was stirred gently for about 20 minutes, and then centrifuged at 8,000 rpm for 20 minutes at 4° C. The resulting precipitate was dissolved in 1 liter of PBS. 200 ml of 20% polyethylene glycol/2.5M NaCl was added to the solution and the mixture was stirred gently for about 20 minutes. Then, the mixture was centrifuged at 8,000 rpm for 20 minutes at 4° C. The supernatant was discarded, and the remaining material was further centrifuged at 8,000 rpm for three minutes at 4° C. The pellet was collected. The precipitate was dissolved in PBS containing 0.05% NaN$_3$. The solution was centrifuged at 1,000 rpm for 15 minutes at 4° C., and then the supernatant was collected. The supernatant was again centrifuged at 8,000 rpm for three minutes at 4° C. The resulting supernatant was collected.

The titer of recovered phage liquid was tested as described below. Specifically, the phage liquid was diluted $10^6$ times, $10^7$ times, or $10^8$ times with PBS. A 10-µL aliquot of the dilute was combined with 990 µl of DH12S for infection. The mixture was incubated at 37° C. for one hour. A 100-µl aliquot of the culture was plated on an LBGA plate. The plate was incubated at 30° C. for 18 hours. The phage titer of original liquid before dilution was estimated based on the number of colonies. The phage stock solution was diluted with PBS containing 2% skimmed milk and 0.05% NaN$_3$ to $2 \times 10^{14}$ particles/ml.

3-3-2 A Method for Enriching Phage Particles Expressing Fab-cp3 on the Surface

The library prepared as described above was designed so that phage particles expressing Fab-cp3 on the surface could be selectively enriched and the level of contamination of helper phage particles and phage particles expressing no Fab-cp3 would be reduced. Specifically, His6 peptide (SEQ ID NO: 106) (histidine tag) was attached to the C-termini of heavy chains expressed on the phages constituting the above-mentioned library. Phage particles expressing the histidine tag can be recovered simply by trapping them on nickel ion or the like. Specifically, gel containing nickel ions (Ni-NTA agarose, etc) can be used. The procedure used was as follows.

For blocking, Ni-NTA agarose was incubated in PBS containing 2% skimmed milk and 0.1% Tween-20 (hereinafter referred to as blocking buffer) at room temperature for 30 minutes. Then, in the blocking buffer, phages expressing, on the surface, Fab comprising the heavy chain without His-Tag (pFCA-E9HL4; phage His-) and phages expressing, on the surface, Fab comprising the heavy chain with His-Tag (pFCAH6-D1.3HLφ; phage His+) were combined together at a ratio of: phage His-:phage His+=100:1. 250 µl of the phage solution ($1 \times 10^{10}$ CFU in total) was combined with Ni-NTA agarose, and the mixture was incubated at room temperature for one hour. The Ni-NTA agarose was washed with the blocking buffer, and then 500 µl of 0.5 M imidazole (pH 7.55) was added thereto to elute the phage particles bound to the Ni-NTA agarose.

The eluted phage particles were recovered according to the method as described below (Example 4-3). Then, the recovered clones were examined. Of 23 clones, 15 were phages of His+ (Table 3). This suggests that Ni-NTA agarose enriched His6 peptide-containing phage particles 53 times (6His peptide disclosed as SEQ ID NO: 106).

The findings described in (4) demonstrate that this treatment can improve the library performance or increase screening efficiency.

TABLE 5

|  | Phage without His6-tag | Phage carrying His6-tag |
|---|---|---|
| Before Ni-NTA agarose treatment | 100 | 1 |
| After Ni-NTA agarose treatment | 15 | 8 |

** 6xHis tag is disclosed as SEQ ID NO: 106

Example 4

Selection of Phages Binding to a Specific Antigen from a Phage Library (Part 1)

A procedure of selecting phages binding to a specific antigen from a phage library is herein referred as "screening". Screening of the antibody library of the present invention was carried out using tetanus toxoid as an antigen.

4-1 Preparation of Test Tubes to be Used in the Screening

The concentration of the antigen (tetanus toxoid) was adjusted to 20 µg/ml with PBS, and a 3-ml aliquot of the solution was added to each of three test tubes (Maxisorp; Nunc). The mixtures were incubated at 4° C. for 18 hours to absorb the antigen on the inner surface of the tubes. After adsorption, the antigen solution was discarded, and a 3-ml aliquot of a PBS solution containing 2% skimmed milk was added thereto. Blocking was carried out by incubating the test tubes at 25° C. for one hour, to avoid non-specific adsorption of phage antibodies on the test tubes.

4-2 Screening Method

A 3-ml aliquot of an AIMS4 phage library ($1 \times 10^{14}$ CFU) in 9 ml of PBS containing 2% skimmed milk and 0.1% Tween-20 was added to each of the three antigen-immobilized test tubes. The tubes were incubated at 25° C. for 2 hours, and then washed 4 times with PBS containing 0.1% Tween-20, 4 times with PBS, and once sterilized extra pure water (prepared by MilliQ).

Then, phage particles bound to the antigen-immobilized test tubes were recovered by the procedure as described below. Specifically, 3 ml of 0.1 M triethylamine (pH 12.3) was added to each test tube, and the tubes were incubated while being rotated with a rotator at room temperature for 20 minutes to dissociate the phage particles from tube surface. Then, 1.1 ml of 1 M Tris-HCl buffer (pH 6.8) was added to the tubes to neutralize the liquid. The neutralized phage solutions were collected.

4-3 Amplification of the Collected Phages

The phage solutions collected were treated as follows:
(a) the phage was infected to E. coli cells;
(b) helper phage was infected to E. coli cells; and
(c) the resulting phage particles were collected.

The phage particles in the solution were thus purified and amplified.

(1) Infection of Phage Particles to E. coli Cells

E. coli (DH12S) cells were cultured in 50 ml of 2×YT medium, until the absorbance at 600 nm reached 0.5. Then, the phage solution prepared as described above was added to the culture. Shaking culture was continued at 37° C. for one hour.

(2) Infection of Helper Phage

A 62.3-ml aliquot of the culture solution obtained by (1) was added to 425 ml of 2×YT medium containing 12.5 ml of 40% glucose and 0.5 ml of 100 µg/ml ampicillin. Culture was continued at 37° C., until the absorbance at 600 nm reached 0.5. Then, the culture liquid was centrifuged at 5,000 rpm at 4° C. for ten minutes to precipitate the bacterial cells. The cells were collected and suspended in 300 ml of 2×YT medium containing 0.3 ml of 100 mg/ml ampicillin. A 1/100 volume of helper phage M13K07 was added to the culture, and then shaking culture was continued at 37° C. for one hour.

The culture solution was added to 900 ml of medium (2×YT medium containing 100 µg/ml ampicillin and 70 µg/ml kanamycin) pre-warmed at 37° C. The resulting culture solution was incubated at 37° C. overnight.

(3) Phage Recovery

The culture solution prepared in (2) was centrifuged at 7,000 rpm for ten minutes at 4° C., and then a 1/5 volume of 20% polyethylene glycol containing 2.5 M sodium chloride was added to the resulting supernatant. The mixture was allowed to stand still at room temperature for 20 minutes, and then centrifuged at 8,000 rpm for 15 minutes at 4° C. The pellet was collected, and sterilized PBS was added to the pellet in an amount that corresponded to 1/10 of the volume of the culture solution, thereby dissolving the pellet. Again, a 1/5 volume of a solution of 20% polyethylene glycol containing 2.5 M sodium chloride was added to the suspension. The mixture was centrifuged at 10,000 rpm for 20 minutes at 4° C., and then the supernatant was discarded. The sample was further centrifuged at 10,000 rpm for 2 minutes at 4° C. to remove residual liquid. PBS containing 0.05% $NaN_3$, which corresponded to 1/100 volume of the culture solution, was added to the pellet to suspend the phage particles. Thus, the phage particles were collected.

4-4 Re-Screening Using the Amplified Phage

Screening was repeated using the amplified phage particles and antigen-immobilized test tubes by the same procedure as used in Example 4-2. The washing step in the screening was important to dissociate the non-specifically adsorbed phage particles and to select phages having high affinity. Thus, the washing in the secondary and subsequent screening was carried out under the following condition.

Secondary screening: 6 times with PBS containing 0.1% Tween-20, 6 times with PBS, once with sterilized extra pure water.

Tertiary screening: 13 times with PBS containing 0.1% Tween-20, 13 times with PBS, once with sterilized extra pure water.

4-5 Method for Evaluating Phage Screening

When the ratio of (the total number of phase particles recovered from the antigen-immobilized test tube)/(the total number of phase particles in an antigen-immobilized test tube) becomes obviously smaller than that of the previous screening in screenings conducted serially according to the method described in Example 4-4, phage particles displaying the desired antibody are estimated to be enriched. The number of phage particles in the phage solution was determined by the following procedure.

(1) A serial dilution of phage particles was prepared as follows:

[1] $1\times10^{-2}$ dilution: 10 µl of the phage solution+990 µl of PBS
[2] $1\times10^{-4}$ dilution: 10 µl of the dilute in [1]+990 µl of PBS
[3] $1\times10^{-6}$ dilution: 10 µl of the dilute in [2]+990 µl of PBS
[4] $1\times10^{-8}$ dilution: 10 µl of the dilute in [3]+990 µl of PBS
[5] $1\times10^{-9}$ dilution: 100 µl of the dilute in [4]+900 µl of PBS
[6] $1\times10^{-10}$ dilution: 100 µl of the dilute in [5]+900 µl of PBS 990 µl of DH12S was combined with each of 10-µl aliquots of the dilutes prepared in [4], [5], and [6] in the serial dilution. The mixtures were incubated at 37° C. for one hour for infection, and 100-µl aliquots thereof were plated on LBGA plates, followed by incubation at 30° C. for 18 to 24 hours. The resulting colonies grown were counted. Normally, in the above-described serial dilution, the dilute prepared in [4] provides 50 or more colonies on a plate. The phage titer (the number of phage particles) in 1 ml of the phage solution was estimated based on the number of colonies grown on the plate corresponding to the dilute prepared in [4] by the following formula.

The number of phage particles in the phage stock solution=(the number of colonies/plate)×(1×$10^8$)×$10^3$ cfu/ml The number of phage particles recovered was also estimated in the same way, and thereby the number of phage particles displaying the antibody against the antigen was determined for each screening. The result is shown in Table 6.

TABLE 6

| The number of screening repetitions | The number of washing repetitions | The number of phage particles used | The number of phage particles recovered | (The number of phage particles used)/ (The number of phage particles recovered) |
|---|---|---|---|---|
| 1 | 4 | $1.15 \times 10^{14}$ | $6.1 \times 10^8$ | $1.9 \times 10^5$ |
| 2 | 6 | $3.9 \times 10^{13}$ | $2.2 \times 10^7$ | $1.8 \times 10^6$ |
| 3 | 8 | $1.2 \times 10^{13}$ | $5.4 \times 10^8$ | $2.2 \times 10^4$ |

4-6 Determination of Antigen-Binding Activity (Affinity) of Antibodies Obtained Through Screening The antigen-binding activity (affinity) was determined for the antibodies selected by the screening as described above. Not phage antibodies but Fab-cp3-type antibodies were used as samples for determining the affinity. The assay method used was ELISA using 96-well microtiter plates. The method for inducing the expression of Fab-cp3-type antibodies is described below in detail in Example 4-7.

First, ELISA plates were prepared as follows. 100 µl of 20 µg/ml antigen was added to each well of 96-well microtiter plates (Maxisorp; Nunc), and then the plates were incubated at 4° C. for 18 hours for immobilization. 200 µl of 5% BSA (blocking solution) was added to each well, and then the plates were incubated at 37° C. for one hour for blocking. After the blocking solution was discarded, the plates were washed once with PBS. These plates were used for determining the affinity. 100 µl of the culture supernatant recovered by the procedure as described in Example 4-7 was added to each well. The plates were incubated at 25° C. for one hour. After incubation, the plates were washed four times with PBS. 100 µl of peroxidase-conjugated anti-human IgG (Medical and Biological Laboratories Co.), which had been diluted 5,000 times, was added to the plates. The plates were incubated at 25° C. for one hour, and then washed again four times with PBS. 100 μl of a solution containing ortho-phenylenediamine and hydrogen peroxide was added to the plates. After the plates were incubated for a desired time, 100 μl of 1.5 N phosphoric acid was added thereto to stop the reaction. The absorbance measured at a wavelength of 492 nm. Thus, of the 96 clones, 77 clones were confirmed to have the activity (FIG. 10).

Further, it was tested whether 37 clones selected from the 77 clones had the neutralizing activity or not. Clones marked with circle in Table 7 were tested for the neutralizing activity. At the time of testing the neutralizing activity, the nucleotide sequences of the clones had not yet been determined; some of the clones might share identical DNA sequences. The nucleotide sequences of the clones were determined and compared to one another. Thus, clones sharing an identical nucleotide sequence are categorized into an identical group in Table 7. By the comparison carried out after sequence determination, it was confirmed that clones sharing an identical DNA sequence showed equivalent level of affinity determined by ELISA to each other.

4-7 Induction of Expression of Fab-cp3-Type Antibodies

Phage-infected *E. coli* cells were cultured in 2×YT medium containing 1% glucose and 100 μg/ml ampicillin at 30° C. for 18 hours. Then, a 5-μl aliquot of the culture was added to 1.5 ml of 2×YT medium containing 0.1% glucose and 100 μg/ml ampicillin. The mixture was incubated at 30° C. for 4 hours. After the culture is completed, the absorbance at 600 nm, which corresponded to *E. coli* cell density, was about 0.5.

IPTG (isopropyl-1-thio-β-D-galactoside) was added at a final concentration of 1 mM to the culture. Incubation was continued at 30° C. for 18 hours. A 1.5-ml aliquot of the culture was added to an Eppendorf tube, and centrifuged at 10,000 rpm for 5 minutes at 4° C. The resulting culture supernatant was collected and sodium azide was added thereto at a final concentration of 0.1%. The supernatant was used as a sample.

ELISA as described in Example 2-3 was used to determine whether the Fab-cp3-type antibody was expressed or not. Clones confirmed to be expressed were tested for deletion by agarose electrophoresis. Deletion was found in 8 clones. All of these clones were confirmed to have no antigen-binding activity.

4-8 Single-Clone Separation and Phagemid Purification

*E. coli* clones were selected from the plates for single-colony separation, which had been prepared according to Example 4-5 "Method for evaluating phage screening", and then cultured in LBGA at 30° C. for 18 hours. Then, phagemids were purified using a DNA extractor (PI-50 File No. 50) purchased from Kurabo.

4-9 Identification of Monoclonal Antibodies

Sequencing was carried out to determine the nucleotide sequences of the genes encoding anti-tetanus toxin antibodies selected from the antibody library of the present invention by screening. The heavy chain and light chain genes were sequenced using the primers listed below by the dideoxy method with a thermo sequence kit (Amersham Pharmacia) and an automatic sequencer. L1-COR4200L (S)-2 (Aloka). The result is summarized in Table 7, where clones sharing an identical nucleotide sequence are categorized into an identical group based on the determined nucleotide sequences. In this Table, when having a same combination of the number for the H chain and the number for the L chain, clones comprise an identical nucleotide sequence. As seen in Table 7, 36 types of distinct clones were isolated.

Sequencing primers for the heavy chain: fluorescent labeled T7 primer (Aloka)

Sequencing primers for the light chain: fluorescent labeled primer huCH1J (SEQ ID NO: 45)

TABLE 7

| Clone No. | ELISA Absorbance | H-chain DNA sequence ID NO: | VH1 classification | KL200 | Germ line VL | H-L gene combination ID NO. | The conduct of neutralization test |
|---|---|---|---|---|---|---|---|
| TETM18 | 0.7321 | 1 | DP10 (VH1) | L3BUM6 | 31 | 1 | ○ |
| TETM40 | 0.7185 | 1 | DP10 (VH1) | L3BUM6 | 31 | 1 | ○ |
| TETM42 | 0.6266 | 1 | DP10 (VH1) | L3BUM6 | 31 | 1 | ○ |
| TETM51 | 1.1731 | 1 | DP10 (VH1) | L3BUM6 | 31 | 1 | |
| TETM53 | 1.2410 | 1 | DP10 (VH1) | L3BUM6 | 31 | 1 | |
| TETM57 | 1.1961 | 1 | DP10 (VH1) | L3BUM6 | 31 | 1 | |
| TETM61 | 1.1833 | 1 | DP10 (VH1) | L3BUM6 | 31 | 1 | |
| TETM63 | 1.1912 | 1 | DP10 (VH1) | L3BUM6 | 31 | 1 | |
| TETM68 | 1.1971 | 1 | DP10 (VH1) | L3BUM6 | 31 | 1 | |
| TETM70 | 1.1911 | 1 | DP10 (VH1) | L3BUM6 | 31 | 1 | |
| TETM72 | 1.2544 | 1 | DP10 (VH1) | L3BUM6 | 31 | 1 | |
| TETM76 | 1.1253 | 1 | DP10 (VH1) | L3BUM6 | 31 | 1 | |
| TETM81 | 1.1559 | 1 | DP10 (VH1) | L3BUM6 | 31 | 1 | |
| TETM84 | 0.9991 | 1 | DP10 (VH1) | L3BUM6 | 31 | 1 | |
| TETM85 | 0.9737 | 1 | DP10 (VH1) | L3BUM6 | 31 | 1 | |
| TETM24 | 0.7613 | 1 | DP10 (VH1) | 13b-10b, 13b-6b | 31 | 12 | ○ |
| TETM02 | 0.6460 | 2 | DP10 (VH1) | 13b-12b | 31 | 4 | ○ |
| TETM09 | 0.7987 | 2 | DP10 (VH1) | 13b-12b | 31 | 4 | ○ |
| TETM44 | 0.4468 | 2 | DP10 (VH1) | 13b-12b | 31 | 4 | |
| TETM93 | 0.6824 | 2 | DP10 (VH1) | 13b-12b | 31 | 4 | |
| TETM14 | 0.6707 | 2 | DP10 (VH1) | 13b-10b, 13b-6b | 31 | 3 | ○ |
| TETM25 | 0.6402 | 2 | DP10 (VH1) | 13b-10b, 13b-6b | 31 | 3 | ○ |
| TETM47 | 0.5186 | 2 | DP10 (VH1) | 13b-10b, 13b-6b | 31 | 3 | |
| TETM48 | 0.5222 | 2 | DP10 (VH1) | 13b-10b, 13b-6b | 31 | 3 | |
| TETM86 | 0.8435 | 2 | DP10 (VH1) | 13b-10b, 13b-6b | 31 | 3 | ○ |

TABLE 7-continued

| Clone No. | ELISA Absorbance | H-chain DNA sequence ID NO: | VH1 classification | KL200 | Germ line VL | H-L gene combination ID NO. | The conduct of neutralization test |
|---|---|---|---|---|---|---|---|
| TETM89 | 0.9117 | 2 | DP10 (VH1) | 13b-10b, 13b-6b | 31 | 3 | |
| TETM49 | 1.2680 | 2 | DP10 (VH1) | VL library | 31 | 13 | ○ |
| TETM64 | 1.3011 | 2 | DP10 (VH1) | VL library | 31 | 14 | |
| TETM16 | 0.6521 | 3 | DP10 (VH1) | 13b-12b | 31 | 2 | ○ |
| TETM22 | 0.7705 | 3 | DP10 (VH1) | 13b-12b | 31 | 2 | ○ |
| TETM26 | 0.7478 | 3 | DP10 (VH1) | 13b-12b | 31 | 2 | ○ |
| TETM33 | 0.7425 | 3 | DP10 (VH1) | 13b-12b | 31 | 2 | ○ |
| TETM43 | 0.6578 | 3 | DP10 (VH1) | 13b-12b | 31 | 2 | ○ |
| TETM45 | 0.6392 | 3 | DP10 (VH1) | 13b-12b | 31 | 2 | ○ |
| TETM46 | 0.6056 | 3 | DP10 (VH1) | 13b-12b | 31 | 2 | ○ |
| TETM55 | 1.2684 | 3 | DP10 (VH1) | 13b-12b | 31 | 2 | |
| TETM15 | 1.9333 | 3 | DP10 (VH1) | L3BUM4 | 31 | 15 | ○ |
| TETM96 | 0.6639 | 4 | DP10 (VH1) | L3BUM6 | 31 | 16 | ○ |
| TETM73 | 1.0694 | 4 | DP10 (VH1) | 13b-10b, 13b-6b | 31 | 17 | |
| TETM80 | 1.1280 | 4 | DP10 (VH1) | VL library | 31 | 7 | |
| TETM83 | 0.9669 | 4 | DP10 (VH1) | VL library | 31 | 7 | |
| TETM03 | 0.7537 | 4 | DP10 (VH1) | 13b-1b | 31 | 18 | ○ |
| TETM71 | 1.1197 | 4 | DP10 (VH1) | L3BUM1 | 31 | 19 | |
| TETM19 | 0.8051 | 5 | DP10 (VH1) | L3BUM6 | 31 | 8 | ○ |
| TETM92 | 0.9295 | 5 | DP10 (VH1) | L3BUM6 | 31 | 8 | |
| TETM12 | 0.7983 | 5 | DP10 (VH1) | 13b-12b | 31 | 20 | ○ |
| TETM30 | 0.6473 | 5 | DP10 (VH1) | 13b-1b | 31 | 21 | ○ |
| TETM28 | 0.6622 | 5 | DP10 (VH1) | L3BUM1 | 31 | 22 | ○ |
| TETM37 | 0.6879 | 6 | DP10 (VH1) | L3BUM6 | 31 | 6 | ○ |
| TETM52 | 1.1214 | 6 | DP10 (VH1) | L3BUM6 | 31 | 6 | |
| TETM54 | 1.2341 | 6 | DP10 (VH1) | L3BUM6 | 31 | 6 | |
| TETM66 | 1.0685 | 6 | DP10 (VH1) | 13b-10b, 13b-6b | 31 | 23 | |
| TETM41 | 0.6138 | 6 | DP10 (VH1) | 13b-1b | 31 | 24 | ○ |
| TETM06 | 0.8287 | 7 | DP10 (VH1) | L3BUM6 | 31 | 5 | ○ |
| TETM60 | 1.5267 | 7 | DP10 (VH1) | L3BUM6 | 31 | 5 | |
| TETM62 | 1.2762 | 7 | DP10 (VH1) | L3BUM6 | 31 | 5 | |
| TETM82 | 1.2137 | 7 | DP10 (VH1) | L3BUM6 | 31 | 5 | |
| TETM08 | 0.8469 | 8 | DP10 (VH1) | L3BUM6 | 31 | 9 | ○ |
| TETM75 | 0.9548 | 8 | DP10 (VH1) | L3BUM6 | 31 | 9 | |
| TETM32 | 0.7325 | 9 | DP10 (VH1) | L3BUM6 | 31 | 25 | ○ |
| TETM94 | 0.8597 | 9 | DP10 (VH1) | 13b-12b | 31 | 26 | |
| TETM31 | 0.7118 | 10 | DP10 (VH1) | L3BUM6 | 31 | 27 | ○ |
| TETM74 | 1.1040 | 10 | DP10 (VH1) | VL library | 31 | 28 | |
| TETM34 | 0.6607 | 11 | DP10 (VH1) | L3BUM6 | 31 | 10 | ○ |
| TETM67 | 1.2017 | 11 | DP10 (VH1) | L3BUM6 | 31 | 10 | |
| TETM17 | 0.7207 | 12 | DP10 (VH1) | L3BUM6 | 31 | 11 | ○ |
| TETM29 | 0.7073 | 12 | DP10 (VH1) | L3BUM6 | 31 | 11 | ○ |
| TETM01 | 0.7729 | 13 | DP10 (VH1) | VL library | 31 | 29 | ○ |
| TETM13 | 0.6374 | 13 | DP10 (VH1) | 13b-10b, 13b-6b | 31 | 30 | ○ |
| TETM21 | 0.7280 | 14 | DP10 (VH1) | L3BUM6 | 31 | 31 | ○ |
| TETM56 | 1.3910 | 15 | DP10 (VH1) | VL library | 31 | 32 | |
| TETM58 | 1.3259 | 16 | DP77 (VH3) | k6-17b | DPK15 | 33 | |
| TETM69 | 0.9722 | 17 | DP10 (VH1) | L3BUM6 | 31 | 34 | |
| TETM88 | 2.1405 | 18 | DP14 (VH1) | VL library | DPK9 | 35 | ○ |
| TETM91 | 1.2441 | 19 | DP75 (VH1) | k1-5.b | DPK9 | 36 | |

4-10 Preparation of Fab-cp3-Type Antibodies to be Used for Testing the Neutralizing Activity It was examined whether the antibodies selected from the antibody library of the present invention by screening had the activity of neutralizing tetanus toxin. First, each of the 77 clones exhibiting activity as antibodies was pre-cultured before the antibody expression was induced. The bacterial cells preculture was combined with 2×YT medium (YTA) containing 1% glucose and 100 mg/ml ampicillin, and then incubated at 30° C. overnight. After the cells were further cultured in 0.1% glucose-YTA at 30° C. for 3 hours, 1M IPTG was added thereto. Culture was continued at 30° C. for 20 hours. The culture solution was centrifuged at 10,000 rpm for 5 minutes. The culture supernatant was collected and ammonium sulfate was added thereto at a final concentration of 60%. The mixture was agitated for one hour, and then centrifuged at 12,000 rpm for ten minutes. The resulting supernatant was discarded, and the precipitate was dissolved with PBS. The resulting solution was dialyzed against a 50 or more volume of PBS for 2 hours. This step was repeated three times. Then, the dialysate was transferred into an Eppendorf tube, followed by centrifugation of the tube at 15,000 rpm for 10 minutes at 4° C. After being filtered, the resulting supernatant was tested for the activity of neutralizing tetanus toxin.

4-11 Examination of the Neutralizing Activity

First, to evaluate the toxicity of antibody itself, 0.2 ml of the antibody solution prepared as described above was injected into the caudal vein and peritoneal cavity of mice. As the result, the antibody solution had no toxicity. In the subsequent experiments, one hour after the antibody was injected, 10 times as much dose of tetanus toxin as the minimal lethal dose (1 MLD or about 2 $LD_{50}$) for mouse was injected subcutaneously in an inside area of thigh of the hind legs of mice. As the result, partial neutralization (retarded onset of the symptoms caused by toxin; 4 to 7 days) was recognized in about half of the mice injected for testing each antibody. Mice, which were subjected to injection of a neutralizing antibody (standard tetanus antitoxin) or antibody without the neutralizing activity, showed tetanus toxin-specific paralysis, and then died in about two days.

Clones that exhibited partial neutralizing activity were: TETM1, TETM13, TETM26, and TETM96. Thus, the above-described findings demonstrate that useful antibodies having the neutralizing activity can be yielded by screening the antibody library of the present invention.

4-12 Sequence Determination for the Antibody Variable Region

As described above, the present inventors succeeded in preparing phages expressing antibody variable domains binding to and neutralizing tetanus toxoid (toxin).

Additionally, phage clones exhibiting similar neutralizing activity but having distinct nucleotide sequences were also obtained successfully by repeating the above-mentioned step. Specifically, clones of Nos. TETM13 and TETK36 were estimated to have strong neutralizing activity. The nucleotide sequences of the heavy chain and light chain of these phage clones, and the amino acid sequences encoded by the nucleotide sequences are shown below under the following SEQ ID Nos:

| Clone No. | Heavy chain | Light chain |
|---|---|---|
| TETM13 (nucleotide sequence) | 63 | 64 |
| TETM13 (amino acid sequence) | 81 | 82 |
| TETK36 (nucleotide sequence) | 65 | 66 |
| TETK36 (amino acid sequence) | 83 | 84 |

Example 5

Comparison of a Light Chain Gene Library without Selection and the KL200 Library Library performance was compared between the combinatorial library (AIMS3), which had been prepared by combining a light chain gene library without selection with a heavy chain, and the combinatorial library (AIMS1+AIMS2), which had been prepared by combining the light chain gene library KL200 with the heavy chain.

Firstly, the comparison showed that the antibody library AIMS1+AIMS2 according to the present invention was overwhelmingly superior in the number of clones selected. Clones selected from the light chain gene library AIMS1+AIMS2, which had been subjected to the selection, are 29 clones whose clone names are indicated in the column of "KL200" in Table 7 shown above. On the other hand, 7 clones were selected from AIMS3 (clones indicated by the label "VL library" in the column of "KL200" in Table 7). Namely, 80% or more (29/36) of the clones selected were derived from the library of the present invention, although the combinatorial library had prepared by combining the two libraries at a ratio of 1:1. Thus, the comparison of the numbers of phage particles obtained by screening demonstrated that the phage library prepared using KL200 is advantageous.

5-2 Comparison of the Activities of Phage Antibodies Obtained by Screening

Then, the selected antibodies were compared to one another with respect to the activity. Clones confirmed to have partial neutralizing activity in the test for the neutralizing activity described in Example 4-11 are the following four clones:

TETM1 (AIMS3)
TETM13 (AIMS1+AIMS2)
TETM26 (AIMS1+AIMS2)
TETM96 (AIMS1+AIMS2)

Specifically, 3 clones were selected from the library of AIMS1+AIMS2; 1 clone was selected from the library of AIMS3. This ratio is comparable to (29:7) which was the ratio of the number of clones obtained by screening. In addition, the three clones selected from the library derived form AIMS1+AIMS2 prepared according to the present invention contained TETM13 which had the strongest neutralizing activity. Thus, it was confirmed that screening of phage library prepared using the selected light chain library KL200 can select superior antibody efficiently from the aspect of the function.

Example 6

Selection of Phages Binding to a Specific Antigen from a Phage Library (Part 2)

The antibody library of the present invention was screened using diphtheria toxoid as an antigen. The library used in the screening was the same AIMS4 phage library as used in Example 4. This library comprised a mixed solution of AIMS3 (a combinatorial library prepared from the light chain gene library without selection and the heavy chain gene library) and AIMS1+AIMS2 (a combinatorial library prepared from the light chain gene library with selection and the heavy chain gene library).

6-1 Preparation of Test Tubes to be Used in the Screening

The concentration of the antigen (diphtheria toxoid) was adjusted to 20 μg/ml with PBS. A 3-ml aliquot of the antigen solution was added to each of three test tubes (Maxisorp; Nunc) and incubated at 4° C. for 18 hours to immobilize the antigen on the inner surface of the tubes. After antigen immobilization, the antigen solution was discarded, and 3 ml of PBS containing 2% skimmed milk was added to each tube. The tubes were incubated at 25° C. for one hour for blocking.

6-2 Screening Method

A 3-ml aliquot of the same phage library as used in Example 4 ($1\times10^{14}$ CFU) in 9 ml of BBS containing 2% skimmed milk and 0.1% Tween-20 was added to each of the three antigen-immobilized test tubes. The tubes were incubated at 25° C. for 2 hours, and then washed 4 times with PBS containing 0.1% Tween-20, 4 times with PBS and once sterilized extra pure water (prepared by MilliQ).

Then, phage particles bound to the antigen-immobilized test tubes were recovered by the procedure as described below. Specifically, 3 ml of 0.1 M triethylamine (pH 12.3) was added to each test tube and the tubes were incubated while being rotated with a rotator at room temperature for 20 minutes to dissociate the phage particles from tube surface. Then, 1.1 ml of 1 M Tris-HCl buffer (pH6.8) was added to the tubes to neutralize the solution. The neutralized phage solutions were collected.

6-3 Amplification of the Collected Phages

The collected phage solutions were treated by the same procedure as in Example 4-3 and 4-4 as follows:

(a) the phage was infected to *E. coli* cells;
(b) helper phage was infected to *E. coli* cells; and
(c) the resulting phage particles were collected.

The washing was carried out by the same procedure as used in the screening in Example 4-4.

6-4 Evaluation of phage screening method The nucleotide sequences of the light chains from clones isolated in this experiment, which were confirmed to be expressed, were determined to reveal the origins thereof. As the result, 20 clones were derived from (AIMS1+AIMS2); 16 clones were selected from (AIMS4).

Further, it was examined whether these clones contained clones of practical utility having high activity. The neutralizing activity of antibody against diphtheria toxin was determined quantitatively by the Cell Culture Method (CCM) using culture cells. The CCM method was practiced as follows.

The standard antitoxin solution used was prepared by dissolving an ample of domestic standard diphtheria antitoxin (Lot. 9) in PBS containing 0.2 w/v % gelatine, and adjusting the concentration of the antitoxin to 10 IU/ml with 3% cs culture medium (containing 1,000 ml of purified water containing 9.4 g of Eagle. MEM, 0.3 g of L-glutamine, 200,000 units/2 ml of penicillin, 0.1 g (titer)/0.5 ml of streptomycin, 3.0 g of glucose, 30 ml of fetal calf serum, 3 ml of 1% phenol red, and 20 ml of 7 w/v % sodium bicarbonate).

The solution of toxin being tested was prepared by dissolving a vial (Lf/vial=2.5; $CD_{50}$/vial=1.6×10$^5$) of diphtheria toxin (Lot. M59) in PBS containing 0.2 w/v % gelatine. The concentration of the toxin was adjusted to 1.6×10$^4$ $CD_{50}$/ml with 3% cs culture medium. The toxin solution was used after being further diluted with 3% cs culture medium. The cell used was VERO cell, which was passaged in 7% cs culture medium (1,000 ml of purified water containing 9.4 g of Eagle MEM, 0.3 g of L-glutamine, 200,000 units/2 ml of penicillin, 0.1 g (titer)/0.5 ml of streptomycin, 70 ml of fetal calf serum, 3 ml of 1% phenol red, and 20 ml of 7 w/v % sodium bicarbonate).

Serial dilutions of (25 µl each) of test antibody and standard antitoxin were prepared with 3% cs culture medium in a 96-well microtiter plate, and then the diphtheria toxin (25 µl) prepared as described above was added thereto. The plated was incubated at 37° C. for 30 minutes, and 50 µl of suspension of VERO cell, where the cell density had been adjusted to 3×10$^5$ cells/ml with 3% cs culture medium, and 100 µl of 3% cs culture medium were added thereto. After being sealed, the plate was incubated in an incubator at 37° C. for 4 days. The endpoint for the standard antitoxin in this assay system was determined based on the changed color of pH indicator (reference color was orange). The antitoxin titer of a test antibody was defined as a value obtained by multiplying the endpoint antitoxin titer by the dilution fold corresponding to the endpoint of the test antibody. The endpoint of standard antitoxin in this assay system was determined to be 0.0046 IU/ml.

According to the result, one of the 43 clones tested by CCM method had the activity (0.0520 IU/ml) of neutralizing diphtheria toxoid (toxin). On the other hand, no clones having activity was isolated from AIMS3 (the light chain gene library prepared without selection). These findings clearly indicate that the antibody library AIMS1+AIMS2 prepared according to the present invention was a high-performance library excellently mimicking the in vivo antibody diversity.

The present inventors also isolated a phage clone (DTD10) allowing the production of an antibody binding to and neutralizing diphtheria toxin. The nucleotide sequences of the heavy chain and light chain of the above-mentioned phage clone, and the encoded amino acid sequences are shown under the following SEQ ID NOs:
The nucleotide sequence of heavy chain of DTD10/SEQ ID NO: 61; the amino acid sequence/SEQ ID NO: 79
The nucleotide sequence of light chain of DTD10/SEQ ID NO: 62; the amino acid sequence/SEQ ID NO: 80.

Example 7

Selection of Phages Binding to a Specific Antigen from a Phage Library (Part 3)

The antibody library of the present invention was screened using antigens derived from influenza virus. Names of influenza virus strains are abbreviated hereinafter as follows (virus subtypes are shown in parentheses).

| Virus strain name | Abbreviation |
| --- | --- |
| A/New Caledonia/20/99 strain (H1N1) | New Caledonia strain (H1N1) |
| A/Sydney/5/97 strain (H3N2) | Sydney strain (H3N2) |
| A/Okuda/57 strain (H2N2) | Okuda strain (H2N2) |
| A/Beijing/262/95 strain (H1N1) | Beijing strain (H1N1) |

7-1 Purification of Influenza Virus-Derived Antigen

An antigen derived from influenza virus was purified by a method known to those skilled in the art as follows. A vaccine strain purchased from the National Institute of Infectious Diseases was inoculated to embryonated hen eggs. The eggs were incubated at 33 to 35° C. for 2 days, and then allowed to stand still in a cold room at 4° C. overnight. Thus infected chorioallantoic fluid was collected according to a conventional method, and then concentrated by ultra-filtration or another commonly used biochemical method. The virus sample was purified by sucrose density gradient centrifugation. Specifically, the concentrated virus particles were ultra-centrifuged with a sucrose density gradient of 0 to 60% at 35,000 rpm. The fraction at a sucrose density of about 40% was collected. The fraction containing virus particles was treated with ether (ether-inactivated virus). Then, formalin was added to the fraction. The sample was further purified by sucrose density gradient centrifugation to obtain a purified antigen of influenza virus.

7-2 Isolation of Phage Antibodies Using Beijing Strain (H1N1)

7-2-1 Preparation of Test Tubes to be Used in the Screening

The antigen of influenza virus extracted from Beijing strain (H1N1) by the procedure as described in Example 7-1 was dissolved in PBS at a final concentration of 12.5 µg/ml. A 4.5-ml aliquot of the antigen solution was added to an immuno-tube (Polysorp), and while being inverted gently the tube was incubated at 4° C. for 18 hours or at 25° C. for two hours to immobilize the influenza virus antigen on the inner surface of immuno-tube. After the solution of influenza virus antigen was discarded, 4.5 ml of PBS containing 2% skimmed milk was added to the tube. To avoid non-specific reactions, blocking reaction was carried out by incubating the tube at 4° C. for 18 hours or at 25° C. for one hour.

7-2-2 Screening Method 4.5 ml of a suspension of the AIMS4 phage library, which was the same library as used in Example 4, in PBS containing 2% skimmed milk was added to the immuno-tube, on which the antigen had been immobilized, prepared by the procedure as described above. While being inverted the tube was incubated at 25° C. for 2 hours to contact the AIMS4 phage library with the influenza virus antigen immobilized in the inner surface of the tube.

After being contacted as described above, the phage solution was discarded and the tube was washed to remove unbound phage particles from the tube. The washing buffer used and the number of washing repetitions are indicated in Table 8.

TABLE 8

| Screening | Washing solution | | |
|---|---|---|---|
| | PBS + T | PBS | Distilled water |
| 1st | 4 | 4 | 1 |
| 2nd | 6 | 6 | 1 |
| 3rd | 13 | 13 | 1 |

PBS + T: PBS + 0.1% Tween 20

Then, 4.5 ml of 0.1M triethylamine (pH 12.3) was added to the tube, and while being inverted the tube was incubated at room temperature for 20 minutes to dissociate the phage particles from the tube. The solution containing the dissociated phage particles was transferred into a fresh tube, and immediately 1.1 ml of 1M Tris-HCl (pH 6.8) was added thereto to neutralize the solution.

7-2-3 Amplification of Recovered Phage

*E. coli* DH12S cells had precultured until OD at 600 nm reach 0.5. The phage liquid prepared in the above-described step was added to 50 ml (30 ml in the secondary or subsequent screening) of the suspension of *E. coli* DH12S cells (in 2×YT medium). The mixture was incubated at 37° C. for one hour while being shaken to infect the phages having antigen-binding activity to the *E. coli* cells.

The above-mentioned *E. coli* solution was diluted as described below; the final volume was 500 ml. (A 3-liter flask was used.)

| | |
|---|---|
| *E. coli* solution | 61.25 ml |
| 2×YT | 425 ml |
| 40% glucose | 12.5 ml (final concentration: 1%) |
| 100 mg/ml ampicillin | 0.5 ml (final concentration: 100 µg/ml) |

The above-mentioned *E. coli* diluted solution was further incubated at 37° C. for 1 to 2 hours, and the flask was allowed to stand at 4° C. overnight.

The flask stored overnight was again incubated at 37° C. while being shaken. When OD at 600 nm reached 0.5, the culture solution was transferred into sterilized centrifugal tubes. Then, the tubes were centrifuged at 5,000 rpm for 10 minutes at 4° C. to collect the bacterial cells.

The collected bacterial cells were suspended in 1 to 2 ml of 2×YT medium. An aliquot of the suspension was stored as a glycerol stock (final concentration of glycerol was 20%).

The remaining bacterial cells were suspended in 300 ml (150 ml and 50 ml in the 3rd and 4th screenings, respectively) of 2×YT medium containing 100 µg/ml ampicillin, and then cultured. When OD at 600 nm reached 0.5, the helper phage M13K07 solution, which corresponded to ¹/₁₀ volume of the culture solution, was added to the culture, and incubation was continued at 37° C. for one hour while being shaken to infect the helper phage.

An aliquot of the above-mentioned culture solution was plated on an agar plate containing 2×YT medium to estimate the number of helper phage-infected *E. coli* cells. A fresh culture medium (900 ml of 2×YT medium containing 100 µg/ml ampicillin and 70 µg/ml kanamycine, which was pre-warmed at 37° C.) was added to the remaining culture. The mixture was incubated while being shaken at 37° C. overnight, and then helper phage-infected *E. coli* cells were selected.

After overnight culture, the culture was centrifuged at 7,000 rpm for 10 minutes at 4° C. (using sterilized 1,000-ml centrifugal tubes) to precipitate the bacterial cells, and the resulting supernatant was collected. A 20% polyethylene glycol solution containing 2.5 M NaCl, which corresponded to ⅕ volume of the supernatant, was added to the supernatant. The mixture was allowed to stand still at room temperature for 20 minutes, and then centrifuged at 8,000 rpm for 15 minutes at 4° C. to precipitate and collect the phage particles.

The supernatant was discarded carefully not to disturb the pellet, and then the pellet was suspended in sterilized PBS that corresponded to ¹/₁₀ volume of the culture solution. Then, 20% polyethylene glycol solution containing 2.5M NaCl, which corresponded to ⅕ volume of PBS, was added to the suspension. The resulting mixture was centrifuged at 10,000 rpm for 20 minutes at 4° C. (using sterilized 200-ml centrifugal tubes) to precipitate phages particles. Thus, impurities were removed from the phage sample. PBS containing 0.05% $NaN_3$ which corresponded to ¹/₁₀₀ volume of the culture solution was added to the pellet, and the phage particles were suspended by shaking for about two hours using a shaker.

The phage sample prepared in the above-mentioned step was further screened twice. However, the screening yielded only antibodies reactive to NP protein of influenza virus. These antibodies had no activity of neutralizing influenza virus.

7-3 Isolation of Subtype-Specific Phage Antibodies Using New Caledonia Strain (H1N1)

The epitopes which influenza-neutralizing antibodies recognize are believed to be present in HA protein on the surface of virus particles. HA protein has many sequence variations among virus strains. Thus, virus strain-specific antibodies were isolated to obtain neutralizing antibodies.

7-3-1 Preparation of an Antibody Library from which Anti-NP Antibodies have been Removed by Absorption Ether-treated inactivated virus particles were prepared using Okuda strain (H2N2) of influenza virus according to the procedure as described in Example 7-1. The inactivated virus particles were suspended in PBS at a concentration of 20 μg/ml, and 3-ml aliquots of the suspension were added to each of three reaction tubes. The tubes were incubated at 4° C. for 18 hours. The suspension was discarded and PBS containing 2% skimmed milk was added to the tubes. The tubes were incubated for one hour. Then, PBS containing AIMS4 library LOT 000614 and 2% skimmed milk was added to the three tubes; the titer of the library used was $1\times10^{14}$ CFU/9 ml. The tubes were incubated at room temperature (25° C.) for two hours while being agitated. The library after incubation was used as an AIMS4 antibody library from which anti-NP antibodies had been removed by absorption.

7-3-2 Screening with Antigens of Interest Derived from New Caledonia Strain (H1N1)

Formalin-treated inactivated virus particles of New Caledonia strain (H1N1) were prepared by the same procedure as described above, and suspended in PBS at a concentration of 100 μg/ml. 3-ml aliquots of the suspension were added to each of three reaction tubes. The tubes were incubated at 4° C. for 18 hours. The suspension was discarded and PBS containing 2% skimmed milk was added to the tubes to prevent non-specific reaction. The tubes were incubated for one hour. Then, the AIMS4 library, from which anti-NP antibodies had been removed by absorption, prepared in Example 7-3-2 was added to the three tubes. The tubes were incubated at 25° C. for two hours while being agitated. After incubation, the tubes were washed with PBS; the number of washing repetitions is shown below in Table 9.

After washing, 3 ml of 0.1M triethylamine (pH 12.3) was added to each tube. The tubes were incubated at room temperature for 20 minutes while being agitated with a rotator to dissociate phage particles from the antigen. 1 ml of 1M Tris- HCl (pH6.8) was added to the tubes to neutralize the liquid (recovery of phage particles bound to the antigen). *E. coli* DH12S cells were precultured in 50 ml of 2×YT medium until OD at 600 nm reached 0.5 to 1.0. Then, the antigen-bound phage particles were incubated with the *E. coli* cells at 37° C. for one hour while being shaken to infect the phage to the bacteria.

The recovered phage particles were amplified by the same procedure as described in Example 7-2-3. After amplification, anti-NP antibodies were removed by absorption according to the same procedure as described in Example 7-3-1. The titer of the phage solution was determined as described below. Then, screening was carried out in the same way by using the solution of amplified phage particles. The screening step was repeated three times.

7-3-3 Determination of Phage Titer

The titer of phage solution to be used in the next round of screening was previously determined by the procedure as described below.

A serial dilution was prepared as follows:
[1] $1\times10^{-2}$ dilution: 10 µl of phage solution+990 µl of PBS
[2] $1\times10^{-4}$ dilution: 10 µl of the dilute in [1]+PBS 990 µl
[3] $1\times10^{-6}$ dilution: 10 µl of the dilute in [2]+990 µl of PBS
[4] $1\times10^{-8}$ dilution: 10 µl of the dilute in [3]+990 µl of PBS
[5] $1\times10^{-10}$ dilution: 10 µl of the dilute in [4]+990 µl of PBS
[6] $1\times10^{-12}$ dilution: 10 µl of the dilute in [5]+990 µl of PBS 990 µl of DH12S was combined with each of 10-µl aliquots of the dilutes prepared in [4], [5], and [6] in the serial dilution. The mixtures were incubated at 37° C. for one hour for infection, and 100-µl aliquots thereof were plated on LBGA plates, followed by incubation at 30° C. for 18 to 24 hours. The resulting colonies grown were counted.

When the number of colonies grown was 50 colonies/plate or more, such plates were selected from those prepared in [4], [5], and [6]; the colony counts in such plates were adopted as data.

A formula for determining the phage titer for the next-round screening (in the case described in [4])

Phage titer=(the total number of colonies/plate)×(1× $10^8$)×$10^3$ phages/ml

TABLE 9

New Caledonia strain (H1N1) after being absorbed with Okuda strain (H2N2)

| Screening | The number of washing repetitions | Input* | Output** | 1/(Input/Output) |
|---|---|---|---|---|
| 1st | 4 | $1.0 \times 10^{14}$ | $9.1 \times 10^{8}$ | $1/(1.1 \times 10^{6})$ |
| 2nd | 8 | $4.6 \times 10^{13}$ | $1.1 \times 10^{8}$ | $1/(5.1 \times 10^{6})$ |
| 3rd | 16 | $4.0 \times 10^{13}$ | $4.7 \times 10^{10}$ | $1/(8.5 \times 10^{2})$ |

*From the result obtained in Example 7-3-3; unit: (cfu/ml).
**Calculated from the number of phage particles prior to amplification, which were recovered in the screening step in Example 8-3-2; unit: (cfu/ml).

7-4 Method for Isolating Neutralizing-Antibodies Specific to the H3N2 Subtype 7-4-1 Screening with Antigens of Interest Derived from Sydney Strain (H3N2)

Formalin-Treated Inactivated Influenza Virus Particles of Sydney strain (H3N2) were suspended in PBS at a concentration of 100 µg/ml, and the suspension (4.5 ml per tube) was added to three Nunc Polysorp tubes. The tubes were incubated at 4° C. for 18 hours. The suspension was discarded and PBS containing 2% skimmed milk was added to the tubes. The tubes were incubated for one hour for blocking. Then, the AIMS4 library, from which anti-NP antibodies had been removed by absorption, prepared in Example 7-3-1 was added to the three tubes. The tubes were incubated at room temperature (25° C.) for two hours while being agitated using a rotator.

After incubation, the tubes were washed with PBS; the number of washing repetitions is shown below in Table 10.

After washing, 3 ml of 0.1M triethylamine (pH 12.3) was added to each tube. The tubes were incubated at room temperature for 20 minutes while being agitated with a rotator to dissociate phage particles from the antigen. 1 ml of 1 M Tris-HCl (pH6.8) was added to the tubes to neutralize the solution (recovery of phage particles bound to the antigen).

*E. coli* DH12S cells were pre-cultured in 50 ml of in 2×YT medium until OD at 600 nm reached 0.5 to 1.0. Then, the antigen-bound phage particles were incubated with the *E. coli* cells at 37° C. for one hour while being shaken to infect the phage to the bacterial cells.

The recovered phage particles were amplified by the same procedure as described in Example 7-2-3. After amplification, anti-NP antibodies were removed by absorption according to the same procedure as described in Example 7-3-1. After the titer of the phage solution was determined by the same method as described in 7-3-3 (Table 11), then screening was carried out in the same way by using the solution of amplified phage particles. The screening step was repeated three times.

TABLE 10

Sydney strain (H3N2) after being absorbed with Okuda strain (H2N2)

| Screening | The number of washing repetitions | Input* | Output* | 1/(Input/Output) |
|---|---|---|---|---|
| 1st | 4 | $1.0 \times 10^{14}$ | $1.0 \times 10^{9}$ | $1/(1.0 \times 10^{5})$ |
| 2nd | 8 | $4.0 \times 10^{13}$ | $3.3 \times 10^{7}$ | $1/(1.2 \times 10^{6})$ |
| 3rd | 16 | $5.6 \times 10^{13}$ | $2.8 \times 1010$ | $1/(2.6 \times 10^{3})$ |

*From the result obtained in Example 7-3-3; unit: (cfu/ml).
**Calculated from the number of phage particles prior to amplification, which were recovered in the screening step in Example 7-3-2; unit: (cfu/ml).

7-5 Evaluation of Phage Antibodies Neutralizing Influenza Virus 7-5-1 Induction of the Expression of Fab-Type Antibody The present inventors have found that when phage-infected *E. coli* is cultured for a long period after induction of the expression, not phage but the Fab-type antibody is secreted from *E. coli* into the culture supernatant.

*E. coli* cells from the colonies of phage-containing *E. coli* obtained from the steps in Example 7-2-3, 7-3-3, and 7-4-1 were inoculated to 2×YT medium containing 0.1% glucose and 100 µg/ml ampicillin. The bacterial cells were cultured at 30° C. When OD at 600 nm reached about 0.5, IPTG was added to the culture at a final concentration of 1 mM. Then, culture was continued at 30° C. for 18 hours to induce the expression of phage antibodies.

A glycerol stock of *E. coli* was prepared by adding glycerol at a final concentration of 30% to another culture prepared by incubating for 18 hours without adding IPTG.

7-5-2 Confirmation of Characteristics of Fab-Type Antibody by ELISA 1.5 ml of the culture solution, in which the Fab-type antibody had been expressed, prepared in Example 7-5-1 was placed in a tube, and centrifuged at 10,000 rpm for 5 minutes at 4° C. The resulting culture supernatant was collected, and $NaN_3$ was added thereto at a final concentration of 0.1%. The supernatant was used as an ELISA sample.

Then, to each well of a 96-well ELISA plate, 100 µl of the antigen was added at the same concentration as used in the screening. The plate was incubated at 4° C. for 18 hours to immobilize the antigen on the surface of each well of the plate. Then, 200 µl of PBS containing 2.5% BSA was added to each well, and the plate was incubated at 4° C. for 18 hours for blocking.

Before the ELISA test was conducted, the blocking solution was discarded and the plate was washed once with PBS. 100 µl of the supernatant of the culture where the induction was carried out in Example 7-5-1 was added to each well. After the plate was incubated at 25° C. for one hour, the wells were washed 4 times with PBS. After A POD (peroxidase)-conjugated anti-human IgG (MBL; Cat. #206 LOT150) was diluted 5,000 times, a 100-µl aliquot of the solution was added to each well. The plate was incubated at 25° C. for one hour (or at 37° C. for one hour, while being shaken at room temperature at 250 rpm for 30 minutes). Then, the plate was washed four times with PBS, and 100 µl of a substrate solution was added to each well. The substrate solution used was prepared as follows: 12 ml of $H_2O_2$ was added at a final concentration of 0.01% to 0.1 M citric acid-disodium phosphate (pH 5.1), and then a tablet of OPD (Wako, Biochemical Grade, Code #158-01671) was added thereto. After 15 to 30 minutes, the absorbance (OD at 492 nm) of each well was measured with a plate reader.

According to the result obtained by ELISA, it was revealed that neutralizing antibodies exhibiting strain-specific reactivity were 1 clone specific to New Caledonia strain (H1N1) and 3 clones specific to Sydney strain (H3N2). The reactivities of these four clones are indicated in Table 12.

TABLE 11

| Antigen | New Caledonia strain (H1N1) after being absorbed with Okuda strain (H2N2) | Sydney strain (H3N2) after being absorbed with Okuda strain (H2N2) |
|---|---|---|
| The number of tested colonies | 48 | 48 |
| Having no gene deletion * | 37 | 29 |
| ELISA positive | 35 | 27 |
| Specific to strain-dependent antigen | 1 | 2 |

* Having no sequence deletion, according to the result of nucleotide sequencing of gene

TABLE 12

| | | Antigen-immobilized plate | | |
|---|---|---|---|---|
| Antigen used in screening | Clone No. | New Caledonia strain (H1N1) | Okuda strain (H2N2) | Sydney strain (H3N2) |
| New Caledonia strain (H1N1) | NC1 | 1.991 | 0.052 | 0.098 |
| Sydney strain (H3N2) | SY39 | 0.090 | 0.080 | 1.612 |
| Sydney strain (H3N2) | SY47 | 0.080 | 0.056 | 2.859 |
| Control Anti-NP | IF8 | 2.966 | 2.438 | 2.923 |
| Negative control | | 0.090 | 0.057 | 0.065 |

7-5-3 Plasmid Purification and Sequencing

*E. coli* cells were cultured in 2×YT medium (containing 0.1% glucose and 200 µg/ml ampicillin) overnight, and plasmids were purified from the cells using a DNA extractor (PI-50; Kurabo) according to the supplier's instruction. The purified plasmids were treated with Rnase, which was added at a final concentration of 20 µg/ml, and then treated with phenol-chloroform. The plasmids were stored at −20° C. or lower temperature.

The sequences of antibody genes corresponding to the obtained phage antibodies were determined by sequencing. Sequencing was carried out by the dideoxy method using a DNA sequencer (Aloka; L1-COR4200L (S)-2); the reagent used was thermo sequence kit (US78500; Amersham Pharmacia).

The sequencing primers used for the heavy chain and light chain were as follows:

```
                                          (SEQ ID NO: 97)
heavy chain: T7 Promoter IDR700 dye-labeled
primer 50 µl
5'TAATACgACTCACTATAggg3' (20 mer)
```

```
                                          (SEQ ID NO: 98)
  light chain: custom primer 3'huCH1J
     IDR800 dye-labeled primer 50 µl
  5'ATTAATAAgAgCTATCCCgg3' (20 mer)
```

The number of clones having no sequence deletion, which was determined by nucleotide sequencing for the genes, is indicated in Table 11. Genes corresponding to strain-specific clones and amino acid sequences are shown in Sequence Listing.

7-5-4 Neutralization Test for Influenza Virus

A suspension of MDCK cells was aliquoted into each well of a 96-well flat-bottomed plate (Corning; cat. #3596) (approximately $10^4$ cells/well). The plate was incubated in a $CO_2$ incubator at 37° C. so that the bottom surface of each well could be covered with a monolayer sheet of cell. On the next day, the respective antibodies to be tested, after being diluted 4 times with MEM culture medium containing 0.2% BSA (fraction V; Sigma Chemical Co.) were added to wells of a 96-well round-bottomed plate. 25 µl of an influenza virus solution ($4 \times 10^4$ FFU/ml) diluted with MEM culture medium containing 0.2% BSA was combined with 25 µl of the diluted antibody solution or control solution. The mixture was incubated at 37° C. for 60 minutes.

25 µl each of the mixed solutions was added to the MDCK cells in wells of the above-mentioned 96-well plate. The virus particles were allowed to adhere to the cells by incubating the plate at 37° C. for 60 minutes.

After this treatment, each well was washed with PBS. 100 µl of MEM culture medium containing 0.5% tragacanth gum and 5 µg/ml trypsin was added to each well, and then culture was continued at 37° C. for 24 hours.

After cultivation, each well was washed with PBS. 100% ethanol was added to each well, and then the plate was incubated at room temperature for 10 minutes. The wells were dried using a hair dryer. After PAP staining, the number of focuses was determined.

The neutralizing activity of an antibody was defined as a decrement of the number of focuses relative to that without adding any antibody (positive control).

As seen below in Table 13, the Fab-type antibodies corresponding to Clone Nos: NC1, SY39, and SY47 exhibited significantly high activity of neutralizing influenza virus.

TABLE 13

| Clone No. (Dilution fold) | New Caledonia strain (H1N1) | | Sydney strain (H3N2) | |
|---|---|---|---|---|
| | Virus titer (FFU/well) | Reduction of focus count (%) | Virus titer (FFU/well) | Reduction of focus count (%) |
| NC1 (1:1) | 26 | 71.3 | ND | |
| SY39 (1:1) | ND | | 3 | 94.9 |
| SY47 (1:1) | ND | | 12.5 | 78.6 |
| IF8 (1:1) | 71 | 21.5 | 66 | 0 |
| *AS1296 (1:100) | 43.5 | 51.9 | 1 | 98.3 |
| *C179 (1:100) | 12.5 | 98.3 | ND | |
| *a-AichH3 (1:100) | ND | | 2.5 | 95.7 |
| Positive control | 90.5 | 0 | 58.5 | 0 |

FFU: Focus Forming Unit
ND: Not Done
*Antibody known to have neutralizing activity Reduction of focus count (%) =

$$\frac{\text{(Titer of positive control)} - \text{(Titer of sample virus)}}{\text{(Titer of positive control)}} \times 100$$

(Titer: FFU/well)

7-5-5 Conclusions Concerning the Evaluation

As predicted, the antibodies of virus strain-specific phage antibody clones exhibited high activity of neutralizing influenza virus. Namely, the clones are: clone NC1 specific to New Caledonia strain (H1N1); clones SY39 and SY47 specific to Sydney strain (H3N2). The nucleotide sequences of the heavy chain and light chain in these phage clones, and the amino acid sequences encoded by the same are shown below under the following SEQ ID NOs:

| Clone No. | Heavy chain | Light chain |
|---|---|---|
| NC1 (nucleotide sequence) | 67 | 68 |
| NC1 (amino acid sequence) | 85 | 86 |
| SY39 (nucleotide sequence) | 69 | 70 |
| SY39 (amino acid sequence) | 87 | 88 |
| SY47 (nucleotide sequence) | 71 | 72 |
| SY47 (amino acid sequence) | 89 | 90 |

Because the antibody genes are already available and characterized, when intending to use practically these types of antibody variable regions for clinical purposes, one can construct complete immunoglobulin molecules from the antibody variable regions or conjugate the regions with an enzyme by a relatively simple method. Furthermore, the activity can be improved by introducing artificial mutations.

Example 8

Selection of Phages Binding to a Specific Antigen from a Phage Library (Part 4)

The antibody library of the present invention was screened using antigens derived from varicella-zoster virus (VZV).

8-1 Isolation of Phage Antibodies Reactive to VZV 8-1-1 Preparation of Test Tubes to be Used in the Screening VZV-infected human embryonic lung cell (HEL) was available from some public organizations. The cells in PBS were lysed by sonication. The proteins gE and gH were prepared from the lysate according to the method of Shiraki et al. (Shiraki, K., Takahashi, M. J. Gen. Virol. 1982, 61: 271-5). A solution of gH protein whose concentration was adjusted to 25 μg/ml was used as a VZV antigen solution. A 4.5-ml aliquot of the VZV antigen solution was added to an immuno-tube (Maxisorp), and while being inverted gently the tube was incubated at 4° C. for 18 hours or at 25° C. for two hours to immobilize the VZV antigen on the inner surface of immuno-tube. After the VZV antigen solution was discarded, 4.5 ml of PBS containing 2% skimmed milk was added to the tube. To avoid non-specific reactions, blocking reaction was carried out by incubating the tube at 4° C. for 18 hours or at 25° C. for one hour.

8-1-2 Screening Method 4.5 ml of a suspension of the AIMS4 phage library in PBS containing 2% skimmed milk was added to the immuno-tube, on which the antigen had been immobilized, prepared by the procedure as described above. While being inverted the tube was incubated at 25° C. for 2 hours to contact the AIMS4 phage library with the VZV antigen immobilized in the inner surface of the tube.

After being contacted as described above, the phage solution was discarded and the tube was washed to remove unbound phage particles from the tube. The washing buffer used and the number of washing repetitions are indicated in Table 14. The term "washing" refers to a series of treatments comprising adding a buffer, inverting the tube containing the buffer, and discarding the buffer.

TABLE 14

| | Washing | Input | Output | In/Out |
|---|---|---|---|---|
| 1st | 2% skim – PBS 4 times + PBS once | $1.3 \times 10^{14}$ | $1.4 \times 10^9$ | $9.6 \times 10^4$ |
| 2nd | 2% skim – PBS 5 times + PBS 15 times | $3.1 \times 10^{13}$ | $9.3 \times 10^4$ | $3.3 \times 10^8$ |
| 3rd | 2% skim – PBS 5 times + PBS 20 times | $4.6 \times 10^{13}$ | $3.6 \times 10^6$ | $1.3 \times 10^7$ |
| 4th | 2% skim – PBS 5 times + PBS 20 times | $5.0 \times 10^{13}$ | $2.5 \times 10^8$ | $2.0 \times 10^5$ |

Then, 4.5 ml of 0.1M triethylamine (pH 12.3) was added to the tube, and while being inverted the tube was incubated at room temperature for 20 minutes to dissociate the phage particles from the tube. The solution containing the dissociated phage particles was transferred into a fresh tube, and immediately 1.1 ml of 1 M Tris-HCl (pH 6.8) was added thereto to neutralize the solution.

Amplification of recovered phage particles was achieved by the same procedure as described in Example 7-2-3, and then the titer of the phage solution after amplification was determined by the same method as described in Example 7-3-3.

The screening step as described above was repeated three times.

8-2 The Step of Assessing the Antigen-Binding Activity Using Culture Supernatants of E. coli Cells by ELISA The antigen-binding activity was assessed by the same ELISA method as used in Example 7-5-2. The VZV antigen was dissolved in PBS to a concentration of 12.5 μg/ml. A 100-μl aliquot of the solution was added to each well of a 96-well plate, and the plate was incubated at 4° C. for 18 hours to immobilize the antigen on the surface of each well of 96-well plate. Then, 200 μl of 2.5% BSA was added to each well and the plate was incubated at 4° C. for 18 hours for blocking.

After blocking, the blocking solution of the 96-well plate was discarded. The plate was washed once with PBS, and then 100 μl of culture supernatant of phage-infected E. coli cells prepared by the same procedure as in Example 8-5-2 was added to each well. The plated was incubated at 25° C. for one hour. The subsequent steps were conducted in the same way as in Example 8-5-2.

As seen in the Table indicated above, the recovery rate (output) was increased in the screening for the third time, and thus 12 clones were tested for the activity by ELISA. According to the result, 1 clone exhibited strong activity. Then, the fourth screening was carried out and 48 clones were tested by ELISA. The clones were all positive while the activities were weak.

8-3 Comparison of the Reactivity Between gE and gH, and Sequencing

Antibodies against sugar chains were predicted to be reactive to other moieties of virus particle, and to have low specificity and low neutralizing activity. Thus, ELISA was also carried out for antibodies against gE abundantly containing glycoprotein. Thus, antibodies having significant reactivity to gE were excluded based on the result obtained.

Based on this criterion, 29 clones having significant reactivity to gH were selected (Table 15), and the nucleotide sequences of the clones were analyzed (sequenced) by the same procedure as described in Example 7-5-3. Sequencing revealed 16 types of nucleotide sequences. The culture supernatants of representative clones were collected and concentrated with saturated ammonium sulfate. After dialysis, the samples were tested for the neutralizing activity.

TABLE 15

| Type of sequence | Clone name | Comparison of binding activity between gH and gE by ELISA |
|---|---|---|
| 1 | VZ9 | gH ≦ gE low |
| 2 | VZ10, VZ34, VZ75 | gH > gE low |
| 3 | VZ11 | gH >> gE |
| 4 | VZ13, VZ15, VZ19 | gH < gE |
| 5 | VZ24 | gH > gE low |
| 6 | VZ36 | gH ≦ gE high |
| 7 | VZ49, VZ66 | gH = gE |
| 8 | VZ60, VZ76 | gH > gE low |
| 9 | VZ64, VZ33, VZ58 | gH ≧ gE |
| 10 | VZ68 | gH < gE |
| 11 | VZ77 | gH > gE low |
| 12 | VZ85 | gH < gE |
| 13 | VZ86, VZ96 | gH ≧ gE low |
| 14 | VZ89,VZ80,VZ81 | gH = gE low |
| 15 | VZ94,VZ62 | gH > gE low |
| 16 | VZ100 | gH ≧ gE |
| 17 | VZ102 | gH > gE low |

Underline: clone tested for neutralizing activity;
Bold italic: clone found to have strong neutralizing activity.

8-4 Neutralization Test of Obtained Antibodies for VZV Virus 8-4-1 Preparation of Cell-Free Varicella-Zoster Virus (VZV Oka Strain) to be Used in the Test When approximately 50% of human embryonic lung cells (HEL) being cultured showed alterations specific to infected cells (CPE: cytopathic effect), the cells were harvested using PBS containing EDTA (0.04 to 0.1%) (without trypsin) and centrifuged at a low speed. The cells harvested were suspended in SPGC storage (sterilized PBS containing 5% sucrose, 0.1% sodium glutaminate and 10% fetal calf serum).

The cells were lysed by sonication or freeze-and-thaw plus sonication to release the virus particles. The lysate was centrifuged at 3,000 rpm for 10 minutes, and the resulting supernatant was used as a virus solution, which was stored at −85° C. Using an aliquot of the solution, the titer (infectivity) was determined with HEL cells. Specifically, the virus solution was diluted appropriately with SPGC storage, and a 0.2-ml aliquot of the dilute was scattered onto HEL cells that had been placed in a 6-cm dish to inoculate the virus to the cells. The inoculation was achieved as follows: the virus solution was being scattered repeatedly back and forth equally onto the HEL cells for one hour so that the cells could be covered with the virus solution and the cell surface was not dried. After inoculation, culture medium was added to the dish, and the dish was incubated for 4 to 6 days. Then, the culture medium was removed. The cells were fixed with 5% formalin according to a standard method, and stained with methylene blue; the number of plaques was determined under a stereoscopic microscope. The number of plaques in a unit volume (PFU/ml) was taken as an index (titer) of infectious virus.

8-4-2 Neutralizing Activity Test

The virus solution prepared as described above was diluted to 100 PFU/0.1 ml with SPGC storage. A 0.3-ml aliquot of the diluted virus solution was combined with 0.3 ml of an antibody solution that had been diluted 10 times with SPGC. The mixture was incubated at 37° C. for one hour. A 0.2-ml aliquot of the mixture was scattered onto HEL cells that had been placed in a 6-cm dish to inoculate the virus to the cells. The inoculation was achieved as follows: the virus liquid was being scattered repeatedly back and forth equally onto the HEL cells for one hour so that the cells could be covered with the virus solution and the cell surface was not dried.

After inoculation, 5 ml of culture medium was added to the dish, and the dish was incubated for 4 to 6 days. Then, the culture medium was removed. The cells were fixed with 5% formalin according to a standard method, and stained with methylene blue; the number of plaques was determined under a stereoscopic microscope.

The neutralizing activity of an antibody toward virus assessed by comparing the number of plaques formed in the absence of antibody (PBS alone) as a control with that in the presence of antibody (i.e., the number of plaques is decreased in the presence of a neutralizing antibody). As seen below in Table 16, the clones of Nos. 10, 24, and 94 had strong neutralizing activity.

TABLE 16

| Antibody clone name | The number of plaques in neutralization test 1st test | 2nd test | 3rd | 4th | Neutralizing activity |
|---|---|---|---|---|---|
| Control (PBS) | 42 | 46, | 48, | 50, | |
| VZ9 | * | | | | |
| VZ10 | 0 | 0 | | | +++ |
| VZ11 | 30 | 25 | | | +− |
| VZ13 | 47 | 48 | | | − |
| VZ24 | 0 | 0 | | | +++ |
| VZ36 | 14 | 15 | | | + |
| VZ49 | 40 | 43 | | | − |
| VZ60 | 15 | 9 | | | + |
| VZ64 | 41 | 42 | | | − |
| VZ77 | 36 | * | | | |
| VZ86 | 46 | 50 | | | − |
| VZ89 | 32 | 33 | | | +− |
| VZ94 | 1 | 2 | | | ++ |
| VZ100 | 29 | 28 | | | +− |
| VZ102 | 19 | 24 | | | +− |

Neutralizing activity: Very strong, +++; Strong, ++; Detectable, +; Unassignable, +−; None, −
*: incapable measurement because of contamination of microorganism.

8-4-3 Conclusions Concerning the Neutralization Test

According to the present invention, three phage clones were obtained, which strongly suppressed plaque formation, i.e., clones VZ10, VZ24, and VZ94. The nucleotide sequences of the heavy chain and light chain in the phage clones, and the amino acid sequences encoded by the same are shown below under the following SEQ ID NOs:

| Clone. No. | Heavy chain | Light chain |
| --- | --- | --- |
| VZ10 (nucleotide sequence) | 73 | 74 |
| VZ10 (amino acid sequence) | 91 | 92 |
| VZ24 (nucleotide sequence) | 75 | 76 |
| VZ24 (amino acid sequence) | 93 | 94 |
| VZ94 (nucleotide sequence) | 77 | 78 |
| VZ94 (amino acid sequence) | 95 | 96 |

The nucleotide sequences of the clones are different from one another. Thus, when used practically for clinical purposes, the neutralizing activities can be synergistic. Because the antibody genes are already available and characterized, when intending to practically use these antibody variable domains, one can construct complete immunoglobulin molecules containing the constant domains from the antibody variable domains or conjugate the domains with an enzyme by a relatively simple method.

INDUSTRIAL APPLICABILITY

The present invention provided an antibody library which contains antibody molecules having functionally active conformation at a high rate, or a library of genes encoding the same. Firstly, the preparation of the gene library of the present invention comprises selecting genes encoding the light chain variable region capable of forming functionally active conformation in combination with the heavy chain variable domain. The gene library of the present invention constructed by combining the resulting light chain variable region genes selected with the heavy chain variable region genes can mimic the antibody repertoire comprising functionally active antibodies. The antibody library of the present invention constructed via the step of selecting functional antibody molecules can be assumed to mimic, in vitro, the in vivo antibody repertoire.

An antibody library containing functionally active antibodies at a high rate can be prepared based on the gene library of the present invention. Functionally active antibodies can be isolated efficiently by screening such an antibody library. In preparing antibody libraries known to those skilled in the art, the major interest had been in only increasing the number of antibody variations in such libraries. However, the present inventors focused on the quality of antibodies constituting such libraries and then established a means of improving the quality in the present invention. Thus, the present invention provides an entirely different viewpoint on the in vitro construction of antibody libraries and method for screening antibodies.

The heavy chain diversity can be used to full advantage in antibody libraries prepared according to the present invention. This advantage is not confined to allowing to mimic the in vivo antibody diversity in vitro. Based on the present invention, for example, a method for introducing artificial mutations, such as error-prone PCR, can be used to full advantage. Specifically, in the present invention, theoretically, the heavy chain variations due to the introduced mutations fully contribute to the antibody variations. Because the light chain which allows the re-holding of a functionally active antibody in combination with the heavy chain, are selected according to the present invention. It contrasts with that, in a previous library known to those skilled in the art, when the light chain does not allow the formation of a functionally active antibody molecule, no antibody activity is detectable in spite of the presence of effective mutation in the heavy chain and thus screening may results in failure.

The invention claimed is:

1. A method for preparing a gene library comprising combinations of different light chain variable region genes and heavy chain variable region genes of immunoglobulin, the method comprising:
   (a) selecting a plurality of human derived different light chain variable region genes encoding light chain molecules, wherein the light chain variable region genes are selected by detecting a holding structure of a complex through an association of a heavy chain variable chain molecule with a light chain variable chain molecule to form Fab, further wherein the association is detected by both an antibody of I) and an antibody of II) binding to Fab, when the light chain molecule is combined with an expression product of a heavy chain variable region gene encoding the heavy chain variable chain molecule, wherein I) is an antibody against the light chain, and II) is an antibody against the heavy chain or Fab, and wherein the plurality of different light chain variable region genes is 100 for each of κ chain genes and λ chain genes;
   (b) recovering each of the human derived different light chain variable region gene selected in step (a) from the heavy chain variable region gene;

(c) constructing a gene library consisting of a collection of the human derived different light chain variable region genes recovered in step b); and (d) combining the gene library of light chain variable region genes obtained in step (c) with one or more libraries of genes encoding human derived heavy chain variable regions having a full repertoire of heavy chain variable region genes, whereby the resulting gene library maintains diversity in the heavy chain variable region.

2. A gene library comprising combinations of different light chain variable region genes and heavy chain variable region genes of immunoglobulin, wherein the gene library is obtained by:

(a) selecting a plurality of human derived different light chain variable region genes encoding light chain molecules, wherein the light chain variable region genes are selected by detecting a holding structure of a complex through an association of a heavy chain variable chain molecule with a light chain variable chain molecule to form Fab, further wherein the association is detected by both an antibody of I) and an antibody of II) binding to Fab, when the light chain molecule is combined with an expression product of a heavy chain variable region gene encoding the heavy chain variable chain molecule, wherein I) is an antibody against the light chain, and II) is an antibody against the heavy chain or Fab, and wherein the plurality of different light chain variable region genes is 100 for each of κ chain genes and λ chain genes;

(b) recovering each of the human derived different light chain variable region gene selected in step (a) from the heavy chain variable region gene;

(c) constructing a library consisting of a collection of the human derived different light chain variable region genes recovered in step b); and (d) combining the library of light chain variable region genes obtained in step (c) with one or more libraries of genes encoding human derived heavy chain variable regions having a full repertoire of heavy chain variable region genes, whereby the resulting gene library maintains diversity in the heavy chain variable region.

3. An antibody library that comprises antibody proteins encoded by genes from a gene library, wherein the gene library is obtained by:

(a) selecting a plurality of human derived different light chain variable region genes encoding light chain molecules, wherein the light chain variable region genes are selected by detecting a holding structure of a complex through an association of a heavy chain variable chain molecule with a light chain variable chain molecule to form Fab, further wherein the association is detected by both an antibody of I) and an antibody of II) binding to Fab, when the light chain molecule is combined with an expression product of a heavy chain variable region gene encoding the heavy chain variable chain molecule, wherein I) is an antibody against the light chain, and II) is an antibody against the heavy chain or Fab, and wherein the plurality of different light chain variable region genes is 100 for each of κ chain genes and λ chain genes;

(b) recovering each of the human derived different light chain variable region gene selected in step (a) from the heavy chain variable region gene;

(c) constructing a library consisting of a collection of the human derived different light chain variable region genes recovered in step b); and (d) combining the library of light chain variable region genes obtained in step (c) with one or more libraries of genes encoding human derived heavy chain variable regions having a full repertoire of heavy chain variable region genes, whereby the resulting library maintains diversity in the heavy chain variable region.

4. The method of claim 1, wherein the antibody against the light chain for selecting the κ chain genes and λ chain genes is an antibody against the kappa chain and an antibody against the lambda chain, respectively.

5. The method of claim 4, wherein the κ chain genes and λ chain genes are selected with an ELISA for the detection of binding between the antibody of I) and the antibody of II) to Fab, wherein I) is an antibody against the kappa chain or an antibody against the lambda chain and II) is an antibody against the heavy chain or Fab.

6. The method of claim 5, wherein each of 100 of the κ chain genes and λ chain genes are selected from those having the highest reactivity rank detected by the ELISA.

7. The method of claim 1, wherein the library of genes encoding the human derived heavy chain variable regions is obtained from naive B cells.

8. The method of claim 1, wherein redundancy within the plurality of different light chain variable region genes selected is removed prior to step (b).

9. The gene library according to claim 2, wherein the antibody against the light chain for selecting the κ chain genes and λ chain genes is an antibody against the kappa chain and an antibody against the lambda chain, respectively.

10. The antibody library according to claim 3, wherein the antibody against the light chain for selecting the κ chain genes and λ chain genes is an antibody against the kappa chain and an antibody against the lambda chain, respectively.

\* \* \* \* \*

UNITED STATES PATENT AND TRADEMARK OFFICE
CERTIFICATE OF CORRECTION

PATENT NO. : 8,101,553 B1
APPLICATION NO. : 10/204773
DATED : January 24, 2012
INVENTOR(S) : Yoshikazu Kurosawa et al.

Page 1 of 1

It is certified that error appears in the above-identified patent and that said Letters Patent is hereby corrected as shown below:

In the Claims:

At Column 124, Claim 1, line numbers 65-67, please replace "(b) recovering each of the human derived different light chain variable region gene selected in step (a) from the heavy chain variable region gene;" with --(b) recovering each of the human derived different light chain variable region genes selected in step (a) from the heavy chain variable region gene;--.

At Column 125, Claim 2, line numbers 30-32, please replace "(b) recovering each of the human derived different light chain variable region gene selected in step (a) from the heavy chain variable region gene;" with --(b) recovering each of the human derived different light chain variable region genes selected in step (a) from the heavy chain variable region gene;--.

At Column 126, Claim 3, line numbers 11-13, please replace "(b) recovering each of the human derived different light chain variable region gene selected in step (a) from the heavy chain variable region gene;" with --(b) recovering each of the human derived different light chain variable region genes selected in step (a) from the heavy chain variable region gene;--.

Signed and Sealed this
Twenty-ninth Day of May, 2012

David J. Kappos
*Director of the United States Patent and Trademark Office*

SEQUENCE LISTING

```
<160> NUMBER OF SEQ ID NOS: 106

<210> SEQ ID NO 1
<211> LENGTH: 120
<212> TYPE: PRT
<213> ORGANISM: Homo sapiens

<400> SEQUENCE: 1

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Gly Pro Ser Gly Ser Phe Asp Ala Phe Asp Ile Trp Gly Gln
            100                 105                 110

Gly Thr Thr Val Thr Val Ser Ser
        115                 120
```

```
<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caggaaacag ctatgac                                                   17

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
actgctgcag ctgaacctcg gc                                             22

<210> SEQ ID NO 4
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagctgcagc agtctggggc agagcttgtg aagccagggg cctcagtcaa gttgtcctgc    60
acagcttctg gcttcaacat taa                                            83

<210> SEQ ID NO 5
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatccttcca atccactcta gacccttttc aggcctctgc ttcacccagt gcatataggt    60
gtctttaatg ttgaagccag a                                              81

<210> SEQ ID NO 6
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagggtctag agtggattgg aaggattgat cctgcgagtg gtaatactaa atatgacccg    60
aaggacaagg ccactataac agca                                           84

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
```

```
cagggaattc agctgtaggt aggctgtgtt ggaggatgtg tctgctgtta tagtggcctt    60
gtcctt                                                              66

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagctgaatt ccctgacatc tgaggacact gccgtctatt actgtgctgg t             51

<210> SEQ ID NO 9
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggaacacggt gaccgtggtg ccttggcccc agtagtcaaa gttgccgtaa tcataaccag    60
cacagtaata gac                                                      73

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagctcccgg gatagctctt attaatggtg atgatggtga tgacaatctc ttgg          54

<210> SEQ ID NO 11
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gacatcgagc tcacccagtc tccagcctcc ctttctgcgt ctgtgggaga aactgtcacc    60
atcacatgt                                                           69

<210> SEQ ID NO 12
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgctggtac catgctaaat aattgtgaat attcccactt gctcgacatg tgatggtgac    60
agt                                                                 63

<210> SEQ ID NO 13
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13
gcatggtacc agcagaaacc agggaaatct cctcagctcc tggtctat              48

<210> SEQ ID NO 14
<211> LENGTH: 81
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ttgtgttccg gatccactgc cactgaacct tgatggcaca ccatctgcta aggtttttgc   60
attatagacc aggagctgag g                                            81

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttgatctcg agcttggtgc ctccaccgaa cgtccacgga gtact                  45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agtactccgt ggacgttcgg tggaggcacc aagctcgaga tcaaa                  45

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcgacagcta                                                         10

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttgatctcg agcttggtac ctccaccgaa                                   30

<210> SEQ ID NO 19
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 19
aatggagtcg actggcgcgc cgaacactca ttcctgttga agct                    44

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
accctggtca ccgtctcctc agcctccacc aagggcccat cggtcttccc cctgg        55

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aagctgctgg agggcacggt cacgacgctg ctgaggg                            37

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggactctact ccctcagcag cgtcgtgacc gtgccc                             36

<210> SEQ ID NO 23
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atggtgatga tggtgatgac aagatttggg ctcaactttc ttgtccacct tggtgttgct   60
ggg                                                                 63

<210> SEQ ID NO 24
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcaagctccc gggatagctc ttattaatgg tgatgatggt gatgacaaga tttggg       56

<210> SEQ ID NO 25
<211> LENGTH: 33
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 25
ggcaccacgg tcaccgtctc gagcgcctcc acc                                    33

<210> SEQ ID NO 26
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caccacggtc accgtctcct caggcggtgg cggatcaggt ggcggtggaa gtggcggtgg        60
tgggtctact agtgacatcg agctcaccca g                                      91

<210> SEQ ID NO 27
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgggtgagc tcgatgtcac tagtagaccc accaccgcca cttccaccgc cacctgatcc        60
gccaccgcct gaggagacgg tgaccgtggt g                                      91

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caggaaacag ctatgac                                                      17

<210> SEQ ID NO 29
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
actgctgcag ctgaacctcg gccatggccg gctgggccgc ag                          42

<210> SEQ ID NO 30
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtcctcgcaa ctgcggccca gccggccatg gccgacatcc agatgaccca gtctcc           56

<210> SEQ ID NO 31
```

```
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtcctcgcaa ctgcggccca gccggccatg gccgatgttg tgatgactca gtctcc        56

<210> SEQ ID NO 32
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtcctcgcaa ctgcggccca gccggccatg gccgaaattg tgttgacgca gtctcc        56

<210> SEQ ID NO 33
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtcctcgcaa ctgcggccca gccggccatg gccgacatcg tgatgaccca gtctcc        56

<210> SEQ ID NO 34
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtcctcgcaa ctgcggccca gccggccatg gccgaaacga cactcacgca gtctcc        56

<210> SEQ ID NO 35
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtcctcgcaa ctgcggccca gccggccatg gccgaaattg tgctgactca gtctcc        56

<210> SEQ ID NO 36
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtcctcgcaa ctgcggccca gccggccatg gcccagtctg tgttgacgca gccgcc        56

<210> SEQ ID NO 37
<211> LENGTH: 56
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
gtcctcgcaa ctgcggccca gccggccatg gcccagtctg ccctgactca gcctgc          56

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtcctcgcaa ctgcggccca gccggccatg gcctcctatg tgctgactca gccacc          56

<210> SEQ ID NO 39
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtcctcgcaa ctgcggccca gccggccatg gcctcttctg agctgactca ggaccc          56

<210> SEQ ID NO 40
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtcctcgcaa ctgcggccca gccggccatg gcccacgtta tactgactca accgcc          56

<210> SEQ ID NO 41
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtcctcgcaa ctgcggccca gccggccatg gcccaggctg tgctcactca gccgcc          56

<210> SEQ ID NO 42
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtcctcgcaa ctgcggccca gccggccatg gccaatttta tgctgactca gcccca          56

<210> SEQ ID NO 43
<211> LENGTH: 44
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 43
tcgactggcg cgccgaacac tctcccctgt tgaagctctt tgtg                     44

<210> SEQ ID NO 44
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcgactggcg cgccgaacat tctgtagggg ccactgtctt ctc                      43

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
attaataaga gctatcccgg                                                20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atggagtcgg gaaggaagtc                                                20

<210> SEQ ID NO 47
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gtcctcgcaa ctgcggccca gccggccatg gcccaggtgc agctggtgca gtctgg        56

<210> SEQ ID NO 48
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtcctcgcaa ctgcggccca gccggccatg gcccaggtca acttaaggga gtctgg        56

<210> SEQ ID NO 49
<211> LENGTH: 56
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 49
gtcctcgcaa ctgcggccca gccggccatg gccgaggtgc agctggtgga gtctgg        56

<210> SEQ ID NO 50
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtcctcgcaa ctgcggccca gccggccatg gcccaggtgc agctgcagga gtcggg        56

<210> SEQ ID NO 51
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtcctcgcaa ctgcggccca gccggccatg gcccaggtgc agctgttgca gtctgc        56

<210> SEQ ID NO 52
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtcctcgcaa ctgcggccca gccggccatg gcccaggtac agctgcagca gtcagg        56

<210> SEQ ID NO 53
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtcctcgcaa ctgcggccca gccggccatg gcccagrtca ccttgaagga gtctggtcc     59

<210> SEQ ID NO 54
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtcctcgcaa ctgcggccca gccggccatg gcccaggtgc agctacagca gtgggg        56

<210> SEQ ID NO 55
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
```

```
gtcctcgcaa ctgcggccca gccggccatg gccgaggtgc agctggtgca gtctgg         56
```

<210> SEQ ID NO 56
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

```
gtcctcgcaa ctgcggccca gccggccatg gcccaggtgc agctggtgca atctgggtct     60
gagt                                                                  64
```

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
ggtggaggca ctcgagacgg tgaccagggt gc                                   32
```

<210> SEQ ID NO 58
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
ggtggaggca ctcgagacgg tgaccattgt cc                                   32
```

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

```
ggtggaggca ctcgagacgg tgaccagggt tc                                   32
```

<210> SEQ ID NO 60
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

```
ggtggaggca ctcgagacgg tgaccgtggt cc                                   32
```

<210> SEQ ID NO 61
<211> LENGTH: 368
<212> TYPE: DNA
<213> ORGANISM: Homo sapiens

<400> SEQUENCE: 61

```
caggtacagc tgcagcagtc aggcccagga ctggtgaagc cttcggagac cctgtccctc     60
```

```
acatgcactg tctctggttc ctccatcagt agttactact ggagttggat ccgacagccc    120
ccagggaagg gactggagtg gattgggtat atctattaca atgggagcac caactacaac    180
ccctccctca agagtcgagt caccatatca gtcgacacgt ccaagaagca gttctccctg    240
aagctgagtt ctgtgaccgc tgcggacacg gccgtgtatt attgtgcggg ccaaccgttt    300
ttgcagaggt cactctatcc gggggcagtg tggcattggg gccagggaac cctggtcacc    360
gtctcgag                                                              368

<210> SEQ ID NO 62
<211> LENGTH: 354
<212> TYPE: DNA
<213> ORGANISM: Homo sapiens

<400> SEQUENCE: 62
cagtctgtgt tgacgcagcc gccctcagcg tctgggaccc ccgggcagag ggtcaccatc     60
tcttgttctg gaagcagctc caacatcgga agtaatactg taaactggta ccagcagctc    120
ccaggaacgg cccccaaact cctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggttatgtg    300
gtattcggcg gagggaccaa gctgaccgtc ctaggtcagc ccaaggctgc cccc          354

<210> SEQ ID NO 63
<211> LENGTH: 378
<212> TYPE: DNA
<213> ORGANISM: Homo sapiens

<400> SEQUENCE: 63
caggtgcagc tggtgcagtc tggggctgag gtgaagaagc ctgggtcctc ggtgaaggtc     60
tcctgcaagg cttctggagg caccttccac aaccatgcaa tcaactgggt gcgacaagcc    120
cctggacaag gcttgagtg gatgggaggg atcaccccta tccttggttc agcaaactac    180
gcacagaagt tccagggcag agtcacgatt accgcggacg aatccacgag gacagcctac    240
atggagctga gcggcctgac atctgaggac acggccgtgt attactgtgc gagagacttg    300
ggagctacga cgggctgggg gcaaaagtac tacaacggta tggacgtctg ggggcaaggg    360
acaattgtca ccgtctcg                                                  378

<210> SEQ ID NO 64
<211> LENGTH: 345
<212> TYPE: DNA
<213> ORGANISM: Homo sapiens

<400> SEQUENCE: 64
tcttctgagc tgactcagga ccctgctgtg tctgtggcct tgggacagac agtcaggatc     60
acatgccaag agacagcct cagaagctat tatgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactgggc tcaggcggaa    240 gatgaggctg actattactg taactcccgg gacagcagtg gtaaccatta tgtcttcgga    300
actgggacca aggtcaccgt tctaggtcag cccaaggcca acccc                    345

<210> SEQ ID NO 65
<211> LENGTH: 375
<212> TYPE: DNA
<213> ORGANISM: Homo sapiens
```

```
<400> SEQUENCE: 65
gaggtgcagc tggtggagtc tggggctgag gtgaagaagc ctgggtcctc ggtgaaggtc      60
tcctgcaagg cttctggagg caccttccac aaccatgcaa tcaactgggt gcgacaagcc     120
cctggacaag ggcttgagtg gatgggagag atcacccctt ccttggttc agcaaactac      180 gcacagaagt tccagggcag agtcacaatt accgcggacg aatccacgag acagcctac      240 atggagctga cggcctgac atctgaggac acggccgtgt attactgtgc gagagacttg      300
ggagctacga cgggctgggg caaaagtact acaacggtat ggacgtctgg ggcaagggac     360
acggtcaccg tctcg                                                      375

<210> SEQ ID NO 66
<211> LENGTH: 345
<212> TYPE: DNA
<213> ORGANISM: Homo sapiens

<400> SEQUENCE: 66
tcttctgagc tgactcagga ccctgctgtg tctgtggcct tgggacagac agtcaggatc      60
acatgccaag agacagcct cagaagctat tatgcaagct ggtaccagca aaagccagga     120
caggcccctg tacttgtcat ctatgggaaa acaaccggc cctcagggat cccagaccga      180
ttctctggct ccagctcagg aaacacagcc tccttgacca tcactgggc tcaggcggaa      240 gatgaggctg actattactg taactcccgg acagcagtg gtaaccatct ggtgttcggc      300
ggagggacca agctgaccgt cctaggtcag cccaaggctg ccccc                     345

<210> SEQ ID NO 67
<211> LENGTH: 360
<212> TYPE: DNA
<213> ORGANISM: Homo sapiens

<400> SEQUENCE: 67
gaggtgcagc tggtggagtc tgggggaggc ttggtaaagc ctgggggtc ccttagactc       60 tcctgtgcag cctctggatt cactttcagt aacgcctgga tgagctgggt ccgccaggct     120
ccagggaagg ggctggagtg ggttggccgt attaaaagca acactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtaccaca     300
ggggacggca gcagctggaa ctttgactac tggggccagg gaaccctggt caccgtctcg     360

<210> SEQ ID NO 68
<211> LENGTH: 396
<212> TYPE: DNA
<213> ORGANISM: Homo sapiens

<400> SEQUENCE: 68
cagtctgtgt tgacgcagcc gccctcagcg tctgggaccc ccgggcagag ggtcaccatc      60
tcttgttctg gaagcagctc caacatcgga agtaatactg taaactggta ccagcagctc     120
ccaggaacgg cccccaaact cctcatctat agtaataatc agcggcctc agggggtccct     180 gaccgattct ctggctccaa gtctggcacc tcagcctccc tggccatcag tgggctccag     240
tctgaggatg aggctgatta ttactgtgca gcatgggatg acagcctgaa tggttatgtc      300
ttcggaattg ggaccaaggt caccgtccta ggtcagccca aggccaaccc cactgtcact     360
ctgttcccgc cctcctctga ggagctccaa gccaac                                396

<210> SEQ ID NO 69
```

```
<211> LENGTH: 399
<212> TYPE: DNA
<213> ORGANISM: Homo sapiens

<400> SEQUENCE: 69
caggtgcagc tggtgcagtc tggggctgag gtgaagaagc ctgggtcctc ggtgaacgtc      60
tcctgcaagg tttctggagg catcttcagc aactatgcta tcagctgggt gcgacaggcc     120
cctggacagg ggcttgagtg gatgggaggg atcgtccta tatttggaac accaaactac      180
gcacagaggt tccaggacag agtcacaatc acgtcggacg aatcaacgac cacagtctac     240
atggagttga gcagcctgac atctgcggac acggccgttt atttctgtgc gagagatgag     300
gggcattgtg gtgaaaccgc ctgctcgggg ctatggtctc ccgaactctt ctactactac     360
atggacgtct ggggcgaggg gaccacggtc accgtctcg                            399

<210> SEQ ID NO 70
<211> LENGTH: 342
<212> TYPE: DNA
<213> ORGANISM: Homo sapiens

<400> SEQUENCE: 70
gacatcgtga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta ccccgatcac cttcggccaa     300
gggacacgac tggagattaa acgaactgtg gctgcaccat ct                        342

<210> SEQ ID NO 71
<211> LENGTH: 357
<212> TYPE: DNA
<213> ORGANISM: Homo sapiens

<400> SEQUENCE: 71
caggtgcagc tgcaggagtc gggcccagga ctggtgaagc cttcggagac cctgtccctc      60
acctgcactg tcgctggtgc ctccgtcagc agtgacaatt actactggac ctggatccgg     120
cagccccccg ggaagggact ggagtggatt gggtttttct cttacagtga gagcaccaac     180
tataatccct ccctcaagag tcgagtcacc atgtcaatag acacgtccaa gaaccagctc     240
tccctgaagc tgagttctgt gaccgctgcg gacacggccg tgtattactg tgcgagagag     300
ggttggagtg ggagttattt tgactattgg ggccggggaa ccctggtcac cgtctcg        357

<210> SEQ ID NO 72
<211> LENGTH: 360
<212> TYPE: DNA
<213> ORGANISM: Homo sapiens

<400> SEQUENCE: 72
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
ccgtacactt ttggccaggg gaccaagctg gagatcaaac gaactgtggc tgcaccatct     360
```

<210> SEQ ID NO 73
<211> LENGTH: 393
<212> TYPE: DNA
<213> ORGANISM: Homo sapiens

<400> SEQUENCE: 73

```
caggtgcagc tacaggagtc gggggaggc ttggtacagc ctggagggtc cctgagactc      60
tcctgtgcag gttctggatt catcttcagc ggttatgaaa tgaattgggt ccgccaggct     120
ccagggaagg ggctggagtg gatctcatac attagtagta gtggtagtac catatactac    180
gcagactctg tgaagggccg attcaccatc tccagagaca cgcgaagaa ttcactgcat      240
ctgcaaatga acagcctgag agccgaggac acggctgttt attactgtgc gcgagatatc    300
cgaagtttcg attttggag tggttattat gtcggttttt cctcgggtgg cggtatggac     360
gtctggggcc aagggaccac ggtcaccgtc tcg                                  393
```

<210> SEQ ID NO 74
<211> LENGTH: 321
<212> TYPE: DNA
<213> ORGANISM: Homo sapiens

<400> SEQUENCE: 74

```
gacatcgtga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccatcac cttcggccaa     300
gggacacgac tggagattaa a                                              321
```

<210> SEQ ID NO 75
<211> LENGTH: 357
<212> TYPE: DNA
<213> ORGANISM: Homo sapiens

<400> SEQUENCE: 75

```
gaggtgcagc tggtggagtc tgggggaggc ctggtcaagc ctgggggtc cctgagactc      60
tcctgtgcag cctctggatt caccttcaat tactatggca tgaactgggt ccgccaggct    120
ccagggaagg ggctggaatg ggtctcgtcc attagtagtg gtgggactta catacactac    180
tcagactcag tgaagggccg attcaccgtc tccagagaca cgccaagaa ttcactgttt     240
ctggaaatga acagcctgag agccgaggac acggctattt attactgtgc gagagattgg    300
gaaagtcata gttacgccct tgactactgg ggccagggaa ccctggtcac cgtctcg       357
```

<210> SEQ ID NO 76
<211> LENGTH: 339
<212> TYPE: DNA
<213> ORGANISM: Homo sapiens

<400> SEQUENCE: 76

```
caggctgtgc tcactcagcc gtcctcagtg tctggggtcc cagggcagag ggtcaccatc      60
tcctgcactg ggagcagctc caacatcggg gcaggttatg atgtacactg gtaccagcag    120
cttccaggaa cagcccccaa actcctcatc tatggtaaca gcaatcggcc ctcagggtc     180
cctgaccgat tctctggctc caagtctggc acctcagcct ccctggccat cactgggttc    240
caggctgagg atgaggctga ttattactgc cagtcctatg acagcagcct gagtggtcat    300
```

```
gtggtattcg gcggagggac caagctgacc gtcctaggt                            339
```

<210> SEQ ID NO 77
<211> LENGTH: 360
<212> TYPE: DNA
<213> ORGANISM: Homo sapiens

<400> SEQUENCE: 77

```
gaggtgcagc tggtggagtc tgggggaggc gtggtccagc ctgggaggtc cctgagactc     60
tcctgtggag cctctggatt caccttcaat acctatgcaa tgcactgggt ccgccaggct    120
ccaggcaagg ggatggagtg ggtggcagtt gtttcagatg gtggaggcaa taggtactat    180
gcagcctccg tgaagggccg gttcaccatc tccagagaca attccaagaa taccttgttt    240
ctgcaattga cacccctgag acctgaggac acggctgtct attactgtgc gagatctcgg    300
gggaaccact actactacgg catggacgtc tggggccgag gaccacggt caccgtctcg     360
```

<210> SEQ ID NO 78
<211> LENGTH: 321
<212> TYPE: DNA
<213> ORGANISM: Homo sapiens

<400> SEQUENCE: 78

```
gacatccaga tgacccagtc tccatcttcc gtgtctgcat ctgtaggaga cagagtcacc     60
atcacttgtc gggcgagtca gggtattagc agttggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacaatt tccccctcac tttcggcgga    300
gggaccaagg tggagatcaa a                                              321
```

<210> SEQ ID NO 79
<211> LENGTH: 122
<212> TYPE: PRT
<213> ORGANISM: Homo sapiens

<400> SEQUENCE: 79

```
Gln Val Gln Leu Gln Gln Ser Gly Pro Gly Leu Val Lys Pro Ser Glu
 1               5                  10                  15

Thr Leu Ser Leu Thr Cys Thr Val Ser Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Asn Gly Ser Thr Asn Tyr Asn Pro Ser Leu Lys
    50                  55                  60

Ser Arg Val Thr Ile Ser Val Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Gly Gln Pro Phe Leu Gln Arg Ser Leu Tyr Pro Gly Ala Val Trp His
            100                 105                 110

Trp Gly Gln Gly Thr Leu Val Thr Val Ser
        115                 120
```

<210> SEQ ID NO 80
<211> LENGTH: 118
<212> TYPE: PRT
<213> ORGANISM: Homo sapiens -continued

```
<400> SEQUENCE: 80

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Thr Val Asn Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Val Phe Gly Gly Gly Thr Lys Leu Thr Val Leu Gly
                100                 105                 110

Gln Pro Lys Ala Ala Pro
        115

<210> SEQ ID NO 81
<211> LENGTH: 126
<212> TYPE: PRT
<213> ORGANISM: Homo sapiens

<400> SEQUENCE: 81

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe His Asn His
             20                  25                  30

Ala Ile Asn Trp Val Arg Gln Ala Pro Gly Gln Gly Leu Glu Trp Met
             35                  40                  45

Gly Gly Ile Thr Pro Ile Leu Gly Ser Ala Asn Tyr Ala Gln Lys Phe
 50                  55                  60

Gln Gly Arg Val Thr Ile Thr Ala Asp Glu Ser Thr Arg Thr Ala Tyr
 65                  70                  75                  80

Met Glu Leu Ser Gly Leu Thr Ser Glu Asp Thr Ala Val Tyr Tyr Cys
                 85                  90                  95

Ala Arg Asp Leu Gly Ala Thr Gly Trp Gly Gln Lys Tyr Tyr Asn
                100                 105                 110

Gly Met Asp Val Trp Gly Gln Gly Thr Ile Val Thr Val Ser
        115                 120                 125

<210> SEQ ID NO 82
<211> LENGTH: 115
<212> TYPE: PRT
<213> ORGANISM: Homo sapiens

<400> SEQUENCE: 82

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80
```

-continued

Asp Glu Ala Asp Tyr Tyr Cys Asn Ser Arg Asp Ser Ser Gly Asn His
                85                  90                  95

Tyr Val Phe Gly Thr Gly Thr Lys Val Thr Val Leu Gly Gln Pro Lys
            100                 105                 110

Ala Asn Pro
        115

<210> SEQ ID NO 83
<211> LENGTH: 125
<212> TYPE: PRT
<213> ORGANISM: Homo sapiens

<400> SEQUENCE: 83

Glu Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe His Asn His
                20                  25                  30

Ala Ile Asn Trp Val Arg Gln Ala Pro Gly Gln Gly Leu Glu Trp Met
            35                  40                  45

Gly Glu Ile Thr Pro Phe Leu Gly Ser Ala Asn Tyr Ala Gln Lys Phe
        50                  55                  60

Gln Gly Arg Val Thr Ile Thr Ala Asp Glu Ser Thr Arg Thr Ala Tyr
65                  70                  75                  80

Met Glu Leu Ser Gly Leu Thr Ser Glu Asp Thr Ala Val Tyr Tyr Cys
                85                  90                  95

Ala Arg Asp Leu Gly Ala Thr Thr Gly Trp Gly Lys Ser Thr Thr Thr
            100                 105                 110

Val Trp Thr Ser Gly Ala Arg Asp Thr Val Thr Val Ser
        115                 120                 125

<210> SEQ ID NO 84
<211> LENGTH: 115
<212> TYPE: PRT
<213> ORGANISM: Homo sapiens

<400> SEQUENCE: 84

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Val Phe Gly Gly Gly Thr Lys Leu Thr Val Leu Gly Gln Pro Lys
            100                 105                 110

Ala Ala Pro
        115

<210> SEQ ID NO 85
<211> LENGTH: 120
<212> TYPE: PRT
<213> ORGANISM: Homo sapiens

```
<400> SEQUENCE: 85

Glu Val Gln Leu Val Glu Ser Gly Gly Leu Val Lys Pro Gly Gly
  1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Asn Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Gly Asp Gly Ser Ser Trp Asn Phe Asp Tyr Trp Gly
            100                 105                 110

Gln Gly Thr Leu Val Thr Val Ser
        115                 120

<210> SEQ ID NO 86
<211> LENGTH: 132
<212> TYPE: PRT
<213> ORGANISM: Homo sapiens

<400> SEQUENCE: 86

Gln Ser Val Leu Thr Gln Pro Pro Ser Ala Ser Gly Thr Pro Gly Gln
  1               5                  10                  15

Arg Val Thr Ile Ser Cys Ser Gly Ser Ser Ser Asn Ile Gly Ser Asn
             20                  25                  30

Thr Val Asn Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Ile Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn
130

<210> SEQ ID NO 87
<211> LENGTH: 133
<212> TYPE: PRT
<213> ORGANISM: Homo sapiens

<400> SEQUENCE: 87

Gln Val Gln Leu Val Gln Ser Gly Ala Glu Val Lys Lys Pro Gly Ser
  1               5                  10                  15

Ser Val Asn Val Ser Cys Lys Val Ser Gly Gly Ile Phe Ser Asn Tyr
             20                  25                  30

Ala Ile Ser Trp Val Arg Gln Ala Pro Gly Gln Gly Leu Glu Trp Met
         35                  40                  45

Gly Gly Ile Val Pro Ile Phe Gly Thr Pro Asn Tyr Ala Gln Arg Phe
     50                  55                  60
```

```
Gln Asp Arg Val Thr Ile Thr Ser Asp Glu Ser Thr Thr Val Tyr
 65                  70                  75                  80

Met Glu Leu Ser Ser Leu Thr Ser Ala Asp Thr Ala Val Tyr Phe Cys
                 85                  90                  95

Ala Arg Asp Glu Gly His Cys Gly Glu Thr Ala Cys Ser Gly Leu Trp
            100                 105                 110

Ser Pro Glu Leu Phe Tyr Tyr Tyr Met Asp Val Trp Gly Glu Gly Thr
        115                 120                 125

Thr Val Thr Val Ser
        130

<210> SEQ ID NO 88
<211> LENGTH: 114
<212> TYPE: PRT
<213> ORGANISM: Homo sapiens

<400> SEQUENCE: 88

Asp Ile Val Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Ile
                 85                  90                  95

Thr Phe Gly Gln Gly Thr Arg Leu Glu Ile Lys Arg Thr Val Ala Ala
            100                 105                 110

Pro Ser

<210> SEQ ID NO 89
<211> LENGTH: 119
<212> TYPE: PRT
<213> ORGANISM: Homo sapiens

<400> SEQUENCE: 89

Gln Val Gln Leu Gln Glu Ser Gly Pro Gly Leu Val Lys Pro Ser Glu
  1               5                  10                  15

Thr Leu Ser Leu Thr Cys Thr Val Ala Gly Ala Ser Val Ser Ser Asp
             20                  25                  30

Asn Tyr Tyr Trp Thr Trp Ile Arg Gln Pro Pro Gly Lys Gly Leu Glu
         35                  40                  45

Trp Ile Gly Phe Phe Ser Tyr Ser Glu Ser Thr Asn Tyr Asn Pro Ser
 50                  55                  60

Leu Lys Ser Arg Val Thr Met Ser Ile Asp Thr Ser Lys Asn Gln Leu
 65                  70                  75                  80

Ser Leu Lys Leu Ser Ser Val Thr Ala Ala Asp Thr Ala Val Tyr Tyr
                 85                  90                  95

Cys Ala Arg Glu Gly Trp Ser Gly Ser Tyr Phe Asp Tyr Trp Gly Arg
            100                 105                 110

Gly Thr Leu Val Thr Val Ser
            115
```

```
<210> SEQ ID NO 90
<211> LENGTH: 120
<212> TYPE: PRT
<213> ORGANISM: Homo sapiens

<400> SEQUENCE: 90

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys Arg Thr Val Ala Ala Pro Ser
        115                 120

<210> SEQ ID NO 91
<211> LENGTH: 131
<212> TYPE: PRT
<213> ORGANISM: Homo sapiens

<400> SEQUENCE: 91

Gln Val Gln Leu Gln Glu Ser Gly Gly Gly Leu Val Gln Pro Gly Gly
 1               5                  10                  15

Ser Leu Arg Leu Ser Cys Ala Gly Ser Gly Phe Ile Phe Ser Gly Tyr
            20                  25                  30

Glu Met Asn Trp Val Arg Gln Ala Pro Gly Lys Gly Leu Glu Trp Ile
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu His
65                  70                  75                  80

Leu Gln Met Asn Ser Leu Arg Ala Glu Asp Thr Ala Val Tyr Tyr Cys
                85                  90                  95

Ala Arg Asp Ile Arg Ser Phe Asp Phe Trp Ser Gly Tyr Val Gly
            100                 105                 110

Phe Ser Ser Gly Gly Gly Met Asp Val Trp Gly Gln Gly Thr Thr Val
        115                 120                 125

Thr Val Ser
    130

<210> SEQ ID NO 92
<211> LENGTH: 107
<212> TYPE: PRT
<213> ORGANISM: Homo sapiens

<400> SEQUENCE: 92

Asp Ile Val Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Ile
                 85                  90                  95

Thr Phe Gly Gln Gly Thr Arg Leu Glu Ile Lys
                100                 105
```

<210> SEQ ID NO 93
<211> LENGTH: 119
<212> TYPE: PRT
<213> ORGANISM: Homo sapiens

<400> SEQUENCE: 93

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Asn Tyr Tyr
                 20                  25                  30

Gly Met Asn Trp Val Arg Gln Ala Pro Gly Lys Gly Leu Glu Trp Val
             35                  40                  45

Ser Ser Ile Ser Ser Gly Gly Thr Tyr Ile His Tyr Ser Asp Ser Val
 50                  55                  60

Lys Gly Arg Phe Thr Val Ser Arg Asp Asn Ala Lys Asn Ser Leu Phe
 65                  70                  75                  80

Leu Glu Met Asn Ser Leu Arg Ala Glu Asp Thr Ala Ile Tyr Tyr Cys
                 85                  90                  95

Ala Arg Asp Trp Glu Ser His Ser Tyr Ala Leu Asp Tyr Trp Gly Gln
                100                 105                 110

Gly Thr Leu Val Thr Val Ser
        115
```

<210> SEQ ID NO 94
<211> LENGTH: 113
<212> TYPE: PRT
<213> ORGANISM: Homo sapiens

<400> SEQUENCE: 94

```
Gln Ala Val Leu Thr Gln Pro Ser Ser Val Ser Gly Val Pro Gly Gln
 1               5                  10                  15

Arg Val Thr Ile Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
             35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Phe
 65                  70                  75                  80

Gln Ala Glu Asp Glu Ala Asp Tyr Tyr Cys Gln Ser Tyr Asp Ser Ser
                 85                  90                  95

Leu Ser Gly His Val Val Phe Gly Gly Gly Thr Lys Leu Thr Val Leu
                100                 105                 110

Gly
```

<210> SEQ ID NO 95

```
<211> LENGTH: 120
<212> TYPE: PRT
<213> ORGANISM: Homo sapiens

<400> SEQUENCE: 95

Glu Val Gln Leu Val Glu Ser Gly Gly Val Val Gln Pro Gly Arg
 1               5                  10                  15

Ser Leu Arg Leu Ser Cys Gly Ala Ser Gly Phe Thr Phe Asn Thr Tyr
            20                  25                  30

Ala Met His Trp Val Arg Gln Ala Pro Gly Lys Gly Met Glu Trp Val
        35                  40                  45

Ala Val Val Ser Asp Gly Gly Asn Arg Tyr Tyr Ala Ala Ser Val
    50                  55                  60

Lys Gly Arg Phe Thr Ile Ser Arg Asp Asn Ser Lys Asn Thr Leu Phe
65                  70                  75                  80

Leu Gln Leu Asn Thr Leu Arg Pro Glu Asp Thr Ala Val Tyr Tyr Cys
                85                  90                  95

Ala Arg Ser Arg Gly Asn His Tyr Tyr Tyr Gly Met Asp Val Trp Gly
            100                 105                 110

Arg Gly Thr Thr Val Thr Val Ser
        115                 120

<210> SEQ ID NO 96
<211> LENGTH: 107
<212> TYPE: PRT
<213> ORGANISM: Homo sapiens

<400> SEQUENCE: 96

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Leu
                85                  90                  95

Thr Phe Gly Gly Gly Thr Lys Val Glu Ile Lys
            100                 105

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
taatacgact cactataggg                                              20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 98
attaataaga gctatcccgg                                                    20

<210> SEQ ID NO 99
<211> LENGTH: 2321
<212> TYPE: DNA
<213> ORGANISM: Artificial Sequence
<220> FEATURE:
<223> OTHER INFORMATION: Description of Artificial Sequence: Synthetic
      cloning vector
<220> FEATURE:
<221> NAME/KEY: CDS
<222> LOCATION: (40)..(237)
<220> FEATURE:
<221> NAME/KEY: CDS
<222> LOCATION: (248)..(670)
<220> FEATURE:
<221> NAME/KEY: CDS
<222> LOCATION: (728)..(901)
<220> FEATURE:
<221> NAME/KEY: CDS
<222> LOCATION: (909)..(1889)
<220> FEATURE:
<221> NAME/KEY: CDS
<222> LOCATION: (1921)..(2304)

<400> SEQUENCE: 99

```
aagcttgcat gcaaattcta tttcaaggag acagtcata atg aaa tac cta ttg          54
                                          Met Lys Tyr Leu Leu
                                            1               5 cct acg gca gcc gct gga ttg tta tta ctc gct gcc caa cca gcg atg         102
Pro Thr Ala Ala Ala Gly Leu Leu Leu Leu Ala Ala Gln Pro Ala Met
              10                  15                  20 gcc cag gtg cag ctg cag cag tct ggg gca gag ctt gtg aag cca ggg         150
Ala Gln Val Gln Leu Gln Gln Ser Gly Ala Glu Leu Val Lys Pro Gly
         25                  30                  35 gcc tca gtc aag ttg tcc tgc aca gct tct ggc ttc aac att aaa gac         198
Ala Ser Val Lys Leu Ser Cys Thr Ala Ser Gly Phe Asn Ile Lys Asp
     40                  45                  50 acc tat atg cac tgg gtg aag cag agg cct gaa aag ggt ctagaattcc          247
Thr Tyr Met His Trp Val Lys Gln Arg Pro Glu Lys Gly
 55                  60                  65 ctg aca tct gag gac act gcc gtc tat tac tgt gct ggt tat gat tac         295
Leu Thr Ser Glu Asp Thr Ala Val Tyr Tyr Cys Ala Gly Tyr Asp Tyr
             70                  75                  80 ggc aac ttt gac tac tgg ggc caa ggc acc acg gtc acc gtc tcg agc         343
Gly Asn Phe Asp Tyr Trp Gly Gln Gly Thr Thr Val Thr Val Ser Ser
         85                  90                  95 gcc tcc acc aag ggc cca tcg gtc ttc ccc ctg gca ccc tcc tcc aag         391
Ala Ser Thr Lys Gly Pro Ser Val Phe Pro Leu Ala Pro Ser Ser Lys
    100                 105                 110 agc acc tct ggg ggc aca gcg gcc ctg ggc tgc ctg gtc aag gac tac         439
Ser Thr Ser Gly Gly Thr Ala Ala Leu Gly Cys Leu Val Lys Asp Tyr
115                 120                 125                 130 ttc ccc gaa ccg gtg acg gtg tcg tgg aac tca ggc gcc ctg acc agc         487
Phe Pro Glu Pro Val Thr Val Ser Trp Asn Ser Gly Ala Leu Thr Ser
                135                 140                 145 ggc gtg cac acc ttc ccg gct gtc cta cag tcc tca gga ctc tac tcc         535
Gly Val His Thr Phe Pro Ala Val Leu Gln Ser Ser Gly Leu Tyr Ser
            150                 155                 160 ctc agc agc gtc gtg acc gtg ccc tcc agc agc ttg ggc acc cag acc         583
Leu Ser Ser Val Val Thr Val Pro Ser Ser Ser Leu Gly Thr Gln Thr
        165                 170                 175 tac atc tgc aac gtg aat cac aag ccc agc aac acc aag gtg gac aag         631
```

-continued

| | | | | | | | | | | | | | |
|---|---|---|---|---|---|---|---|---|---|---|---|---|---|
|Tyr|Ile|Cys|Asn|Val|Asn|His|Lys|Pro|Ser|Asn|Thr|Lys|Val Asp Lys|
| |180| | | |185| | | |190| | | | |

```
aaa gtt gag ccc aaa tct tgt cat cac cat cat cac cat taataagagc          680
Lys Val Glu Pro Lys Ser Cys His His His His His His
195             200                 205 tatcccggga gcttgcatgc aaattctatt tcaaggagac agtcata atg aaa tac         736
                                                   Met Lys Tyr
                                                           210 cta ttg cct acg gca gcc gct gga ttg tta tta ctc gcg gcc cag ccg         784
Leu Leu Pro Thr Ala Ala Ala Gly Leu Leu Leu Ala Ala Gln Pro
                215                 220                 225 gcc atg gcc act agt gac atc gag ctc acc cag tct cca gcc tcc ctt         832
Ala Met Ala Thr Ser Asp Ile Glu Leu Thr Gln Ser Pro Ala Ser Leu
            230                 235                 240 tct gcg tct gtg gga gaa act gtc acc atc aca tgt cga gca agt ggg         880
Ser Ala Ser Val Gly Glu Thr Val Thr Ile Thr Cys Arg Ala Ser Gly
            245                 250                 255 aat att cac aat tat tta gca tggtacc aag ctc gag atc aaa cgg gct         929
Asn Ile His Asn Tyr Leu Ala         Lys Leu Glu Ile Lys Arg Ala
            260             265                 270 gat gct gca cca act gta tcc atc ttc cca cca tcc agt gag cag tta         977
Asp Ala Ala Pro Thr Val Ser Ile Phe Pro Pro Ser Ser Glu Gln Leu
            275                 280                 285 aca tct gga ggt gcc tca gtc gtg tgc ttc ttg aac agc ttc tac ccc        1025
Thr Ser Gly Gly Ala Ser Val Val Cys Phe Leu Asn Ser Phe Tyr Pro
            290                 295                 300 aaa gac atc aat gtc aag tgg aag att gat ggc agt gaa cga caa aat        1073
Lys Asp Ile Asn Val Lys Trp Lys Ile Asp Gly Ser Glu Arg Gln Asn
305                 310                 315                 320 ggc gtc ctg aac agt tgg act gat cag gac agc aaa gac agc acc tac        1121
Gly Val Leu Asn Ser Trp Thr Asp Gln Asp Ser Lys Asp Ser Thr Tyr
                325                 330                 335 agc atg agc agc acc ctc acg ttg acc aag gac gag tat gaa cga cat        1169
Ser Met Ser Ser Thr Leu Thr Leu Thr Lys Asp Glu Tyr Glu Arg His
                340                 345                 350 aac agc tat acc tgt gag gcc act cac aag aca tca act tca ccc att        1217
Asn Ser Tyr Thr Cys Glu Ala Thr His Lys Thr Ser Thr Ser Pro Ile
            355                 360                 365 gtc aag agc ttc aac agg aat gag tgt tcg gcg cgc cag tcg act cca        1265
Val Lys Ser Phe Asn Arg Asn Glu Cys Ser Ala Arg Gln Ser Thr Pro
370                 375                 380 ttc gtt tgt gaa tat caa ggc caa tcg tct gac ctg cct caa cct cct        1313
Phe Val Cys Glu Tyr Gln Gly Gln Ser Ser Asp Leu Pro Gln Pro Pro
385                 390                 395                 400 gtc aat gct ggc ggc ggc tct ggt ggt ggt tct ggt ggc ggc tct gag        1361
Val Asn Ala Gly Gly Gly Ser Gly Gly Gly Ser Gly Gly Gly Ser Glu
                405                 410                 415 ggt ggt ggc tct gag ggt ggc ggt tct gag ggt ggc ggc tct gag gga        1409
Gly Gly Gly Ser Glu Gly Gly Gly Ser Glu Gly Gly Gly Ser Glu Gly
                420                 425                 430 ggc ggt tcc ggt ggt ggc tct ggt tcc ggt gat ttt gat tat gaa aag        1457
Gly Gly Ser Gly Gly Gly Ser Gly Ser Gly Asp Phe Asp Tyr Glu Lys
            435                 440                 445 atg gca aac gct aat aag ggg gct atg acc gaa aat gcc gat gaa aac        1505
Met Ala Asn Ala Asn Lys Gly Ala Met Thr Glu Asn Ala Asp Glu Asn
            450                 455                 460 gcg cta cag tca gac gct aaa ggc aaa ctt gat tct gtc gct act gat        1553
Ala Leu Gln Ser Asp Ala Lys Gly Lys Leu Asp Ser Val Ala Thr Asp
465                 470                 475                 480 tac ggt gct gct atc gat ggt ttc att ggt gac gtt tcc ggc ctt gct        1601
```

```
                Tyr Gly Ala Ala Ile Asp Gly Phe Ile Gly Asp Val Ser Gly Leu Ala
                                485                 490                 495 aat ggt aat ggt gct act ggt gat ttt gct ggc tct aat tcc caa atg           1649
Asn Gly Asn Gly Ala Thr Gly Asp Phe Ala Gly Ser Asn Ser Gln Met
            500                 505                 510 gct caa gtc ggt gac ggt gat aat tca cct tta atg aat aat ttc cgt           1697
Ala Gln Val Gly Asp Gly Asp Asn Ser Pro Leu Met Asn Asn Phe Arg
            515                 520                 525 caa tat tta cct tcc ctc cct caa tcg gtt gaa tgt cgc cct ttt gtc           1745
Gln Tyr Leu Pro Ser Leu Pro Gln Ser Val Glu Cys Arg Pro Phe Val
            530                 535                 540 ttt ggc gct ggt aaa cca tat gaa ttt tct att gat tgt gac aaa ata           1793
Phe Gly Ala Gly Lys Pro Tyr Glu Phe Ser Ile Asp Cys Asp Lys Ile
545                 550                 555                 560 aac tta ttc cgt ggt gtc ttt gcg ttt ctt tta tat gtt gcc acc ttt           1841
Asn Leu Phe Arg Gly Val Phe Ala Phe Leu Leu Tyr Val Ala Thr Phe
                565                 570                 575 atg tat gta ttt tct acg ttt gct aac ata ctg cgt aat aag gag tct           1889
Met Tyr Val Phe Ser Thr Phe Ala Asn Ile Leu Arg Asn Lys Glu Ser
                580                 585                 590 taatcatgcc agttcttttg ggtgctagct g tcg act gcg caa cac gat gaa            1941
                                   Ser Thr Ala Gln His Asp Glu
                                                       595 gcc gta gac aac aaa ttc aac aaa gaa caa caa aac gcg ttc tat gag           1989
Ala Val Asp Asn Lys Phe Asn Lys Glu Gln Gln Asn Ala Phe Tyr Glu
600                 605                 610                 615 atc tta cat tta cct aac tta aac gaa gaa caa cga aac gcc ttc atc           2037
Ile Leu His Leu Pro Asn Leu Asn Glu Glu Gln Arg Asn Ala Phe Ile
                620                 625                 630 caa agt tta aaa gat gac cca agc caa agc gct aac ctt tta gca gaa           2085
Gln Ser Leu Lys Asp Asp Pro Ser Gln Ser Ala Asn Leu Leu Ala Glu
                635                 640                 645 gct aaa aag cta aat gat gct cag gcg ccg aaa gta gac aac aaa ttc           2133
Ala Lys Lys Leu Asn Asp Ala Gln Ala Pro Lys Val Asp Asn Lys Phe
                650                 655                 660 aac aaa gaa caa caa aac gcg ttc tat gag atc tta cat tta cct aac           2181
Asn Lys Glu Gln Gln Asn Ala Phe Tyr Glu Ile Leu His Leu Pro Asn
665                 670                 675 tta aac gaa gaa caa cga aac gcc ttc atc caa agt tta aaa gat gac           2229
Leu Asn Glu Glu Gln Arg Asn Ala Phe Ile Gln Ser Leu Lys Asp Asp
680                 685                 690                 695 cca agc caa agc gct aac ctt tta gca gaa gct aaa aag cta aat gat           2277
Pro Ser Gln Ser Ala Asn Leu Leu Ala Glu Ala Lys Lys Leu Asn Asp
                700                 705                 710 gct cag gcg ccg aaa gta gac gcg aat tagctgggaa ttaattc                    2321
Ala Gln Ala Pro Lys Val Asp Ala Asn
                715                 720

<210> SEQ ID NO 100
<211> LENGTH: 207
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 100

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30
```

```
Leu Val Lys Pro Gly Ala Ser Val Lys Leu Ser Cys Thr Ala Ser Gly
         35                  40                  45

Phe Asn Ile Lys Asp Thr Tyr Met His Trp Val Lys Gln Arg Pro Glu
 50                  55                  60

Lys Gly Leu Thr Ser Glu Asp Thr Ala Val Tyr Tyr Cys Ala Gly Tyr
 65                  70                  75                  80

Asp Tyr Gly Asn Phe Asp Tyr Trp Gly Gln Gly Thr Thr Val Thr Val
                 85                  90                  95

Ser Ser Ala Ser Thr Lys Gly Pro Ser Val Phe Pro Leu Ala Pro Ser
                100                 105                 110

Ser Lys Ser Thr Ser Gly Gly Thr Ala Ala Leu Gly Cys Leu Val Lys
            115                 120                 125

Asp Tyr Phe Pro Glu Pro Val Thr Val Ser Trp Asn Ser Gly Ala Leu
130                 135                 140

Thr Ser Gly Val His Thr Phe Pro Ala Val Leu Gln Ser Ser Gly Leu
145                 150                 155                 160

Tyr Ser Leu Ser Ser Val Val Thr Val Pro Ser Ser Ser Leu Gly Thr
                165                 170                 175

Gln Thr Tyr Ile Cys Asn Val Asn His Lys Pro Ser Asn Thr Lys Val
                180                 185                 190

Asp Lys Lys Val Glu Pro Lys Ser Cys His His His His His His
            195                 200                 205

<210> SEQ ID NO 101
<211> LENGTH: 385
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 101

Met Lys Tyr Leu Leu Pro Thr Ala Ala Ala Gly Leu Leu Leu Leu Ala
 1               5                  10                  15

Ala Gln Pro Ala Met Ala Thr Ser Asp Ile Glu Leu Thr Gln Ser Pro
                 20                  25                  30

Ala Ser Leu Ser Ala Ser Val Gly Glu Thr Val Thr Ile Thr Cys Arg
             35                  40                  45

Ala Ser Gly Asn Ile His Asn Tyr Leu Ala Lys Leu Glu Ile Lys Arg
 50                  55                  60

Ala Asp Ala Ala Pro Thr Val Ser Ile Phe Pro Pro Ser Ser Glu Gln
 65                  70                  75                  80

Leu Thr Ser Gly Gly Ala Ser Val Val Cys Phe Leu Asn Ser Phe Tyr
                 85                  90                  95

Pro Lys Asp Ile Asn Val Lys Trp Lys Ile Asp Gly Ser Glu Arg Gln
                100                 105                 110

Asn Gly Val Leu Asn Ser Trp Thr Asp Gln Asp Ser Lys Asp Ser Thr
            115                 120                 125

Tyr Ser Met Ser Ser Thr Leu Thr Leu Thr Lys Asp Glu Tyr Glu Arg
130                 135                 140

His Asn Ser Tyr Thr Cys Glu Ala Thr His Lys Thr Ser Thr Ser Pro
145                 150                 155                 160

Ile Val Lys Ser Phe Asn Arg Asn Glu Cys Ser Ala Arg Gln Ser Thr
                165                 170                 175

Pro Phe Val Cys Glu Tyr Gln Gly Gln Ser Ser Asp Leu Pro Gln Pro
                180                 185                 190
```

-continued

```
Pro Val Asn Ala Gly Gly Ser Gly Gly Ser Gly Gly Ser
    195                 200                 205

Glu Gly Gly Ser Glu Gly Gly Ser Glu Gly Gly Ser Glu
    210                 215                 220

Gly Gly Ser Gly Gly Ser Gly Ser Gly Asp Phe Asp Tyr Glu
225                 230                 235                 240

Lys Met Ala Asn Ala Asn Lys Gly Ala Met Thr Glu Asn Ala Asp Glu
            245                 250                 255

Asn Ala Leu Gln Ser Asp Ala Lys Gly Lys Leu Asp Ser Val Ala Thr
                260                 265                 270

Asp Tyr Gly Ala Ala Ile Asp Gly Phe Ile Gly Asp Val Ser Gly Leu
                275                 280                 285

Ala Asn Gly Asn Gly Ala Thr Gly Asp Phe Ala Gly Ser Asn Ser Gln
290                 295                 300

Met Ala Gln Val Gly Asp Gly Asp Asn Ser Pro Leu Met Asn Asn Phe
305                 310                 315                 320

Arg Gln Tyr Leu Pro Ser Leu Pro Gln Ser Val Glu Cys Arg Pro Phe
                325                 330                 335

Val Phe Gly Ala Gly Lys Pro Tyr Glu Phe Ser Ile Asp Cys Asp Lys
                340                 345                 350

Ile Asn Leu Phe Arg Gly Val Phe Ala Phe Leu Leu Tyr Val Ala Thr
                355                 360                 365

Phe Met Tyr Val Phe Ser Thr Phe Ala Asn Ile Leu Arg Asn Lys Glu
            370                 375                 380

Ser
385

<210> SEQ ID NO 102
<211> LENGTH: 128
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 102

Ser Thr Ala Gln His Asp Glu Ala Val Asp Asn Lys Phe Asn Lys Glu
1               5                   10                  15

Gln Gln Asn Ala Phe Tyr Glu Ile Leu His Leu Pro Asn Leu Asn Glu
                20                  25                  30

Glu Gln Arg Asn Ala Phe Ile Gln Ser Leu Lys Asp Asp Pro Ser Gln
            35                  40                  45

Ser Ala Asn Leu Leu Ala Glu Ala Lys Lys Leu Asn Asp Ala Gln Ala
50                  55                  60

Pro Lys Val Asp Asn Lys Phe Asn Lys Glu Gln Gln Asn Ala Phe Tyr
65                  70                  75                  80

Glu Ile Leu His Leu Pro Asn Leu Asn Glu Glu Gln Arg Asn Ala Phe
                85                  90                  95

Ile Gln Ser Leu Lys Asp Asp Pro Ser Gln Ser Ala Asn Leu Leu Ala
            100                 105                 110

Glu Ala Lys Lys Leu Asn Asp Ala Gln Ala Pro Lys Val Asp Ala Asn
        115                 120                 125

<210> SEQ ID NO 103
<211> LENGTH: 1774
<212> TYPE: DNA
<213> ORGANISM: Artificial Sequence
<220> FEATURE:
```

-continued

```
<223> OTHER INFORMATION: Description of Artificial Sequence: Synthetic
      cloning vector
<220> FEATURE:
<221> NAME/KEY: CDS
<222> LOCATION: (40)..(237)
<220> FEATURE:
<221> NAME/KEY: CDS
<222> LOCATION: (248)..(1342)
<220> FEATURE:
<221> NAME/KEY: CDS
<222> LOCATION: (1374)..(1757)

<400> SEQUENCE: 103
```

| | | | | | | | | | | | | | | | | |
|---|---|---|---|---|---|---|---|---|---|---|---|---|---|---|---|---|
| aagcttgcat | gcaaattcta | tttcaaggag | acagtcata | atg | aaa | tac | cta | ttg | | | | | | | | 54 |
| | | | | Met | Lys | Tyr | Leu | Leu | | | | | | | | |
| | | | | 1 | | | | 5 | | | | | | | | |

| cct | acg | gca | gcc | gct | gga | ttg | tta | tta | ctc | gcg | gcc | cag | ccg | gcc | atg | 102 |
|---|---|---|---|---|---|---|---|---|---|---|---|---|---|---|---|---|
| Pro | Thr | Ala | Ala | Ala | Gly | Leu | Leu | Leu | Ala | Ala | Gln | Pro | Ala | Met | | |
| | | | 10 | | | | | 15 | | | | | 20 | | | |

| gcc | cag | gtg | cag | ctg | cag | cag | tct | ggg | gca | gag | ctt | gtg | aag | cca | ggg | 150 |
|---|---|---|---|---|---|---|---|---|---|---|---|---|---|---|---|---|
| Ala | Gln | Val | Gln | Leu | Gln | Gln | Ser | Gly | Ala | Glu | Leu | Val | Lys | Pro | Gly | |
| | | 25 | | | | | 30 | | | | | 35 | | | | |

| gcc | tca | gtc | aag | ttg | tcc | tgc | aca | gct | tct | ggc | ttc | aac | att | aaa | gac | 198 |
|---|---|---|---|---|---|---|---|---|---|---|---|---|---|---|---|---|
| Ala | Ser | Val | Lys | Leu | Ser | Cys | Thr | Ala | Ser | Gly | Phe | Asn | Ile | Lys | Asp | |
| | 40 | | | | | 45 | | | | | 50 | | | | | |

| acc | tat | atg | cac | tgg | gtg | aag | cag | agg | cct | gaa | aag | ggt | ctagaattcc | | | 247 |
|---|---|---|---|---|---|---|---|---|---|---|---|---|---|---|---|---|
| Thr | Tyr | Met | His | Trp | Val | Lys | Gln | Arg | Pro | Glu | Lys | Gly | | | | |
| 55 | | | | 60 | | | | | 65 | | | | | | | |

| ctg | aca | tct | gag | gac | act | gcc | gtc | tat | tac | tgt | gct | ggt | tat | gat | tac | 295 |
|---|---|---|---|---|---|---|---|---|---|---|---|---|---|---|---|---|
| Leu | Thr | Ser | Glu | Asp | Thr | Ala | Val | Tyr | Tyr | Cys | Ala | Gly | Tyr | Asp | Tyr | |
| | | 70 | | | | | 75 | | | | | 80 | | | | |

| ggc | aac | ttt | gac | tac | tgg | ggc | caa | ggc | acc | acg | gtc | acc | gtc | tcc | tca | 343 |
|---|---|---|---|---|---|---|---|---|---|---|---|---|---|---|---|---|
| Gly | Asn | Phe | Asp | Tyr | Trp | Gly | Gln | Gly | Thr | Thr | Val | Thr | Val | Ser | Ser | |
| | | 85 | | | | | 90 | | | | | 95 | | | | |

| ggc | ggt | ggc | gga | tca | ggt | ggc | ggt | gga | agt | ggc | ggt | ggt | ggg | tct | act | 391 |
|---|---|---|---|---|---|---|---|---|---|---|---|---|---|---|---|---|
| Gly | Gly | Gly | Gly | Ser | Gly | Gly | Gly | Gly | Ser | Gly | Gly | Gly | Gly | Ser | Thr | |
| | 100 | | | | | 105 | | | | | 110 | | | | | |

| agt | gac | atc | gag | ctc | acc | cag | tct | cca | gcc | tcc | ctt | tct | gcg | tct | gtg | 439 |
|---|---|---|---|---|---|---|---|---|---|---|---|---|---|---|---|---|
| Ser | Asp | Ile | Glu | Leu | Thr | Gln | Ser | Pro | Ala | Ser | Leu | Ser | Ala | Ser | Val | |
| 115 | | | | | 120 | | | | | 125 | | | | | 130 | |

| gga | gaa | act | gtc | acc | atc | aca | tgt | cga | gca | agt | ggg | aat | att | cac | aat | 487 |
|---|---|---|---|---|---|---|---|---|---|---|---|---|---|---|---|---|
| Gly | Glu | Thr | Val | Thr | Ile | Thr | Cys | Arg | Ala | Ser | Gly | Asn | Ile | His | Asn | |
| | | | 135 | | | | | 140 | | | | | 145 | | | |

| tat | tta | gca | tgg | tac | cag | cag | aaa | cca | ggg | aaa | tct | cct | cag | ctc | ctg | 535 |
|---|---|---|---|---|---|---|---|---|---|---|---|---|---|---|---|---|
| Tyr | Leu | Ala | Trp | Tyr | Gln | Gln | Lys | Pro | Gly | Lys | Ser | Pro | Gln | Leu | Leu | |
| | | | 150 | | | | | 155 | | | | | 160 | | | |

| gtc | tat | aat | gca | aaa | acc | tta | gca | gat | ggt | gtg | cca | tca | agg | ttc | agt | 583 |
|---|---|---|---|---|---|---|---|---|---|---|---|---|---|---|---|---|
| Val | Tyr | Asn | Ala | Lys | Thr | Leu | Ala | Asp | Gly | Val | Pro | Ser | Arg | Phe | Ser | |
| | | 165 | | | | | 170 | | | | | 175 | | | | |

| ggc | agt | gga | tcc | gga | aca | caa | tat | tct | ctc | aag | atc | aac | agc | ctg | cag | 631 |
|---|---|---|---|---|---|---|---|---|---|---|---|---|---|---|---|---|
| Gly | Ser | Gly | Ser | Gly | Thr | Gln | Tyr | Ser | Leu | Lys | Ile | Asn | Ser | Leu | Gln | |
| | 180 | | | | | 185 | | | | | 190 | | | | | |

| cct | gaa | gat | ttt | ggg | agt | tat | tac | tgt | caa | cat | ttt | tgg | agt | act | ccg | 679 |
|---|---|---|---|---|---|---|---|---|---|---|---|---|---|---|---|---|
| Pro | Glu | Asp | Phe | Gly | Ser | Tyr | Tyr | Cys | Gln | His | Phe | Trp | Ser | Thr | Pro | |
| 195 | | | | | 200 | | | | | 205 | | | | | 210 | |

| tgg | acg | ttc | ggt | gga | ggt | acc | aag | ctc | gag | tcg | act | cca | ttc | gtt | tgt | 727 |
|---|---|---|---|---|---|---|---|---|---|---|---|---|---|---|---|---|
| Trp | Thr | Phe | Gly | Gly | Gly | Thr | Lys | Leu | Glu | Ser | Thr | Pro | Phe | Val | Cys | |
| | | | 215 | | | | | 220 | | | | | 225 | | | |

| gaa | tat | caa | ggc | caa | tcg | tct | gac | ctg | cct | caa | cct | cct | gtc | aat | gct | 775 |
|---|---|---|---|---|---|---|---|---|---|---|---|---|---|---|---|---|
| Glu | Tyr | Gln | Gly | Gln | Ser | Ser | Asp | Leu | Pro | Gln | Pro | Pro | Val | Asn | Ala | |
| | | | 230 | | | | | 235 | | | | | 240 | | | |

| ggc | ggc | ggc | tct | ggt | ggt | ggt | tct | ggt | ggc | ggc | tct | gag | ggt | ggt | ggc | 823 |
|---|---|---|---|---|---|---|---|---|---|---|---|---|---|---|---|---|
| Gly | Gly | Gly | Ser | Gly | Gly | Gly | Ser | Gly | Gly | Gly | Ser | Glu | Gly | Gly | Gly | |

```
                245                250                255
tct gag ggt ggc ggt tct gag ggt ggc ggc tct gag gga ggc ggt tcc          871
Ser Glu Gly Gly Gly Ser Glu Gly Gly Gly Ser Glu Gly Gly Gly Ser
        260                265                270 ggt ggt ggc tct ggt tcc ggt gat ttt gat tat gaa aag atg gca aac          919
Gly Gly Gly Ser Gly Ser Gly Asp Phe Asp Tyr Glu Lys Met Ala Asn
275                280                285                290 gct aat aag ggg gct atg acc gaa aat gcc gat gaa aac gcg cta cag          967
Ala Asn Lys Gly Ala Met Thr Glu Asn Ala Asp Glu Asn Ala Leu Gln
                295                300                305 tca gac gct aaa ggc aaa ctt gat tct gtc gct act gat tac ggt gct         1015
Ser Asp Ala Lys Gly Lys Leu Asp Ser Val Ala Thr Asp Tyr Gly Ala
            310                315                320 gct atc gat ggt ttc att ggt gac gtt tcc ggc ctt gct aat ggt aat         1063
Ala Ile Asp Gly Phe Ile Gly Asp Val Ser Gly Leu Ala Asn Gly Asn
        325                330                335 ggt gct act ggt gat ttt gct ggc tct aat tcc caa atg gct caa gtc         1111
Gly Ala Thr Gly Asp Phe Ala Gly Ser Asn Ser Gln Met Ala Gln Val
340                345                350 ggt gac ggt gat aat tca cct tta atg aat aat ttc cgt caa tat tta         1159
Gly Asp Gly Asp Asn Ser Pro Leu Met Asn Asn Phe Arg Gln Tyr Leu
355                360                365                370 cct tcc ctc cct caa tcg gtt gaa tgt cgc cct ttt gtc ttt ggc gct         1207
Pro Ser Leu Pro Gln Ser Val Glu Cys Arg Pro Phe Val Phe Gly Ala
            375                380                385 ggt aaa cca tat gaa ttt tct att gat tgt gac aaa ata aac tta ttc         1255
Gly Lys Pro Tyr Glu Phe Ser Ile Asp Cys Asp Lys Ile Asn Leu Phe
        390                395                400 cgt ggt gtc ttt gcg ttt ctt tta tat gtt gcc acc ttt atg tat gta         1303
Arg Gly Val Phe Ala Phe Leu Leu Tyr Val Ala Thr Phe Met Tyr Val
    405                410                415 ttt tct acg ttt gct aac ata ctg cgt aat aag gag tct taatcatgcc         1352
Phe Ser Thr Phe Ala Asn Ile Leu Arg Asn Lys Glu Ser
420                425                430 agttcttttg ggtgctagct g tcg act gcg caa cac gat gaa gcc gta gac         1403
                         Ser Thr Ala Gln His Asp Glu Ala Val Asp
                                     435                440 aac aaa ttc aac aaa gaa caa caa aac gcg ttc tat gag atc tta cat         1451
Asn Lys Phe Asn Lys Glu Gln Gln Asn Ala Phe Tyr Glu Ile Leu His
        445                450                455 tta cct aac tta aac gaa gaa caa cga aac gcc ttc atc caa agt tta         1499
Leu Pro Asn Leu Asn Glu Glu Gln Arg Asn Ala Phe Ile Gln Ser Leu
    460                465                470 aaa gat gac cca agc caa agc gct aac ctt tta gca gaa gct aaa aag         1547
Lys Asp Asp Pro Ser Gln Ser Ala Asn Leu Leu Ala Glu Ala Lys Lys
475                480                485 cta aat gat gct cag gcg ccg aaa gta gac aac aaa ttc aac aaa gaa         1595
Leu Asn Asp Ala Gln Ala Pro Lys Val Asp Asn Lys Phe Asn Lys Glu
490                495                500                505 caa caa aac gcg ttc tat gag atc tta cat tta cct aac tta aac gaa         1643
Gln Gln Asn Ala Phe Tyr Glu Ile Leu His Leu Pro Asn Leu Asn Glu
            510                515                520 gaa caa cga aac gcc ttc atc caa agt tta aaa gat gac cca agc caa         1691
Glu Gln Arg Asn Ala Phe Ile Gln Ser Leu Lys Asp Asp Pro Ser Gln
        525                530                535 agc gct aac ctt tta gca gaa gct aaa aag cta aat gat gct cag gcg         1739
Ser Ala Asn Leu Leu Ala Glu Ala Lys Lys Leu Asn Asp Ala Gln Ala
    540                545                550 ccg aaa gta gac gcg aat tagctgggaa ttaattc                              1774
Pro Lys Val Asp Ala Asn
```

555

<210> SEQ ID NO 104
<211> LENGTH: 431
<212> TYPE: PRT
<213> ORGANISM: Artificial Sequence
<220> FEATURE:
<223> OTHER INFORMATION: Description of Artificial Sequence: Synthetic amino acid sequence

<400> SEQUENCE: 104

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30

Leu Val Lys Pro Gly Ala Ser Val Lys Leu Ser Cys Thr Ala Ser Gly
        35                  40                  45

Phe Asn Ile Lys Asp Thr Tyr Met His Trp Val Lys Gln Arg Pro Glu
50                  55                  60

Lys Gly Leu Thr Ser Glu Asp Thr Ala Val Tyr Tyr Cys Ala Gly Tyr
65                  70                  75                  80

Asp Tyr Gly Asn Phe Asp Tyr Trp Gly Gln Gly Thr Thr Val Thr Val
                85                  90                  95

Ser Ser Gly Gly Gly Gly Ser Gly Gly Gly Gly Ser Gly Gly Gly Gly
            100                 105                 110

Ser Thr Ser Asp Ile Glu Leu Thr Gln Ser Pro Ala Ser Leu Ser Ala
        115                 120                 125

Ser Val Gly Glu Thr Val Thr Ile Thr Cys Arg Ala Ser Gly Asn Ile
    130                 135                 140

His Asn Tyr Leu Ala Trp Tyr Gln Gln Lys Pro Gly Lys Ser Pro Gln
145                 150                 155                 160

Leu Leu Val Tyr Asn Ala Lys Thr Leu Ala Asp Gly Val Pro Ser Arg
                165                 170                 175

Phe Ser Gly Ser Gly Ser Gly Thr Gln Tyr Ser Leu Lys Ile Asn Ser
            180                 185                 190

Leu Gln Pro Glu Asp Phe Gly Ser Tyr Tyr Cys Gln His Phe Trp Ser
        195                 200                 205

Thr Pro Trp Thr Phe Gly Gly Gly Thr Lys Leu Glu Ser Thr Pro Phe
    210                 215                 220

Val Cys Glu Tyr Gln Gly Gln Ser Ser Asp Leu Pro Gln Pro Pro Val
225                 230                 235                 240

Asn Ala Gly Gly Gly Ser Gly Gly Gly Ser Gly Gly Gly Ser Glu Gly
                245                 250                 255

Gly Gly Ser Glu Gly Gly Gly Ser Glu Gly Gly Gly Ser Glu Gly Gly
            260                 265                 270

Gly Ser Gly Gly Gly Ser Gly Ser Gly Asp Phe Asp Tyr Glu Lys Met
        275                 280                 285

Ala Asn Ala Asn Lys Gly Ala Met Thr Glu Asn Ala Asp Glu Asn Ala
    290                 295                 300

Leu Gln Ser Asp Ala Lys Gly Lys Leu Asp Ser Val Ala Thr Asp Tyr
305                 310                 315                 320

Gly Ala Ala Ile Asp Gly Phe Ile Gly Asp Val Ser Gly Leu Ala Asn
                325                 330                 335

Gly Asn Gly Ala Thr Gly Asp Phe Ala Gly Ser Asn Ser Gln Met Ala
            340                 345                 350

Gln Val Gly Asp Gly Asp Asn Ser Pro Leu Met Asn Asn Phe Arg Gln
```

```
                    355                 360                 365
Tyr Leu Pro Ser Leu Pro Gln Ser Val Glu Cys Arg Pro Phe Val Phe
            370                 375                 380

Gly Ala Gly Lys Pro Tyr Glu Phe Ser Ile Asp Cys Asp Lys Ile Asn
385                 390                 395                 400

Leu Phe Arg Gly Val Phe Ala Phe Leu Leu Tyr Val Ala Thr Phe Met
            405                 410                 415

Tyr Val Phe Ser Thr Phe Ala Asn Ile Leu Arg Asn Lys Glu Ser
            420                 425                 430

<210> SEQ ID NO 105
<211> LENGTH: 128
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 105

Ser Thr Ala Gln His Asp Glu Ala Val Asp Asn Lys Phe Asn Lys Glu
1               5                   10                  15

Gln Gln Asn Ala Phe Tyr Glu Ile Leu His Leu Pro Asn Leu Asn Glu
            20                  25                  30

Glu Gln Arg Asn Ala Phe Ile Gln Ser Leu Lys Asp Asp Pro Ser Gln
        35                  40                  45

Ser Ala Asn Leu Leu Ala Glu Ala Lys Lys Leu Asn Asp Ala Gln Ala
    50                  55                  60

Pro Lys Val Asp Asn Lys Phe Asn Lys Glu Gln Gln Asn Ala Phe Tyr
65                  70                  75                  80

Glu Ile Leu His Leu Pro Asn Leu Asn Glu Glu Gln Arg Asn Ala Phe
                85                  90                  95

Ile Gln Ser Leu Lys Asp Asp Pro Ser Gln Ser Ala Asn Leu Leu Ala
            100                 105                 110

Glu Ala Lys Lys Leu Asn Asp Ala Gln Ala Pro Lys Val Asp Ala Asn
        115                 120                 125

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 106

His His His His His His
1               5
```